(12) United States Patent
Driguez et al.

(10) Patent No.: US 6,534,481 B1
(45) Date of Patent: Mar. 18, 2003

(54) SYNTHETIC POLYSACCHARIDES, PREPARATION METHOD THEREFOR AND PHARMACEUTICAL COMPOSITIONS CONTAINING SAME

(75) Inventors: Pierre Alexandre Driguez, Toulouse (FR); Philippe Duchaussoy, Toulouse (FR); Jean Marc Herbert, Tourefeuille (FR); Maurice Petitou, Paris Cedex (FR); Constant Van Boeckel, Oss (NL); Peter Grootenhuis, San Diego, CA (US); Johannes Basten, Afferden (NL); Cornelia Dreef-Tromp, Wijchen (NL)

(73) Assignees: Sanofi-Synthelabo, Paris (FR); Akzo Nobel, Arnhem (NL)

( * ) Notice: Subject to any disclaimer, the term of this patent is extended or adjusted under 35 U.S.C. 154(b) by 0 days.

(21) Appl. No.: 09/230,139
(22) PCT Filed: Jul. 8, 1997
(86) PCT No.: PCT/FR97/01344
§ 371 (c)(1),
(2), (4) Date: Sep. 7, 1999
(87) PCT Pub. No.: WO98/03554
PCT Pub. Date: Jan. 29, 1998

(30) Foreign Application Priority Data

Jul. 19, 1996 (FR) .................................... 96 09116

(51) Int. Cl.[7] .................... A61K 31/70; C07H 17/02
(52) U.S. Cl. .................... 514/25; 514/54; 536/17.2; 536/21
(58) Field of Search .................... 514/25, 56; 536/17.2, 536/21

(56) References Cited

U.S. PATENT DOCUMENTS

| 4,801,583 A | 1/1989 | Petitou et al. ............... 514/54 |
| 5,378,829 A | 1/1995 | Petitou et al. ............... 536/118 |
| 5,382,570 A | 1/1995 | Petitou et al. ............... 514/53 |
| 5,514,659 A | 5/1996 | Petitou et al. ............... 514/25 |
| 5,705,489 A | 1/1998 | Van Boeckel et al. ....... 514/25 |

FOREIGN PATENT DOCUMENTS

| EP | 0 300 099 | 1/1989 |
| EP | 0 529 715 | 3/1997 |

OTHER PUBLICATIONS

C. van Boeckel and M. Petitou, Angew. Chem. Int. Ed. Engl., Dec. 1993, 32, 1671–1690.

*Primary Examiner*—Kathleen K. Fonda
(74) *Attorney, Agent, or Firm*—Paul E. Dupont; Michael D. Alexander

(57) ABSTRACT

A synthetic polysaccharide including an antithrombin III binding domain consisting of a concatenation of five monosaccharides supporting a total of two carboxylic acid functions and at least four sulpho groups, said domain being directly bound at the non-reducing end by a thrombin binding domain including a concatenation of 10–25 monosaccharide units selected from hexoses, pentoses or deoxy sugars of which all the hydroxyl groups are etherified by a $C_{1-6}$ alkyl group or esterified in the form of sulpho groups, as well as salts and particularly pharmaceutically acceptable salts thereof, are disclosed.

33 Claims, No Drawings

SYNTHETIC POLYSACCHARIDES, PREPARATION METHOD THEREFOR AND PHARMACEUTICAL COMPOSITIONS CONTAINING SAME

This application is the U.S. National Stage entry under 35 U.S.C. §371 of PCT/FR97/01344, filed Jul. 8, 1997.

The present invention relates to novel synthetic polysaccharides possessing the anticoagulant and antithrombotic pharmacological activities of heparin.

Heparin belongs to the family of glycosaminoglycans (GAGs), which are heterogeneous natural sulphated polysaccharides.

Heparin preparations are mixtures of chains comprising a number of monosaccharide units ranging from 10 to 100 and more. In addition to this size heterogeneity there is a structural heterogeneity, as regards the nature of the constituent monosaccharides and also as regards the substituents which they bear (L. Rodén in: The Biochemistry of Glycoproteins and Glycosaminoglycans, Ed by Lennarz W. J., Plenum Press, New York and London, 267–371, 1980).

Each family of natural GAGs generally possesses a wide range of pharmacological activities. All are combined in the preparations which may be obtained from natural products. Thus, for example, the heparin and heparan sulphates possess an antithrombotic activity which is associated with the simultaneous action of several coagulation factors.

Heparin catalyses, in particular via antithrombin III (AT III), the inhibition of two enzymes involved in the blood coagulation cascade, namely factor Xa and factor IIa (or thrombin). Low molecular weight heparin (LMWH) preparations contain chains formed of 4 to 30 monosaccharides and have the property of acting more selectively on factor Xa than on thrombin.

Certain synthetic oligosaccharides, in particular those described in EP 84,999, have the property of selectively inhibiting, via antithrombin III, factor Xa without having any activity on thrombin.

It is known that the inhibition of factor Xa requires binding of the heparin to AT III via the antithrombin-binding region (ABR), and that the inhibition of factor IIa (thrombin) requires binding to AT (III), via ABR, as well as to thrombin via a less well-defined binding region (TBR).

The synthetic oligosaccharides corresponding to the ABR region of heparin are known and manifest an antithrombotic activity in venous thrombosis. These compounds are described in EP 529,715 and EP 621,282 and in Canadian patent 2,040,905.

The efficacy of these oligosaccharides in the prevention of arterial thrombosis is, nevertheless, hampered by their inability to inhibit thrombin.

A synthesis of glycoaminoglycans of heparin type which are capable of inhibiting thrombin via the AT (III) activator presents great difficulties and, indeed, this has never been achieved.

With the aim of rediscovering the activity of thrombin-inhibitor and factor Xa-inhibitor products, in EP-A-0,649,854 it has been proposed to connect two small oligosaccharides (an ABR and a TBR) by a species ("spacer") which is not involved in the biological activity.

It has now been found that novel polysaccharide derivatives may be synthesized relatively simply and are biologically active. They are, in particular, anticoagulant and antithrombotic. Furthermore, on account of the production of these polysaccharides by synthesis, it is possible to selectively modify their structure, and in particular to remove unwanted sulphate substituents involved in the interaction with certain proteins. Thus, polysaccharides may be obtained which are powerful antithrombotic and anticoagulant agents and which may furthermore escape in vivo the action of proteins such as platelet factor 4 (PF4), which neutralize the effect of heparin in particular on thrombin.

Thus, it has been found, surprisingly, that sulphated and alkylated polysaccharides may be powerful antithrombotic and anticoagulant agents depending on the arrangement of the alkyl and sulphate groups borne by the carbohydrate skeleton.

More generally, it has been found that by preparing polysaccharide sequences, it is possible to modify with precision the GAG-type activities in order to obtain very active products which have the properties of heparin.

Thus, according to one of its aspects, the present invention relates to a novel synthetic polysaccharide comprising an antithrombin III-binding region consisting of a sequence of five monosaccharides bearing in total two carboxylic acid functions and at least four sulphate groups, this region being bound directly at its non-reducing end by a thrombin-binding region comprising a sequence of 10 to 25 monosaccharide units chosen from hexoses, pentoses or deoxy sugars in which all the hydroxyl groups are, independently, etherified with a $(C_1-C_6)$alkyl group or esterified in the form of sulphate groups, as well as its salts, in particular its pharmaceutically acceptable salts.

Preferably, the invention relates to a polysaccharide as defined above, characterized in that all its hydroxyl groups are etherified with a methyl or are esterified in the form of a sulpho group and its salts, in particular its pharmaceutically acceptable salts.

The products of the present invention are, in particular, polysaccharides represented by the following formula:

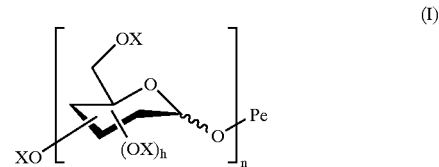
(I)

in which the wavy line denotes a bond either below or above the plane of the pyranose ring,

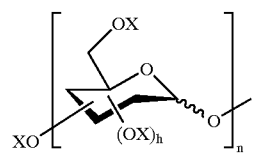

denotes a polysaccharide Po containing n identical or different monosaccharide units, which is linked via its anomeric carbon to Pe,

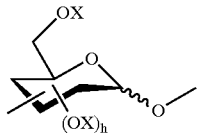

is a diagrammatic representation of a monosaccharide unit of pyranose structure chosen from hexoses, pentoses and the corresponding deoxy sugars, this unit being linked via its anomeric carbon to another monosaccharide unit, and the hydroxyl groups of this unit being substituted with identical or different groups —X, the groups X being chosen from $(C_1-C_6)$alkyl groups and sulpho groups, n is an integer from 10 to 25, Pe represents a pentasaccharide of structure:

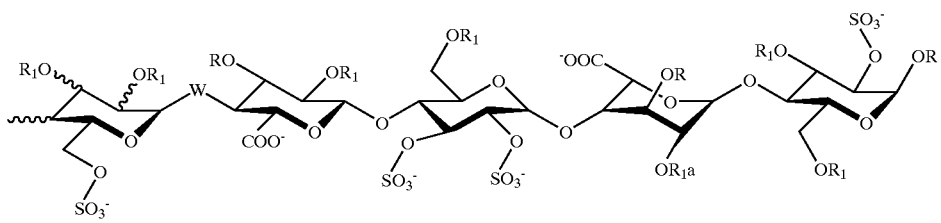

in which

R represents a $(C_1-C_6)$alkyl or a sulpho group, $R_1a$ represents $R_1$ or constitutes, with the oxygen atom to which it is attached and the carbon atom bearing the carboxylic function on the same ring, a group

R represents a $(C_1-C_6)$alkyl,

W represents an oxygen atom or a methylene group, or one of their salts, in particular a salt which is pharmaceutically acceptable.

It will be noted in general in the present description that a wavy line denotes a bond either below or above the plane of the pyranose ring.

The monosaccharides contained in Po may be identical to or different from each other, and the interglycoside linkages may be of the α or β type.

These monosaccharides are advantageously chosen from the D or L hexoses allose, altrose, glucose, mannose, galose, idose, galactose and talose (in this case h=3) or from the D or L pentoses ribose, arabinose, xylose and lyxose (in this case h=2). Other monosaccharides such as, for example, deoxy sugars may also be used (h=1 and/or —$CH_2OX$=$CH_3$).

When, in the pentasaccharides Pe, the unit W represents an oxygen atom and $R_1a$ is as defined for R, these pentasaccharides constitute known compounds described in particular in patents EP 300,099, EP 529,715, EP 621,282 and EP 649,854 as well as in the literature. They are obtained from synthons which are also described in the literature by C. van Boeckel and M. Petitou, Angew. Chem. Int. Ed. Engl., 1993, 32, 1671–1690.

When, in the pentasaccharides Pe, $R_1a$ is other than $R_1$ and/or W represents a carbon atom, these pentasaccharides are prepared using novel synthons which constitute a further aspect of the invention.

When, in the pentasaccharides Pe, the unit of L-iduronic acid type is replaced with a unit whose conformation is locked by a bridge, these pentasaccharides are prepared using novel synthons which constitute a further aspect of the invention.

Thus, according to another of its aspects, the present invention relates to novel intermediates which are useful for the preparation of compounds (I).

The polysaccharide part Po may consist of 10 to 25 alkylated and di- or trisulphated monosaccharide units.

The polysaccharide part Po may consist of 10 to 25 alkylated and mono- or disulphated monosaccharide units.

The polysaccharide part Po may consist of 10 to 25 uncharged and/or partially charged and/or fully charged alkylated monosaccharide units.

The charged or uncharged units may be dispersed along the entire length of the chain or they may, in contrast, be grouped in charged or uncharged saccharide regions.

The linkages may be 1,2; 1,3; 1,4; 1,5; 1,6; and of the α or β type.

In the present description, it has been chosen to represent the conformations $^1C_4$ for L-iduronic acid and $^4C_1$ for D-glucuronic acid, but it is well known that, in general, the conformation of the monosaccharide units in solution fluctuates. Thus, L-iduronic acid may be of $^1C_4$ $^2S_0$ or $^4C_1$ conformation.

Preferred compounds according to the invention are those of formula (I.A):

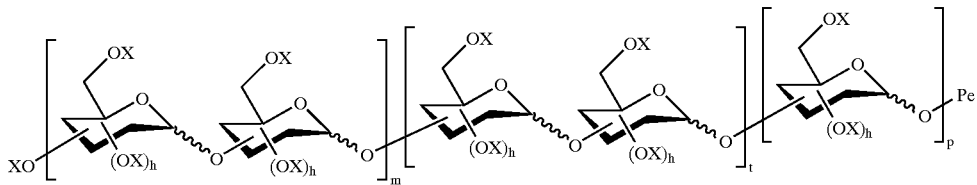

(I.A)

in which

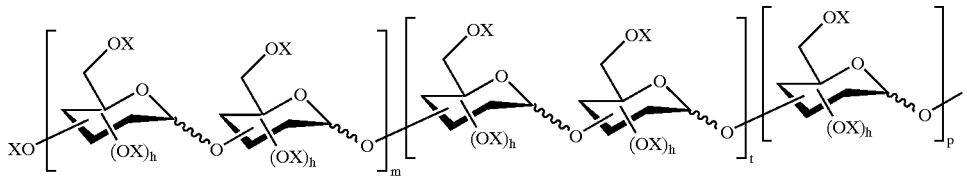

denotes a particular family of polysaccharides Po, linked via their anomeric carbon to Pe as defined for

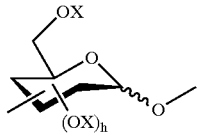

is as defined for (I), the OXs are as defined for (I) and, for the same polysaccharide, may be identical or different, the monosaccharides contained in [ ]$_m$ form a disaccharide repeated m times, the monosaccharides contained in [ ]$_t$ form a disaccharide repeated t times, m ranges from 1 to 8, t ranges from 0 to 5 and p ranges from 0 to 1, it being understood that $5 \leq m+t \leq 12$, and their salts, in particular their pharmaceutically acceptable salts.

Advantageous compounds are the salts whose anion corresponds to formula (I.1):

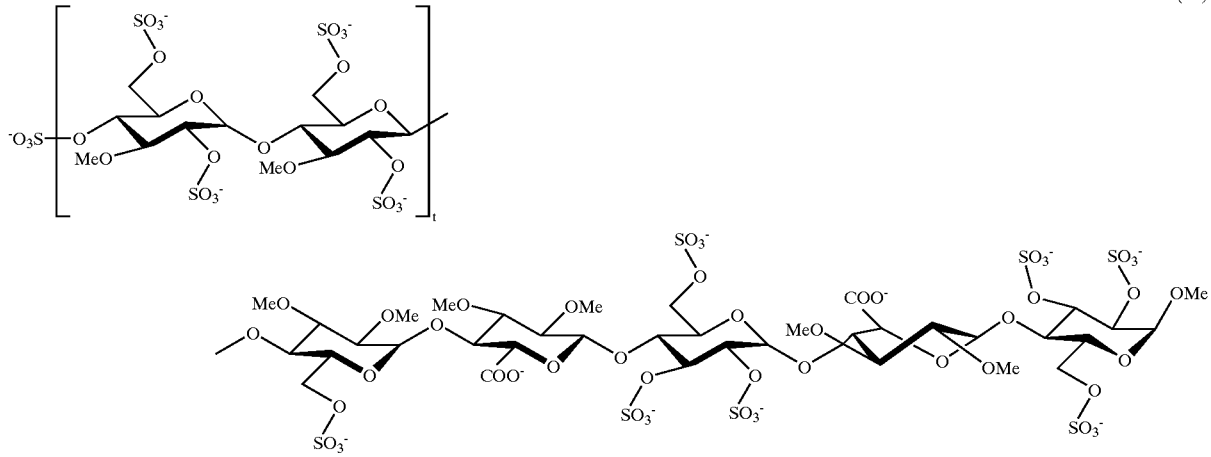

(I.1)

in which t represents 5, 6 or 7, and the cation is a pharmaceutically acceptable monovalent cation, as well as the corresponding acids.

The salts whose anion corresponds to formula (I.2):

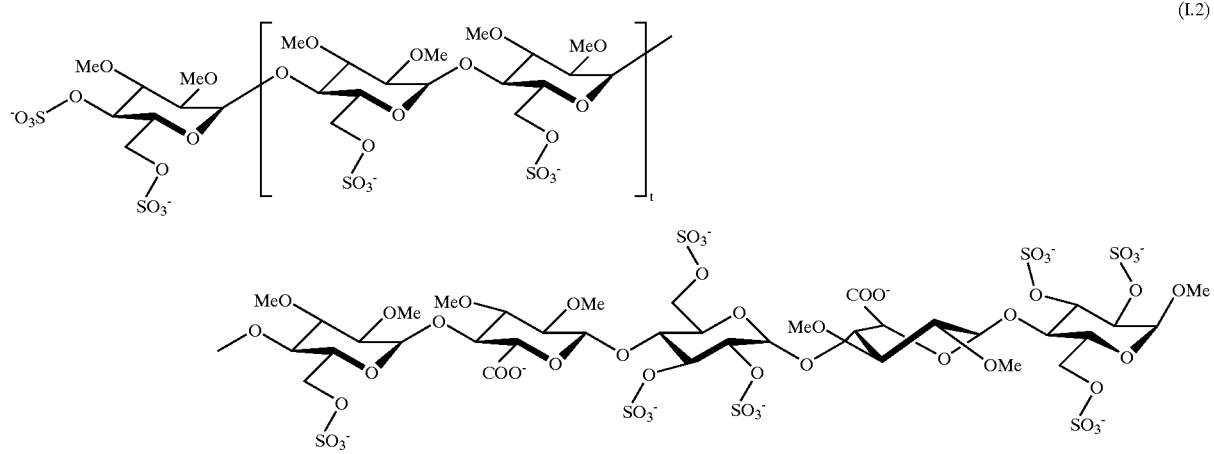

(I.2)

in which t represents 5, 6 or 7, and the cation is a pharmaceutically acceptable monovalent cation, as well as the corresponding acids, are also advantageous.

The salts whose anion has the formula (I.3):

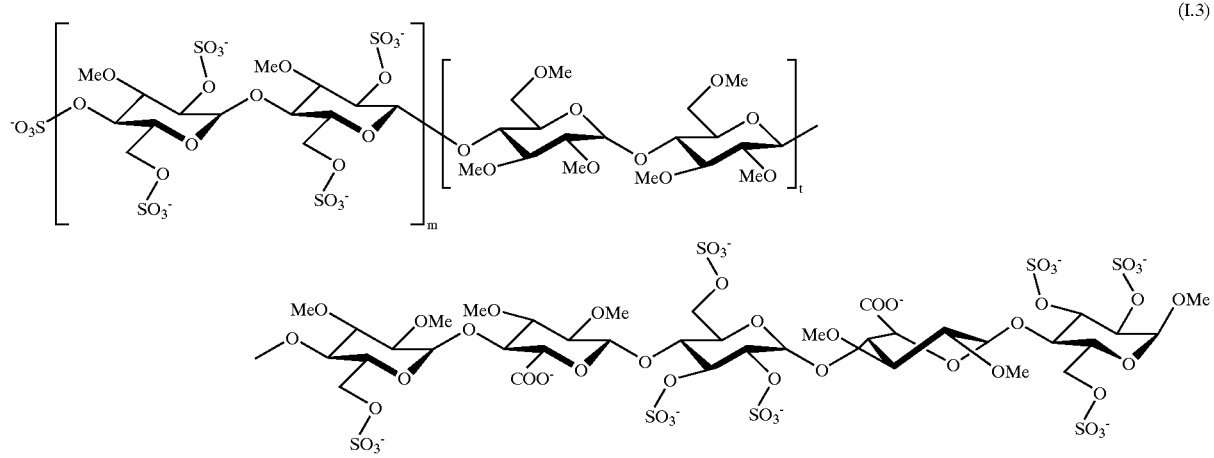

(I.3)

in which m represents 1, 2 or 3 and t represents 2, 3, 4 or 5, and the cation is a pharmaceutically acceptable monovalent cation, as well as the corresponding acids, are particularly advantageous.

Other preferred compounds according to the invention are those of formula (II.A):

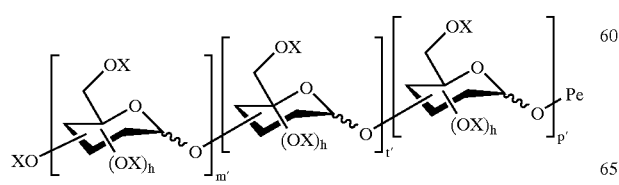

(II.A)

in which

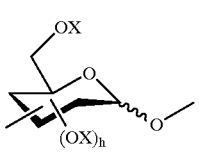

denotes a specific family of polysaccharides Po, linked via their anomeric carbon to Pe as defined for (I), is as defined for (I), the groups OX are as defined for (I) and, for the same monosaccharide, may be identical or different, the monosaccharide contained in [ ]$_{m'}$ is repeated m' times, the monosaccharide contained in [ ]$_{t'}$ is repeated t' times, and the monosaccharide contained in [ ]$_{p'}$ is repeated p' times, m' ranges from 1 to 5, t' ranges from 0 to 24, and p' ranges from 0 to 24, it being understood that $10 \leq m'+t'+p' \leq 25$, and the pharmaceutically acceptable salts thereof.

The preferred salts of the invention are those chosen from alkali metal cations and even more preferably those in which the cation is $Na^+$ or $K^+$.

The following polysaccharides are particularly preferred:

Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-[O-(3-O-methyl-2,6-di-O-sulpho-α-D-glucopyranosyl)-(1→4)-O-(3-O-methyl-2,6-di-O-sulpho-β-D-glucopyranosyl)-(1→4)]$_4$-O-(2,3-di-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-D-glucopyranosyl)-(1→4)-O-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-[O-(3-O-methyl-2,6-di-O-sulpho-α-D-glucopyranosyl)-(1,4)-O-(3-O-methyl-2,6-di-O-sulpho-β-D-glucopyranosyl)-(1→4)]$_5$-O-(2,3-di-O-methyl-6-O-sulpho-α-D-glucopyranosyl)-(1→4)-O-(2,3-di-O-methyl-β-D-glucopyranosyluronic acid)-(1,4)-O-(2,3,6-tri-O-sulpho-α-D-glucopyranosyl)-(1→4)-O-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-α-D-glucopyranosyl)-(1→4)-[O-(3-O-methyl-2,6-di-O-sulpho-β-α-D-glucopyranosyl)-(1→4)-O-(3-O-methyl-2,6-di-O-sulpho-β-D-glucopyranosyl)-(1→4)]$_6$-O-(2,3-di-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,3-di-O-methyl-α-L-idopyranosyluronic acid)-(1→4)-2,3,6-tri-O-sulpho-α-D-glucopyranoside, sodium salt Methyl O-(2,3-di-O-methyl-4,6-di-O-sulpho-α-D-glucopyranosyl)-(1→4)-[O-(2,3-di-O-methyl-6-O-sulpho-α-D-glucopyranosyl)-(1→4)-]$_{11}$-O-(2,3-di-O-methyl-β-D-glucopyranosyluronic acid)-(1,4)-O-(2,3,6-tri-O-sulpho-α-D-glucopyranosyl)-(1→4)-O-(2,3-di-O-methyl-α-L-idopyranosyluronic acid)-(1→4)-2,3,6-tri-O-sulpho-α-D-glucopyranoside, sodium salt Methyl O-(2,3-di-O-methyl-4,6-di-O-sulpho-α-D-glucopyranosyl)-(1→4)-[O-(2,3-di-O-methyl-6-O-sulpho-α-D-glucopyranosyl)-(1→4)-]$_{13}$-O-(2,3-di-O-methyl-β-D-glucopyranosyluronic acid)-(1→4)-O-(2,3-tri-O-sulpho-α-D-glucopyranosyl)-(1→4)-O-(2,3-di-O-methyl-α-L-idopyranosyluronic acid)-(1→4)-2,3,6-tri-O-sulpho-α-D-glucopyranoside, sodium salt Methyl O-(2,3-di-O-methyl-4,6-di-O-sulpho-α-D-glucopyranosyl)-(1→4)-[O-(2,3-di-O-methyl-6-O-sulpho-α-D-glucopyranosyl)-(1→4)-]$_{15}$-O-(2,3-di-O-methyl-β-D-glucopyranosyluronic acid)-(1→4)-O-(2,3-tri-O-sulpho-α-D-glucopyranosyl)-(1→4)-O-(2,3-di-O-methyl-α-L-idopyranosyluronic acid)-(1→4)-2,3,6-tri-O-sulpho-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucbpyranosyl)-(1→4)-[O-(3-O-methyl-2,6-di-O-sulpho-α-D-glucopyranosyl)-(1→4)-O-(3-O-methyl-2,6-di-O-sulpho-β-D-glucopyranosyl)-(1→4)]$_2$-[O-(2,3,6-tri-O-methyl-α-D-glucopyranosyl)-(1→4)-O-(2,3,6-tri-O-methyl-β-D-glucopyranosyl)-(1→4)]$_2$-2,3-di-O-methyl-6-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-[O-(3-O-methyl-2,6-di-O-sulpho-α-D-glucopyranosyl)-(1→4)-O-(3-O-methyl-2,6-di-O-sulpho-β-D-glucopyranosyl)-1→4)]$_2$-[O-(2,3,6-tri-O-methyl-α-D-glucopyranosyl)-(1→4)-O-(2,3,6-tri-O-methyl-β-D-glucopyranosyl)-(1→4)]$_3$-O-2,3-di-O-methyl-6-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-O-(3-O-methyl-2,6-di-O-sulpho-α-D-glucopyranosyl)-(1→4)-O-(3-O-methyl-2,6-di-O-sulpho-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_4$-O-2,3-di-O-methyl-6-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-O-(3-O-methyl-2,6-di-O-sulpho-α-D-glucopyranosyl)-(1→4)-O-(3-O-methyl-2,6-di-O-sulpho-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-2,3-di-O-methyl-6-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-lucopyranosyl)-(1→4)-O-(3-O-methyl-2,6-di-O-sulpho-β-D-glucopyranosyl)-(1→4)-[O-(2,3,6-tri-O-methyl-α-D-glucopyranosyl)-(1→4)-O-(2,3,6-tri-O-methyl-α-D-glucopyranosyl)-(1→4)]$_4$-O-2,3-di-O-methyl-6-sulpho-α-D-glucopyranosyl)-(1→4)-O-(2,3-di-O-methyl-α-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt Methyl O-(3-O-methyl-2,4,6-tri-O-sulpho-α-D-glucopyranosyl)-(1→4)-O-(3-O-methyl-2,6-di-O-sulpho-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_5$-O-2,3-di-O-methyl-6-sulpho-α-D-glucopyranosyl)-(1→4)-O-(2,3-di-O-methyl-α-D-glucopyranosyluronic acid)-(1→4)-O-(2,3,6-tri-O-sulpho-α-D-glucopyranosyl)-(1→4)-(2,3-di-O-methyl-α-L-idopyranosyluronic acid)-(1→4)-2,3,6-tri-O-sulpho-α-D-glucopyranoside, sodium salt.

The present invention relates to a process for the preparation of the compounds of formula (I), wherein, in a first step, a fully protected precursor of the desired polysaccharide (I), containing a protected precursor of the Pe region (this region being shown in Scheme 1) elongated at its non-reducing end by a protected precursor of the sulphated polysaccharide Po, is synthesized and, in a second step, the negatively-charged groups are then introduced and/or demasked.

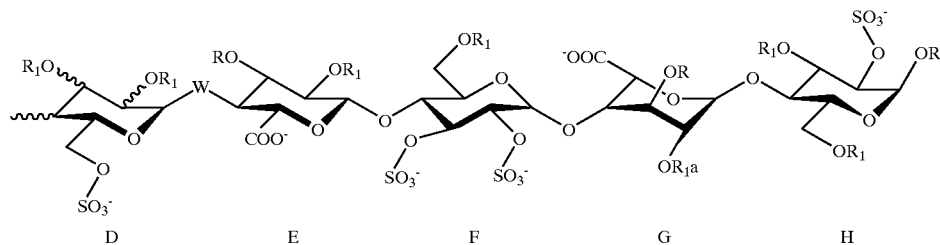

In a first approach, the fully protected precursor of the tetrasaccharide part EFGH of the pentasaccharide may be used. A polysaccharide Po which contains at its reducing-terminal end the missing unit D of Pe is then added in order to obtain, after coupling, the entire ABR which is thus restored.

In another approach, the fully protected precursor of the disaccharide part GH of the pentasaccharide may be used. A polysaccharide Po precursor of the TBR which contains at its reducing-terminal end the missing unit DEF of Pe is then added in order to obtain, after coupling, the entire ABR which is thus restored.

These Pe precursors are synthesized as indicated above from synthons described in the literature or forming part of the present invention.

The polysaccharide precursor part of Po is synthesized according to reactions which are well known to those skilled in the art, using the methods for synthesizing oligosaccharides (G. J. Boons, Tetrahedron, 1996, 52, 1095–1121) or an oligosaccharide when a glycosidic-linkage-donating oligosaccharide is coupled with a glycosidic-linkage-accepting oligosaccharide in order to lead to another oligosaccharide whose size is equal to the sum of the sizes of the two reactive species.

This sequence is repeated until the desired compound of formula (I) is obtained. The nature and profile of the charge of the desired final compound determine the nature of the chemical species used in the various steps of the synthesis, according to rules which are well known to those skilled in the art.

A preferred method for the preparation of the Po precursors according to the present invention is shown in Scheme 2 below:

SCHEME 2
Synthesis of the protected precursor of the TBR

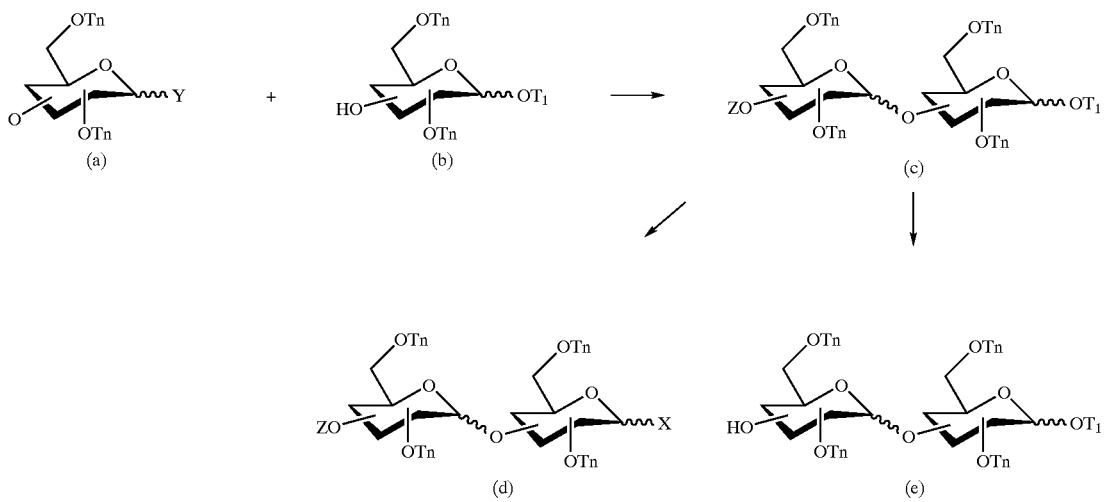

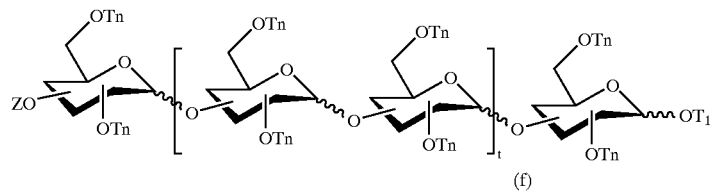

(f)

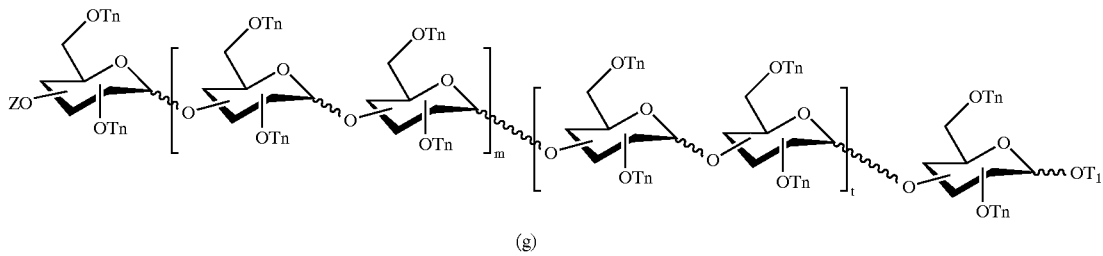

(g)

The term temporary is understood to refer to a substituent which is conserved for a limited number of steps, the term semi-permanent is understood to refer to a substituent which is conserved for a larger number of steps, and the term permanent is understood to refer to a substituent which is conserved to the end of the synthesis; the permanent substituents are removed during the final step. Certain permanent groups may form part of the final molecule.

In Scheme 2, (a) represents a glycosidic-linkage-donor monosaccharide in which Z is a temporary protecting group of a hydroxyl function and Y is an anomeric-carbon activator, Tn, which may be identical or different, are temporary, semi-permanent or permanent substituents of all the other hydroxyl functions.

The compound (b) which possesses an unsubstituted hydroxyl group represents a glycosidic-linkage-acceptor monosaccharide in which Tn, which may be identical or different, are temporary, semi-permanent or permanent substituents of the hydroxyl groups. $T_1$ is a temporary, semi-permanent or permanent protecting group of the anomeric position. It is removed when it is desired to activate the anomeric carbon.

With the aim of obtaining the compounds of the invention, the glycosidic-linkage donor (a) and the glycosidic-linkage acceptor (b) react together to give the disaccharide (c).

The disaccharide (c) obtained above is converted specifically into a glycosidic-linkage-donor disaccharide (d) by removal of $T_1$ and introduction of Y and/or into a glycosidic-linkage acceptor (e) by removal of Z.

Next, the glycosidic-linkage donor (d) and the glycosidic-linkage acceptor (e) react together to give the tetrasaccharide (f) in which t represents 1.

Repetition of this sequence of reactions gives an oligo- or a polysaccharide (f) in which t is greater than 1.

It is also possible, using the process represented in Scheme 2, to obtain a large variety of fully protected oligo- or polysaccharides such as (g) in which the oligosaccharides [ ]$_m$ and [ ]$_t$ are fully protected precursors of differently charged regions of the compounds of the invention.

In the following step of the process, the compounds such as (f) and (g) are converted into glycosidic-linkage donors and are coupled to the non-reducing terminal unit of fully protected precursors of Pe.

As has been mentioned above, the oligosaccharide of the non-reducing terminal unit of a glycosidic-linkage-donor polysaccharide (g) may constitute a part of Pe, in the case where (g) is coupled to the non-reducing terminal unit of a fully protected oligosaccharide which is the precursor of the residue of the structure of Pe.

The compounds of the invention are obtained from their fully protected polysaccharide precursors using the following sequence of reactions:

the alcohol functions which need to be converted into a sulpho group and the carboxylic acids are deprotected by removal of the Tn groups used to protect them during the development of the skeleton, then the sulpho groups are subsequently introduced.

The compounds of the invention may, naturally, be prepared using various strategies known to those skilled in the art of oligosaccharide synthesis.

The process described above is the preferred process of the invention. However, the compounds of formula (I) may be prepared by other well-known methods of sugar chemistry described, for example, in Monosaccharides, Their chemistry and their roles in natural products, P. M. Collins and R. J. Ferrier, J. Wiley & sons, 1995 and in G. J. Boons, Tetrahedron, 1996, 52, 1095–1121.

The precursor of the part of the pentasaccharide Pe when W represents an oxygen atom and $R_1a$ is $R_1$ is prepared according to oligosaccharide synthesis methods and particularly according to the methods described in patents EP 84,999, EP 301,618, EP 454,220 and EP 529,715 and in patent applications EP 93204769 and EP 94202470. When complete protection is carried out, it is possible, using suitable protecting groups, to obtain a free hydroxyl group on position 4 of the non-reducing terminal unit (D). The fully protected precursor of Pe is then coupled to this position using the known methods of oligosaccharide synthesis.

The pentasaccharide Pe in which W represents a carbon atom and $R_1a$ is $R_1$, of formula:

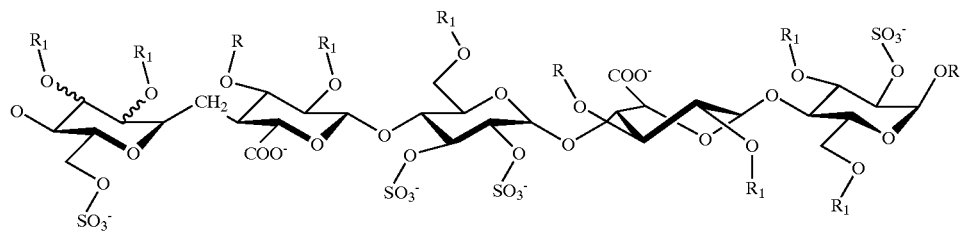
(II)

in which R and $R_1$ are as defined for (I), is obtained from the synthon of formula:

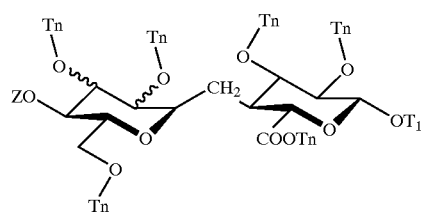
(II.1)

in which $T_1$ and $T_n$ which may be identical or different, represent a temporary, semi-permanent or permanent substituent, Z is a protecting group for a hydroxyl function which is itself obtained by a synthesis carried out by means of a radical reaction between a free-radical-generating monosaccharide and a monosaccharide containing a double bond, the C-disaccharide thus obtained then being converted into synthon (II.1) according to the standard methods described above according to C. van Boeckel and M. Petitou.

The synthon of formula (II.1), which is particularly useful in the synthesis of the compounds (II), is of formula:

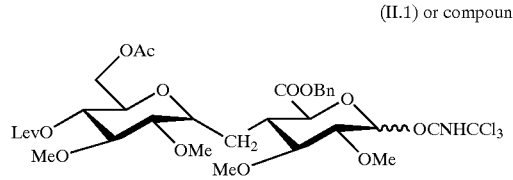
(II.1) or compound 90

This synthon is prepared according to the reaction scheme described in Scheme 22 below.

The pentasaccharide Pe which features a substituent $R_1a$ which constitutes an L-iduronic acid unit of locked configuration, of formula:

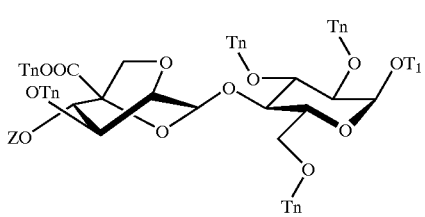
(III.1)

in which $T_1$ and $T_n$, which may be identical or different, represent a temporary, semi-permanent or permanent substituent, Z is a protecting group for a hydroxyl function which is itself obtained by a synthesis carried out according to the methods described in the literature M. K. Gurjar et al., Tetrahedron letters, 1995, 36, 11, 1937–1940, 1933–1936 and 1994, 35, 14, 2241–2244.

The synthon of formula (III.1) which is particularly useful for synthesizing the compounds (III) is of formula:

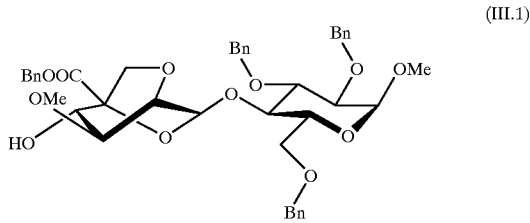
(III.1)

This synthon is prepared according to the reaction scheme described in Scheme 34 below.

The intermediates (II.1) and (III.1) are novel intermediates which are particularly useful for preparing the compounds (I) according to the invention.

The pentasaccharides Pe may thus be obtained from these disaccharide synthons (II.1) or (III.1) in the way described in the publication by C.A.A. van Boeckel and M. Petitou, Angew. Chem. Int. Ed. Engl. mentioned above.

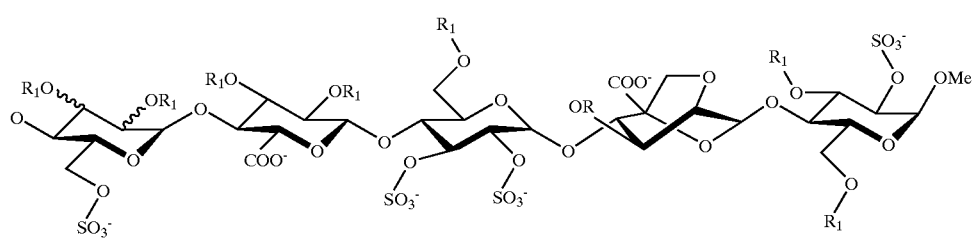
(III)

in which R and $R_1$ are as defined for (I) and W represents an oxygen atom, are obtained from the synthon of formula:

The term semi-permanent groups used above is understood to refer to the groups which can be removed firstly after the glycosylation reactions when the carbohydrate skeleton contains the desired number of units, without removing or adversely affecting the other groups present, thereby allowing the introduction of desired functional groups into the positions they occupy.

The permanent groups are groups capable of maintaining the protection of the OH functions during introduction of the functional groups in place of the semi-permanent groups.

These groups are chosen from those which are compatible with the functional groups introduced after removal of the semi-permanent groups. They are, moreover, groups which are inert towards the reactions carried out to install these functional groups and which may be removed without these functional groups being adversely affected.

According to the invention, the permanent groups are preferably $(C_1-C_6)$alkyl groups. Examples of semi-permanent and/or temporary groups which may be mentioned are benzyl and acetyl, levulinyl, p-methoxybenzyl groups, etc.

The substituents in position 3 of the uronic units of the target compound may already be present in the starting synthons, along with the substituent $R_1$.

The protecting groups used in the process for preparing the compounds (I) are those commonly used in sugar chemistry, for example in Protective Groups in Organic Synthesis, T W Greene, John Wiley & sons, New York, 1981.

The protecting groups are advantageously chosen, for example, from acetyl, halomethyl, benzoyl, levulinyl, benzyl, substituted benzyl, optionally substituted trityl, tetrahydropyranyl, allyl, pentenyl, tert-butyldimethylsilyl (tBDMS) or trimethylsilylethyl groups (etc.).

The activating groups are those conventionally used in sugar chemistry, for example according to G. J. Boons, Tetrahedron, 1996, 52, 1095–1121. These activating groups are chosen, for example, from imidates, thioglycosides, pentenylglycosides, xanthates, phosphites and halides.

The process described above makes it possible to obtain the compounds of the invention in the form of salts. In order to obtain the corresponding acids, the compounds of the invention in the form of salts are placed in contact with a cation-exchange resin in acidic form.

The compounds of the invention in acidic form may then be neutralized with a base in order to obtain a desired salt.

For the preparation of the salts of the compounds of formula (I), any organic or inorganic base may be used, giving, with the compounds of formula (I), pharmaceutically acceptable salts.

Sodium hydroxide, potassium hydroxide, calcium hydroxide or magnesium hydroxide is preferably used as base. The sodium and calcium salts of the compounds of formula (I) are the preferred salts.

In step (a) of the process, the protecting groups used are those usually used by those skilled in the art of sugar chemistry, for example according to EP 84,999 or alternatively according to Protective Groups in Organic Synthesis, T W Greene, J. Wiley & sons, 1995.

The compounds (I) thus obtained may optionally be salified.

The compounds of formula (I) above also comprise those in which one or more hydrogen or carbon atoms have been replaced with their radioactive isotope, for example tritium or carbon-14. Such labelled compounds are useful in pharmacokinetic, metabolism or research studies, and in biochemical tests as ligands.

The compounds according to the invention formed the subject of biochemical and pharmacological studies which showed that they possess very advantageous properties.

The compounds of the present invention which bind selectively to AT III with an affinity equal to or greater than that of heparin possess the anticoagulant and antithrombotic properties of heparin.

The overall antithrombotic activity of the products of formula (I) was evaluated intravenously or subcutaneously in rats, in a model of venous stasis and induction by thromboplastin, according to the method described by J. Reyers et al. in Thrombosis Research, 1980, 18, 669–674 as well as in a model of arterial thrombosis consisting of a shunt implanted between the carotid artery and the jugular vein of rats, as described by Umetsu et al. Thromb. Haemost., 1978, 39, 74–83. In these two experimental models, the $ED_{50}$ of the compounds of the invention is at least of the same order as or less than that of the other synthetic heparinoids already known ($ED_{50}$ between 5 and 500 µg/kg). The compounds of the invention thus have a specificity of action and an anticoagulant and antithrombotic activity which are particularly advantageous.

By virtue of their biochemical and pharmaceutical activity, the compounds of the present invention are very advantageous medicines. Their toxicity is entirely compatible with this use. They are also very stable and are thus particularly suitable for constituting the active principle of pharmaceutical specialty products.

Furthermore, the compounds of the invention are not neutralized by large doses of cationic platelet proteins such as platelet factor 4 (PF4) released during activation of these proteins in the process of thrombosis. The compounds of the invention are thus particularly advantageous for the treatment and prevention of thrombosis of arterial or venous origin.

They may be used in various pathologies which are consecutive to a modification of the haemostasis of the coagulation system, which appears in particular during disorders of the cardiovascular and cerebrovascular system, for instance thromboembolic disorders associated with atherosclerosis and with diabetes, such as unstable angina, cerebral attacks, restenosis after angioplasty, endarterectomy and the installation of endovascular prostheses; or thromboembolic disorders associated with rethrombosis after thrombolysis, with infarction, with dementia of ischaemic origin, with peripheral arterial diseases, with haemodialysis and with auricular fibrillations or alternatively during the use of vascular prostheses of aortocoronary bridges. These products may moreover be used for the treatment or prevention of thromboembolic pathologies of venous origin such as pulmonary embolism. They may be used for preventing or treating thrombotic complications which appear during surgical interventions or together with other pathologies such as cancer and bacterial or viral infections. When they are used during the installation of prostheses, the compounds of the present invention may coat the prostheses and thus make them haemocompatible. In particular, they may be bound to intravascular prostheses (stents). In this case, they may optionally be chemically modified by introduction of a suitable arm onto the reducing or non-reducing end, as described in EP 649,854.

The compounds of the present invention may also be used as adjuvants during endarterectomy performed with small porous balloons.

The compounds of the invention are very stable and are thus particularly suitable for constituting the active principle of medicines.

According to another of its aspects, the subject of the present invention is thus a pharmaceutical composition containing, as active principle, a synthetic polysaccharide as defined above.

The invention preferably relates to pharmaceutical compositions containing, as active principle, a compound of formula (I), (I.1), (I.2) or (I.3) or one of its pharmaceutically acceptable salts, optionally in combination with one or more inert and suitable excipients.

In each dosage unit, the active principle is present in amounts adapted to the daily doses envisaged. In general, each dosage unit is conveniently adjusted according to the dosage and type of administration planned, for example tablets, gelatin capsules and the like, sachets, ampules, syrups and the like, drops and transdermal or transmucous patches, such that one dosage unit contains from 0.1 to 100 mg of active principle, preferably 0.5 to 50 mg.

The compounds according to the invention may also be used in combination with another active principle which is useful for the desired therapy such as, for example, antithrombotic agents, anticoagulants or platelet-antiaggregating agents, for example such as dipyridamole, aspirin, ticlopidine, clopidogrel or antagonists of the glycoprotein IIb/IIIa complex.

The pharmaceutical compositions are formulated for administration into mammals, including man, for the treatment of the abovementioned diseases.

The pharmaceutical compositions thus obtained are advantageously in various forms such as, for example, injectable or drinkable solutions, tablets, coated tablets or gelatin capsules. The injectable solutions are the preferred pharmaceutical forms. The pharmaceutical compositions of the present invention are useful in particular for the preventive or curative treatment of disorders of the vascular wall, such as atherosclerosis, the hypercoagulability states observed, for example, after surgical operations, tumour development or deregulation of coagulation, which are induced by bacterial, viral or enzymatic activators. The dosage may vary widely as a function of the age, weight and state of health of the patient, the nature and severity of the complaint and the route of administration. This dosage comprises the administration of one or more doses of from 0.1 mg to 100 mg per day approximately, preferably from 0.5 to 50 mg per day approximately, intramuscularly or subcutaneously, in continuous administrations or administrations at regular intervals.

The subject of the present invention is thus also pharmaceutical compositions which contain, as active principle, one of the above compounds optionally combined with another active principle. These compositions are prepared so as to be able to be administered via the digestive or parenteral route.

In the pharmaceutical compositions of the present invention for oral, sublingual, subcutaneous, intramuscular, intravenous, transdermal, transmucous, local or rectal administration, the active ingredient may be administered in unit forms of administration, mixed with standard pharmaceutical vehicles, to animals and to man. The appropriate unit forms of administration comprise oral forms such as tablets, gelatin capsules, powders, granules and oral suspensions or solutions, sublingual and buccal administration forms, subcutaneous, intramuscular, intravenous, intranasal or intraoccular administration forms and rectal administration forms.

When a solid composition in tablet form is prepared, the main active ingredient is mixed with a pharmaceutical vehicle such as gelatin, starch, lactose, magnesium stearate, talc, gum arabic or the like. The tablets may be coated with sucrose or other suitable materials or alternatively they may be treated such that they have a sustained or delayed activity and so that they release a predetermined amount of active principle continuously.

A preparation in gelatin capsules is obtained by mixing the active ingredient with a diluent and pouring the mixture obtained into soft or hard gelatin capsules.

The water-dispersible powders or granules may contain the active ingredient mixed with dispersing agents or wetting agents, or suspending agents, for instance polyvinylpyrrolidone, as well as with sweeteners or flavour enhancers.

For rectal administration, use is made of suppositories which are prepared with binders that melt at rectal temperature, for example cocoa butter or polyethylene glycols.

For parenteral, intranasal or intraoccular administration, sterile, injectable solutions, isotonic saline solutions or aqueous suspensions which contain pharmacologically compatible dispersing agents and/or wetting agents, for example propylene glycol or butylene glycol, are used.

For transmucous administration, the active principle may be formulated in the presence of a promoter such as a bile salt or in the presence of a hydrophilic polymer such as, for example, hydroxypropylcellulose, hydroxypropylmethylcelluose, hydroxyethylcellulose, ethylcellulose, carboxymethylcellulose, dextran, polyvinylpyrrolidone, pectins, starches, gelatin, casein, acrylic acids, acrylic esters and their copolymers, vinyl polymers or copolymers, vinyl alcohols, alkoxypolymers, polyethylene oxide polymers and polyethers, or a mixture thereof.

The active principle may also be formulated in the form of microcapsules, optionally with one or more vehicles or additives.

The active principle may also be in the form of a complex with a cyclodextrin, for example $\alpha$-, $\beta$- or $\gamma$-cyclodextrin, 2-hydroxypropyl-$\beta$-cyclodextrin or methyl-$\beta$-cyclodextrin.

The active principle may also be released by a small balloon containing it or by an endovascular expander introduced into blood vessels. The pharmacological efficacy of the active principle is thus not adversely affected.

Subcutaneous administration is the preferred route.

The following methods, preparations and schemes illustrate the synthesis of the various intermediates which are useful for obtaining the polysaccharides according to the invention.

The examples below also illustrate the invention without, however, limiting it.

The following abbreviations are used:
TBDMS: tert-butyldimethylsilyl; Lev: levulinyl; Bn: benzyl; Bz: benzoyl; TLC: thin-layer chromatography; Olm: trichloroacetimidyl; LSIMS: Liquid Secondary Ion Mass Spectrometry; ESIMS: Electron Spray Ionization Mass. Spectrometry; TMS: trimethylsilyl; TSP: sodium trimethylsilyltetradeuteriopropionate; Tf: triflate; MS: molecular sieves; All: allyl; PMB: p-methoxybenzyl; SE: trimethylsilylethyl.

Dowex®, Sephadex®, Chelex® and Toyopearl® are registered trademarks.

In the methods, the preparations and in the examples described below, general procedures relating to catalytic coupling of the imidates, cleavage of the levulinic esters, catalytic coupling of the thioglycosides, saponification, methylation and selective deprotection of the p-methoxybenzyl group, the deprotection and sulphation of the oligo- and polysaccharides by hydrogenolysis of the benzyl ethers or of the esters, saponification of the esters or sulphations may be performed applying the general methods below to the appropriate intermediates.

GENERAL METHODS

METHOD 1

Coupling to Imidates Catalysed by Tert-butyldimethylsilyl Triflate

A solution of tert-butyldimethylsilyl triflate in dichloromethane (1M, 0.2 mol/mol of imidate) is added, under argon and at −20° C., to a solution of the imidate and the glycosyl acceptor in dichloromethane (17.5 ml/mmol) in the presence of 4 Å molecular sieves. After 10–20 minutes (TLC), solid sodium hydrogen carbonate is added. The solution is filtered, washed with water, dried and evaporated to dryness.

METHOD 2

Cleavage of the Levulinic Group

The compound to be deprotected is dissolved in a 2/1 ethanol/toluene mixture (42 ml/mmol) and hydrazine acetate (5 mol/mol) is added. The mixture is left stirring for 15–30 minutes (TLC) and concentrated.

METHOD 3

Coupling to the Thioglycosides Catalysed by N-Iodosuccinimide/Silver Triflate

The thioglycoside and the glycosyl acceptor are dissolved in anhydrous toluene (18 ml/mmol of thioglycoside) in the presence of 4 Å molecular sieves in a round-bottomed flask made of inactinic glass. The mixture is stirred for 1 hour at room temperature. It is cooled to 0° C. and N-iodosuccinimide (3 mol/mol of thioglycoside) is added, followed by silver triflate (0.28 mol/mol of thioglycoside). After 10–15 minutes (TLC), solid sodium hydrogen carbonate is added. After filtration, the solution is washed with aqueous 1M sodium thiosulphate solution, water, dried and evaporated.

METHOD 4

Saponification, Methylation and Selective Deprotection of the p-Methoxybenzyl Group Saponification of the esters. The compound to be saponified is dissolved in a 1/1 dichloromethane/methanol mixture (4 ml/mmol). Sodium methoxide is added and the mixture is stirred for 20 minutes and neutralized with a 50 H$^-$ Dowex® resin. The solution is concentrated and this compound is used in the following step without purification.

Methylation. Sodium hydride is added portionwise, at 0° C., to a mixture of the above crude product and methyl iodide in N,N-dimethylformamide (7 ml/mmol). After complete reaction, the mixture is poured into water and extracted with ethyl acetate. The organic phases are washed with water, dried and evaporated to dryness.

Cleavage of the p-methoxybenzyl. The above crude compound is dissolved in a 9/1 acetonitrile/water mixture (20 ml/mmol). At 0° C., ammonium cerium nitrate (0.5 mol/mol) is added. The reaction mixture is stirred for 2 hours (monitored by TLC), saturated sodium hydrogen carbonate solution is added and the mixture is extracted with ethyl acetate, dried and evaporated.

METHOD 5

Deprotection and Sulphation of the Oligo- and Polysaccharides

Hydrogenolysis of the benzyl ethers and benzyl esters. A solution of the compound in glacial acetic acid is left stirring for 6–12 hours (TLC) under a hydrogen atmosphere (40 bar) in the presence of 5% Pd/C catalyst (twice the mass of the compound). After filtration, the product is used directly in the following step.

Saponification of the esters. Aqueous 5 M sodium hydroxide solution (in an amount such that the concentration of sodium hydroxide is 0.5 M at the end of the addition) is added to a solution of an ester in methanol (150 ml/mmol). After 2–5 hours, water is introduced and the mixture is passed through a column of Sephadex® G-25 gel (1.6×115 cm) eluted with water. The eluate is concentrated, passed through a Dowex® 50 H$^-$ column (2 ml) and freeze-dried. At this stage, it is confirmed by $^1$H NMR that all the protecting groups have been removed. If necessary, the product is subjected to a further hydrogenation and/or saponification.

Sulphation. Triethylamine/sulphur trioxide complex (5 mol/mol of hydroxyl function) is added to a solution of the compound to be sulphated in dimethylformamide (5 mg/ml). After one day at 55C, the solution is placed at the top of a Sephadex® G-25 column (1.6×115 cm), eluted with 0.2 M sodium chloride. The fractions containing the product are concentrated and desalified using the same column eluted with water. The final compound is obtained after

SCHEME 3

Synthesis of monosaccharide 6 and 9

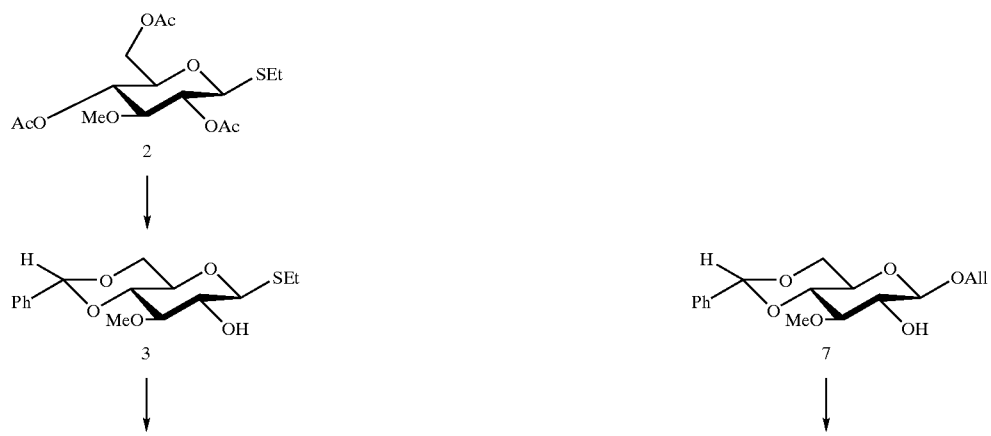

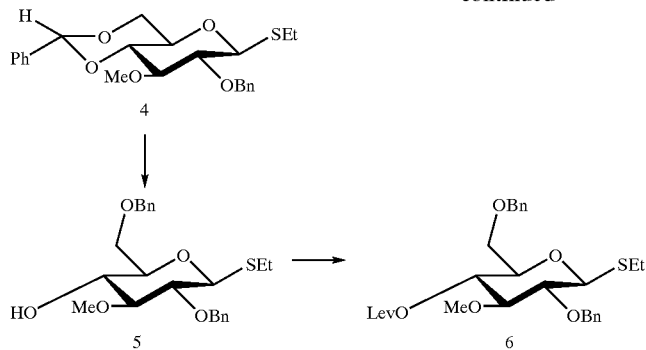
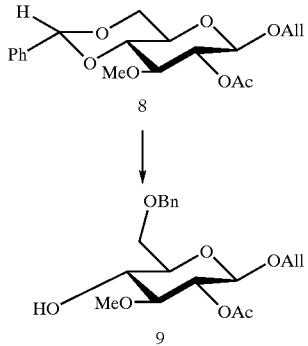

PREPARATION 1

Ethyl 2,4,6-Tri-O-acetyl-3-O-methyl-1-thio-β-D-glucopyranoside (2)

1,2,4,6-Tetra-O-acetyl-3-O-methyl-β-D-glucopyranose 1 (69 g, 0.19 mmol), (B. Helferich et al., J. prakt. Chem., 132, 321 (1932)) is dissolved in toluene (580 ml). Ethanethiol (28 ml, 0.38 mmol) is added, followed by dropwise addition of a solution of trifluoroborane diethyl etherate (1 M in toluene, 190 ml). The mixture is left stirring for 1.5 hours (TLC), solid sodium hydrogen carbonate is introduced and the mixture is filtered, washed with water, dried and concentrated. Chromatography on a column of silica (3/1 cyclohexane/ethyl acetate) gives 2 (37 g, 54%) $[\alpha]_D$–26 (c=1. dichloromethane). $^1$H NMR (CDCl$_3$). δ 5.05–4.96 (m, 2H, H-2, H-4), 4.39, (d, 1H, J=9.5 Hz, H-1), 4.18–4.12 (m, 2H, H-6, H-6'), 3.60 (m, 1H, H-5), 3.50 (dd, 1H, J=9.3 Hz, H-3), 3.41 (s, 3H, OCH$_3$), 2.65–2.53 (m, 2H, SCH$_2$CH$_3$), 2.12, 2.11, 2.09 (3s, 9H, 3 Ac), 1.25 (t, 1H, SCH$_2$CH$_3$)

PREPARATION 2

Ethyl 4,6-O-Benzylidene-3-O-methyl-1-thio-β-D-glucopyranoside (3)

Compound 2 (37 g, 0.1 mmol) is dissolved in a 1/2 mixture of methanol and dichloromethane (1.5 l). 2 M sodium methoxide solution (150 ml) is added. After 0.5 hour at room temperature, the mixture is neutralized with Dowex® 50 (H$^+$) resin, filtered and concentrated.

The above crude compound is dissolved in anhydrous acetonitrile (1 l) and α,α-dimethoxytoluene (30 ml, 0.2 mol) and camphorsulphonic acid (2.3 g, 10 mmol) are added. The mixture is left stirring for 1.5 hours (TLC), triethylamine (1.4 ml) is added and the mixture is concentrated. The residue obtained is precipitated in ethyl ether and gives 3 (27 g, 81%). $[\alpha]_D$–60 (c=1.63, dichloromethane). $^1$H NMR (CDCl$_3$) δ 7.51–7.34 (m, 5H, Ph), 5.55 (s, 1H, C$_6$H$_5$CH), 4.56 (d, 1H, J=9.2Hz, H-1), 2.75 (m, 2H, SCH$_2$CH$_3$), 1.32 (t, 3H, SCH$_2$CH$_3$).

Anal. Calculated for C$_{16}$H$_{22}$O$_5$S (326.41): C, 58.58; H, 6.79; S, 9.82. Found: C, 58.99; H, 6.74; S, 9.75.

PREPARATION 3

Ethyl 2-O-Benzyl-4,6-O-benzylidene-3-O-methyl-1-thio-β-D-glucopyranoside (4)

Sodium hydride (2.00 g, 83.3 mnol) is added, at 0° C., to a solution of 3 (23 g, 71.0 mmol) and benzyl bromide (11 ml, 93.0 mmol) in N,N-dimethylformamide (200 ml). The mixture is left stirring for 2 hours (TLC), methanol is added and the reaction mixture is poured into water. It is extracted with ethyl acetate, washed with water, dried and concentrated. The residue is precipitated in ethyl ether in order to obtain 4 (18.8 g, 63%). m.p. 123° C. $[\alpha]_D$–35 (c=0.63, dichloromethane). $^1$H NMR (CDCl$_3$) δ 7.50–7.25 (m, 10H, 2Ph), 5.55 (s, 1H, C$_6$H$_5$CH), 4.54 (d, 1H, J=9.7 Hz, H-1), 4.34 (m, 1H, H-6), 3.75 (t, 1H, J=10.2 Hz, H-6'), 3.65 (s, 3H, OCH$_3$), 3.60–3.33 (m, 4H, H-5, H-4, H-3, H-2), 2.75 (m, 2H, SCH$_2$CH$_3$), 1.32 (t, 3H, SCH$_2$CH$_3$).

Anal. Calculated for C$_{23}$H$_{28}$O$_5$S (416.54): C, 66.32, H, 6.78; S, 7.70. Found: C, 66.25; H, 7.28; S, 7.54.

PREPARATION 4

Ethyl 2,6-Di-O-benzyl-3-O-methyl-1-thio-β-D-glucopyranoside (5)

A solution of trifluoroacetic anhydride (0.65 ml, 4.50 mmol) in trifluoroacetic acid (16 ml, 0.21 mmol) is added, under argon, to a solution of 4 (28.8 g, 69.0 mmol) and triethylsilane (33 ml, 0.21 mmol) in dichloromethane (120 ml). The mixture is left stirring for 2 hours and diluted with ethyl acetate and aqueous 1 M sodium hydroxide solution is added to pH 9. The mixture is extracted with ethyl acetate, washed with water, dried and evaporated to dryness. The residue is purified on a column of silica (3/1 and then 2/1 cyclohexane/ethyl acetate) in order to obtain 5 (17.4 g, 60%). $[\alpha]_D$–47 (c=1, dichloromethane). $^1$H NMR (CDCl$_3$) δ 7.45–7.25 (m, 10H, 2Ph), 4.47 (d, 1H, J=9.3 Hz, H-1), 3.66 (s, 3H, OCH$_3$), 3.61–3.40 (m, 2H, H-4 and H-5), 3.36–3.19 (m, 2H, H-2 and H-3), 2.73 (m, 2H, SCH$_2$CH$_3$), 1.31 (t, 3H, SCH$_2$CH$_3$).

Anal. Calculated for C$_{23}$H$_{30}$O$_5$S (418.55): C, 66.00, H, 7.22; S7.66. Found C, 65.62; H, 7.28; S, 7.21.

PREPARATION 5

Ethyl 2,6-O-Di-benzyl-4-O-levulinyl-3-O-methyl-1-thio-β-D-glucopyranoside (6)

Compound 5 (17.3 g, 41.4 mmol) is dissolved in anhydrous dioxane (400 ml). Levulinic acid (9.60 g, 83.0 mmol), 1-(3-dimethylaminopropyl)-3-ethylcarbodiimide (16 g, 86 mmol) and 4-dimethylaminopyridine (1 g, 8.3 mmol) are added. The mixture is left stirring for 4 hours, extracted with ethyl acetate, washed successively with aqueous 5% potassium hydrogen sulphate solution, with water, with saturated aqueous sodium hydrogen carbonate solution, with water, dried and concentrated. The residue is purified on a column of silica (6/1 toluene/ethyl acetate) in order to obtain pure 6 (19.9 g, 93%). $[\alpha]_D$–5 (c=1.46, dichloromethane). LSIMS, positive mode: m/z thioglycerol+NaCl, 539 (M+Na)$^+$; thioglycerol+KF, 555 (M+K)$^+$. $^1$H NMR (CDCl$_3$) δ 7.40–7.20 (m, 10H, 2Ph), 4.92 (m, 1H, H-4), 2.8–2.4 (m, 6H, SCH$_2$CH$_3$ and O(C:O)CH$_2$CH$_2$(C:O)CH$_3$); 2.16 (s, 3H, O(C:O)CH$_2$CH$_2$(C:O)CH$_3$), 1.32 (t, 1H, J=7.3 Hz, SCH$_2$CH$_3$).

Anal. Calculated for C$_{28}$H$_{36}$O$_7$S (516.65): C, 65.09, H, 7.02; S, 6.21. Found: C, 65,30; H, 7.03; S, 5.75.

PREPARATION 6

Allyl 4,6-O-Bentylidene-3-O-methyl-β-D-glucopyranoside (7)

Trifluoromethanesulphonic acid (1.10 ml, 0.012 mol) is added to a suspension of commercial 3-O-methylglucose (135 g, 0.7 mol) in allyl alcohol (1 l). The mixture is heated at 120° C. for 2 hours. It is neutralized by addition of triethylamine (2 ml) and evaporated to dryness. α,α-Dimethoxytoluene (136 ml, 0.9 mol) and camphorsulphonic acid (25 g, 0.13 mmol) are added to the above crude compound dissolved in N,N-dimethylformamide (2 l). The mixture is heated at 80° C. for 1 hour under vacuum. It is neutralized by addition of triethylamine (21 ml) and extracted with ethyl acetate, washed with water, dried and concentrated in order to obtain a solid α/β mixture=3/2, (144 g, 57%). This mixture is recrystallized from ethanol in order to obtain pure 7-α (60 g, 26%). Chromatography of part of the mother liquors on a column of silica (3/1 cyclohexane/ethyl acetate) gives pure 7-β (7.6 g), 7-α/β (6.8 g) and pure 7-α (1.4 g).

Compound 7-β: [α]$_D$–43 (c=1, dichloromethane) m.p.: 131° C. $^1$H NMR (CDCl$_3$) δ 7.50–7.26 (m, 5H, Ph), 6.01–5.90 (m, 1H, OCH$_2$(CH:CH$_2$)), 5.55 (s, 1H, C$_6$H$_5$CH), 5.38–5.32 (m, 2H, OCH$_2$(CH:CH$_2$) ), 4.47 (d, 1H, J=7.5 Hz, H-1), 4.42–4.32 (m, 2H, H-6' and OCH$_2$(CH:CH$_2$)), 4.21→4.15 (m, 1H, OCH$_2$(CH:CH$_2$)), 3.80 (dd, 1H, J=10.2 Hz, H-6), 3.67 (s, 3H, OCH$_3$).

Anal. Calculated for C$_{17}$H$_{22}$O$_6$ (322.36): C, 63.34; H, 6.88. Found: C, 63.23; H, 7.12.

PREPARATION 7

Allyl 2-O-Acetyl-4,6-O-benzylidene-3-b-methyl-β-D-gluco-pyranoside (8)

7 (11.5 g, 35.7 mmol) is dissolved in dichloro-methane (100 ml) and acetic anhydride (4.0 ml, 42.8 mmol), triethylamine (6.40 ml, 46.4 mmol) and 4-dimethylaminopyridine (440 mg, 3.60 mmol) are added. The mixture is left stirring for 2 hours (TLC), washed successively with aqueous 5% potassium hydrogen sulphate solution, with water, with saturated aqueous sodium hydrogen carbonate solution, with water, dried and evaporated until a solid 8 (12.3 g, 95%) is obtained. m.p. 115° C. [α]$_D$–68 (c=1, dichloro-methane). LSIMS, positive mode: m/z thioglycerol+NaCl, 387 (M+Na)$^+$; thioglycerol+KF, 403 (M+K)$^+$. $^1$H NMR (CDCl$_3$) δ 7.51–7.34 (m, 5H, Ph), 5.98–5.78 (m, 1H, OCH$_2$(CH:CH$_2$)), 5.56 (s, 1H, C$_6$H$_5$C$_6$H$_5$CH), 5.32–5.17 (m, 2H, OCH$_2$(CH:CH$_2$)), 4.99 (dd, J=8 Hz, 1H, H-2), 4.55 (d, J=7.9 Hz, 1H, H-1), 4.39–4.29 (m, 2H, H-6 and OCH$_2$(CH:CH$_2$)), 4.14–4.04 (m, 1H, OCH$_2$(CH:CH$_2$)) 3.82 (t, J=10.2 Hz, 1H, H-6'), 3.60 (s, 3H, OCH$_3$), 2.12 (s, 3H, Ac).

Anal. Calculated for C$_{19}$H$_{24}$O$_7$ (366.39): C, 62.63; H, 6.64. Found: C, 62.63; H, 6.64.

PREPARATION 8

Allyl 2-O-Acetyl-6-O-benzyl-3-O-methyl-β-D-glucopyrano-side (9)

A solution of trifluoroacetic anhydride (306 μl, 2.10 mmol) in trifluoroacetic acid (10 ml) is added, at 0° C., to a solution of 8 (12.0 g, 33.3 mmol) and triethylsilane (21.3 ml, 133 mmol) in anhydrous dichloromethane (50 ml). The mixture is left stirring for 4 hours (TLC), diluted with ethyl acetate and aqueous 1M sodium hydroxide solution is added to pH 9. The mixture is extracted with ethyl acetate, washed with water, dried and concentrated. The residue is purified on a column of silica (8/5 cyclohexane/acetone) to give pure 9 (10 g, 82%). [α]$_D$–40 (c=1.06, dichloromethane). $^1$H NMR (CDCl$_3$) δ 7.35–7.28 (m, 5H, Ph), 5.87–5.79 (m, 1H, OCH$_2$(CH:CH$_2$)), 5.28–5.14 (m, 2H, OCH$_2$(CH:CH$_2$)), 4.43 (d, 1H, J=7.9 Hz, H-1), 4.41–4.28 (m, 1H, OCH$_2$(CH:CH$_2$)), 4.10–4.02 (m, 1H, OCH$_2$(CH:CH$_2$), 3.77–3.75 (m, 2H, H-6 and H-6'), 3.51 (s, 3H, OCH$_3$), 3.30 (dd, 1H, J=8.9 Hz, H-3), 2.8 (d, 1H, OH).

Anal. Calculated for C$_{19}$H$_{26}$O$_7$ (366.39): C, 62.28; H, 7.15. Found: C, 61.73: H. 7.19.

SCHEME 4

Synthesis of disaccharide 13 and 14

6 + 9

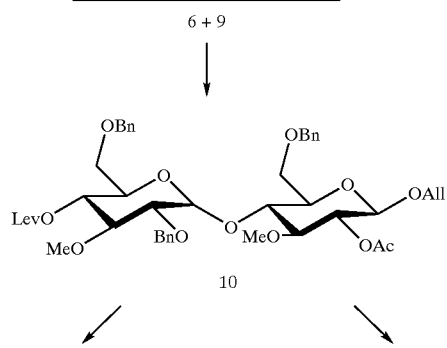

10

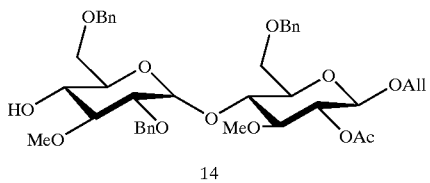

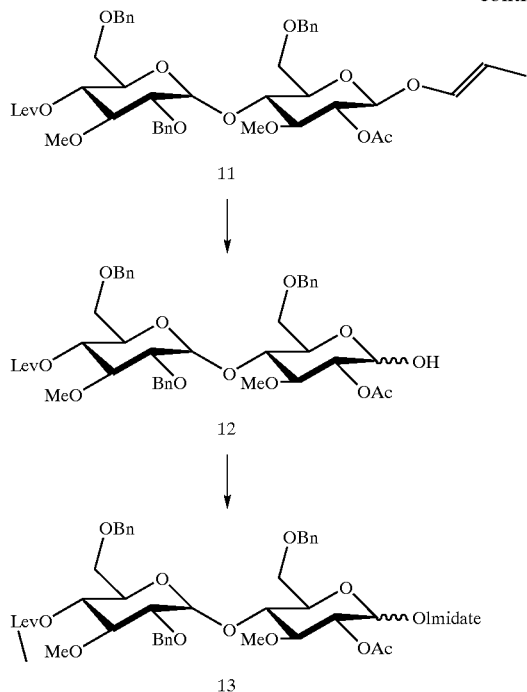

PREPARATION 9

Allyl 2-O-Acetyl-6-O-benzyl-3-O-methyl-4-O-(2,6-di-O-benzyl-4-O-levulinyl-3-O-methyl-α-D-glucopyranosyl)-β-D-glucopyranoside (10)

The thioglycoside 6 (17.4 g, 33.7 mmol) and the glycosyl acceptor 9 (10.3 g, 28.1 mmol) are dissolved in dichloroethane (150 ml). 4 Å molecular sieves are added and the mixture is left stirring for 1 hour. A solution of N-iodosuccinimide (8.30 g, 33.7 mmol) and trifluoromethanesulphonic acid (0.30 ml, 3.30 mmol) in a mixture of dichloroethane and ethyl ether (415 ml, 1:1) is added, at −20° C. and under an argon atmosphere. The mixture is left stirring for 10 minutes (TLC), sodium hydrogen carbonate is added and the mixture is filtered, washed successively with aqueous 1M sodium thiosulphate solution, with water, with saturated aqueous sodium hydrogen carbonate solution, with water, dried and concentrated. The residue is purified on a column of silica (11/1 dichloromethane/ethyl acetate) in order to give the pure disaccharide 10-α (11.7 g, 52%). $[\alpha]_D$+38 (c=1.01, dichloromethane). $^1$H NMR (CDCl$_3$) δ 7.35–7.23 (m, 15H, 3 Ph), 5.90–5.80 (m, 1H, OCH$_2$(CH:CH$_2$)), 5.47 (d, 1H, J=3.6 Hz, H-1'), 5.27–5.14 (m, 2H, OCH$_2$(CH:CH$_2$)), 5.05–4.90 (m, 2H, H-4' and H-2), 4.42 (d, 1H, J=7.6 Hz, H-1), 4.38–4.32 (m, 1H, OCH$_2$(CH:CH$_2$)), 4.15–4.0 (m, 1H, OCH$_2$(CH:CH$_2$)), 3.90 (dd, 1H, J=8.8 Hz, H-4), 3.54, 3.34 (2 s, 6H, 2 OCH$_3$), 2.75–2.40 (m, 4H, O(C:O)CH$_2$CH$_2$(C:O)CH$_3$), 2.16, 2.10 (2 s, 6H, Ac and O(C:O)CH$_2$CH$_2$(C:O)CH$_3$).

Anal. Calculated for C$_{45}$H$_{56}$O$_{14}$ (820.94): C, 65.84; H, 6.88. Found: C, 65.74; H, 6.90.

PREPARATION 10

Prop-1'-enyl-2-O-acetyl-6-O-benzyl-3-O-methyl-4-O-(2,6-di-O-benzyl-4-O-levulinyl-3-O-methyl-α-D-glucopyranosyl)-β-D-glucopyranoside (11)

1,5-Cyclooctadienebis[methyldiphenylphosphine]iridium hexafluorophosphate (5.80 mg, 0.70 μmol) is added to a solution of 10 (1.36 g, 1.66 mmol) in peroxide-free tetrahydrofuran (4.30 ml). The solution is degassed, placed under an argon atmosphere and hydrogen is introduced. The mixture is left stirring for 10 minutes (TLC) and evaporated. The residue is taken up in dichloromethane, washed with saturated aqueous sodium hydrogen carbonate solution, with water, dried and concentrated. The residue is purified on a column of silica (3/1 toluene/ethyl acetate) in order to obtain pure 11 (1.04 g, 76%). $[\alpha]_D$+47 (c=1.1, dichloromethane). LSIMS, positive mode: m/z thioglycerol+NaCl, 951 (M+Na)$^+$; thioglycerol+KF, 967 (M+K)$^+$. $^1$H NMR (CDCl$_3$) δ 7.34–7.23 (m, 15H, 3 Ph), 6.21–6.16 (m, 1H, O(CH:CH)CH$_3$), 5.45 (d, 1H, J=3.5 Hz, H-1'), 5.13–4.97 (m, 3H, H-4', H-2 and O(CH:CH)CH$_3$), 4.6 (d, 1H, J=7.55 Hz, H-1), 3.96 (dd, 1H, J=8.9 Hz, H-4'), 3.54, 3.34 (2 s, 6H, 2 OCH$_3$), 2.74–2.36 (m, 4H, O(C:O)CH$_2$CH$_2$(C:O)CH$_3$), 2.15, 2.08 (2s, 6H, Ac and O(C:O)CH$_2$CH$_2$(C:O)CH$_3$) 1.56–1.51 (dd, 3H, O(CH:CH)CH$_3$).

Anal. Calculated for C$_{45}$H$_{56}$O$_{14}$ (820.94): C, 65.84; H, 6.88. Found: C, 66.21; H, 6.92.

PREPARATION 11

2-O-Acetyl-6-O-benzyl-3-O-methyl-4-O-(2,6-di-O-benzyl-4-O-levulinyl-3-O-methyl-α-D-glucopyranosyl)-α,β-D-glucopyranose (12)

A solution of mercuric chloride (3.9 g, 14.3 mmol) in a mixture of acetone and water (26 ml, 5/1) is added dropwise to a solution of 11 (7.8 g, 9.53 mmol) and mercuric oxide in the same solvent (80 ml). The mixture is left stirring for 1 hour, filtered and concentrated. It is extracted with dichloromethane and the extracts are washed with saturated aqueous potassium iodide solution, with water, dried and concentrated. The residue is purified on a column of silica (10/1 and then 4/1 dichloromethane/acetone) in order to obtain 12 (6.70 g, 90%). $[\alpha]_D$+92 (c=1.37, dichloromethane). TLC, R$_F$ 0.31, 14/1 dichloromethane/acetone. $^1$H NMR (CDCl$_3$) δ

7.37–7.24 (m, 15H, 3 Ph), 5.46 (d, 1H, J=3.5 Hz, H-1'), 5.37 (d, J=3.6 Hz, H-1α), 4.58 (d, J=8 Hz, H-1β), 3.54, 3.39, 3.36 (3s, 6H, 2 OCH$_3$), 2.75–2.4 (m, 4H, O(C:O)CH$_2$CH$_2$(C:O)CH$_3$), 2.16, 2.15 (2s, 6H, Ac and O(C:O)CH$_2$CH$_2$(C:O)CH$_3$), 2.16, 2.15 (2s, 6H, Ac and O(C:O)CH$_2$CH$_2$(C:O)CH$_3$).

Anal. Calculated for C$_{42}$H$_{52}$O$_{14}$ (780.83); C, 64.60; H, 6.71. Found: C, 65.09; H, 6.82.

PREPARATION 12

2-O-Acetyl-6-O-benzyl-3-O-methyl-4-O-(2,6-di-O-benzyl-4-O-levulinyl-3-O-methyl-α-D-glucopyranosyl)-α,β-D-glucopyranose Trichloroacetimidate (13)

Compound 12 (5.00 g, 6.4 nmol) is dissolved in dichloromethane (50 ml) and trichloroacetonitrile (3.9 ml, 38.8 mmol) and potassium carbonate (1.6 g, 11.6 mmol) are added, under argon. The mixture is left stirring for 16 hours (TLC) and filtered. The filtrate is purified on a column of silica (8/1 and then 4/1 dichloromethane/acetone) in order to give a mixture (α,β=60/40) of imidates 13 (5.22 g, 87%). TLC, R$_F$ 0.66 and 0.51, 20/1 dichloromethane/acetone. $^1$H NMR (CDCl$_3$) δ 8.62–8.59 (2s, 1H, N:H-α and β), 7.37–7.23 (m, 15H, 3 Ph), 6.51 (d, J=3.7 Hz, H-1α), 5.81 (d, J=7.1 Hz, H-1β), 5.50 (d, 1H, J=3.5 Hz, H-1'), 3.55, 3.41, 3.37 (3s, 9H, 3 OCH$_3$), 2.75–2.40 (m, 4H, O(C:O)CH$_2$CH$_2$(C:O)CH$_3$), 2.16, 2.07, 2.04 (3s, 6H, Ac and (C:O)CH$_2$CH$_2$(C:O) CH$_3$).

Anal. Calculated for C$_{44}$H$_{52}$Cl$_3$NO14 (925.26): C, 57.12; H, 5.66; N, 1.51. Found: C, 57.31; H, 5.87; N, 1.55.

PREPARATION 13

Allyl 2-O-Acetyl-6-O-benzyl-3-O-methyl-4-O-(2,6-di-O-benzyl-3-O-methyl-α-D-glucopyranosyl)-β-D-glucopyranoside (14)

Compound 10 (3.11 g, 3.80 mmol) is treated according to Method 2 in order to give 14 (2.70 g, 97%). [α]$_D$+25 (c=1.7, dichloromethane). LSIMS, positive mode: rn/z thioglycerol+NaCl, 745 (M+Na)$^-$; thioglycerol+KF, 761 (M+K)$^+$. $^1$H NMR (CDCl$_3$) d 7.33–7.20 (m, 15H, 3 Ph), 5.87–5.78 (m, 1H, OCH (CH:CH$_2$)), 5.50 (d, 1H, J=3.5 Hz, H-1'), 5.30–5.17 (m, 2H, OCH$_2$(CH:CH$_2$)), 5.02 (dd, 1H, H-2), 4.43 (d, 1H, J=7.6 Hz, H-1), 4.34–4.28 (m, 1H, OCH$_2$(CH:CH$_2$)), 4.12–4.02 (m, 1H, OCH$_2$(CH:CH$_2$)), 3.63, 3.36 (2s, 6H, 2 OCH$_3$), 2.10 (s, 3H, Ac).

Anal. Calculated for C$_{40}$H$_{50}$O$_{12}$ (722.84); C, 66.47; H, 6.97. Found: C, 66.31; H, 7.24.

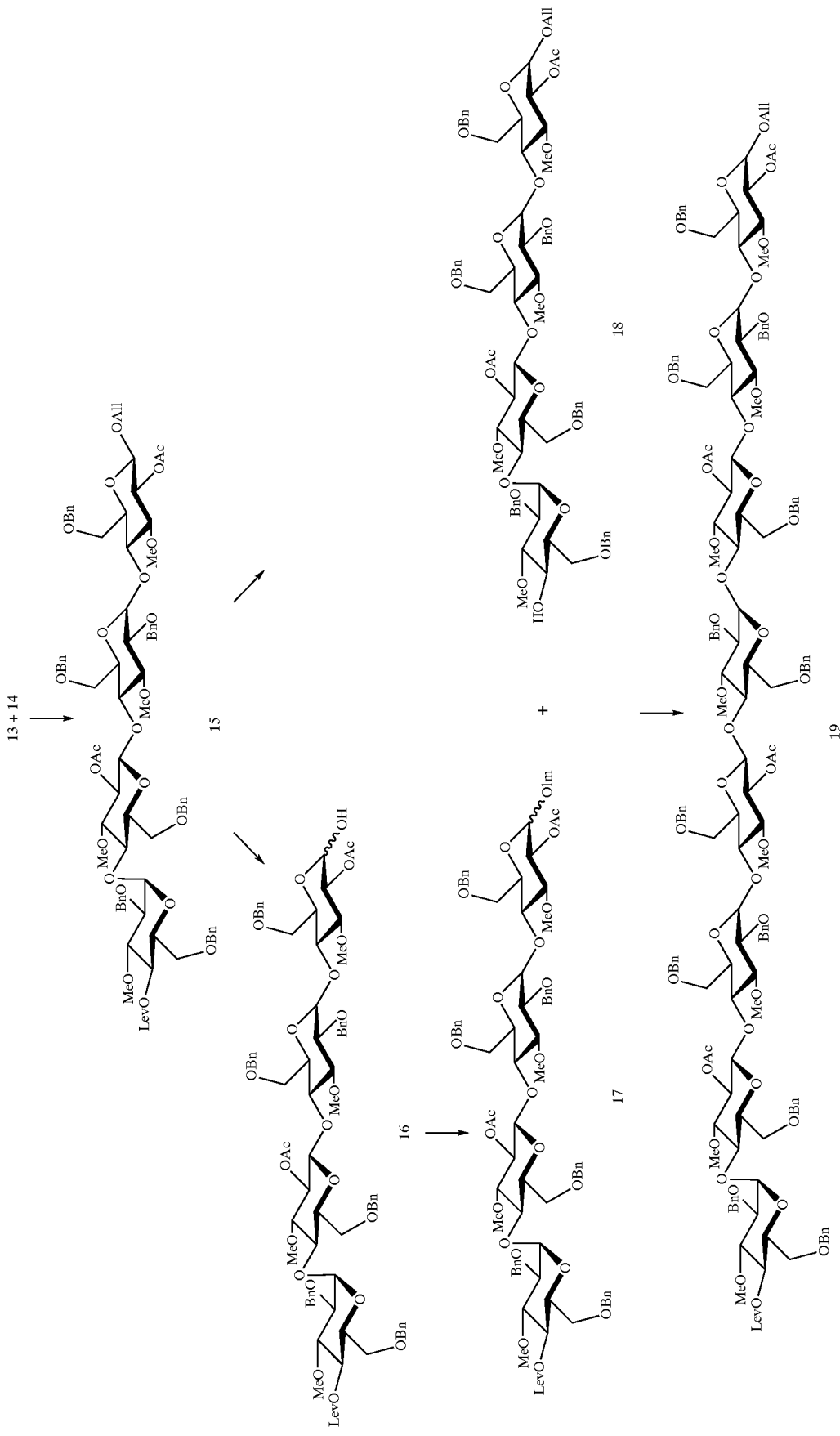

PREPARATION 14

Allyl O-(2,6-Di-O-benzyl-4-O-levulinyl-3-O-methyl-α-D-glucopyranosyl)-(1→4)-O-(2-O-acetyl-6-O-benzyl-3-O-methyl-β-D-glucopyranosyl)-(1→4)-O-(2,6-di-O-benzyl-3-O-methyl-α-D-glucopyranosyl)-(1→4)-2-O-acetyl-6-O-benzyl-3-O-methyl-β-D-glucopyranoside (15)

A mixture of the imidate 13 (4.22 g, 4.56 mmol) and the glycosyl acceptor 14 (2.63 g, 3.64 mmol) is treated according to Method 1. The product is purified on a column of silica (3/2 and then 1/1 toluene/ethyl ether) in order to give the tetrasaccharide 15 (4.31 g, 80%). $[\alpha]_D$+52 (c=0.66, dichloromethane). $^1$H NMR (CDCl$_3$) δ 7.35–7.23 (m, 30H, 6 Ph), 5.83–5.79 (m, 1H, OCH$_2$(CH:CH$_2$)), 5.47 (d, 2H, J=3.5 Hz, H-1''' and H-1'), 5.25–5.14 (m, 2H, OCH$_2$(CH:CH$_2$)), 4.38 (d, 1H, J=7.7 Hz, H-1''), 4.30 (d, 1H, J=8 Hz, H-1), 4.32–4.25 (m, 1H, OCH$_2$(CH:CH$_2$)), 4.08–4.02 (m, 1H OCH$_2$(CH:CH$_2$)), 3.56, 3.53, 3.34, 3.27 (4s, 12H, 4 OCH$_3$), 2.78–2.40 (m, 4H, O (C:O)CH$_2$CH$_2$(C:O)CH$_3$), 2.15, 2.09, 1.85 (3s, 9H, 2 Ac and O(C:O)CH$_2$CH$_2$(C:O)CH$_3$).

Anal. Calculated for $C_{82}H_{100}O_{25}$ (1485.7): C, 66.29; H, 6.78. Found: C, 66.10; H, 6.79.

PREPARATION 15

O-(2,6-Di-O-benzyl-4-O-levulinyl-3-O-methyl-α-D-glucopyranosyl)-(1→4)-O-(2-O-acetyl-6-O-benzyl-3-O-methyl-β-D-glucopyranosyl)-(1→4)-O-(2,6-di-O-beznyl-3-O-methyl-α-D-glucopyranosyl)-(1→4)-2-O-acetyl-6-O-benzyl-3-O-methyl-α,β-D-glucopyranose (16)

Compound 15 (2.30 g, 1.54 mmol) is treated as in Preparation 10. After 10 minutes, a solution of N-bromosuccinimide (0.30 g, 1.70 mmol) in dichloromethane (15 ml) and water (5.50 ml) is added to the reaction mixture. The mixture is left stirring for 5 minutes (TLC). It is diluted with dichloromethane, washed with saturated aqueous sodium hydrogen sulphate solution, with water, dried and concentrated. The residue is purified on a column of silica (3/2 toluene/ethyl acetate) in order to give pure 16 (1.57 g, 71% over the two steps). $[\alpha]_D$+69 (c=0.87, dichloronethane). $^1$H NMR (CDCl$_3$) δ 7.38–7.20 (m, 30H, 6 Ph), 5.47 (d, 1H, J=3.5 Hz, H-1''' and H-1'), 5.36 (d, 1H, J=3.5 Hz, H-1α), 4.55 (d, 1H, J=8 Hz, H-1), 4.36 (d, 1H, J=8 Hz, H-1''), 3.56, 3.54, 3.39, 3.36, 3.28 (5s, 9H, 3 OCH$_3$), 2.75–2.35 (m, 4H, O(C:O)CH$_2$CH$_2$(C:O)CH$_3$), 2.16, 2.13, 2.12, 1.86 (4s, 9H, 2 Ac and O(C:O)CH$_2$CH$_2$(C:O)CH$_3$).

PREPARATION 16

O-(2,6-Di-O-benzyl-4-O-levulinyl-3-O-methyl-α-D-glucopyranosyl)-(1→4)-O-(2-O-acetyl-6-O-benzyl-3-O-methyl-β-α-glucopyranosyl)-(1→4)-O-(2,6-di-O-benzyl-3-O-methyl-α-D-glucopyranosyl)-(1→4)-2-O-acetyl-6-O-benzyl-3-O-methyl-α,β-D-glucopyranose Trichloroacetimidate (17)

A mixture of 16 (1.5 g, 1.04 mmol), trichloroacetonitrile (0.63 ml, 6.22 mmol) and potassium carbonate (0.26 g, 1.87 mmol) in dichloromethane (15 ml) is left stirring for 16 hours at room temperature. The solution is filtered and concentrated. It is purified on a column of silica (4/1 toluene/acetone+1‰ of triethylamine) in order to give 17 (1.47 g, 89.6%), TLC, $R_F$ 0.5 7/2 toluene/acetone.

PREPARATION 17

Allyl O-(2,6-di-O-Benzyl-3-O-methyl-α-D-glucopyranosyl)-(1→4)-O-(2-O-acetyl-6-O-benzyl-3-O-methyl-β-D-glucopyranosyl)-(1→4)-O-(2,6-di-O-benzyl-3-O-methyl-α-D-glucopyranosyl)-(1→4)-2-O-acetyl-6-O-benzyl-3-O-methyl-β-D-glucopyranoside (18)

The delevulination of 15 (1.3 g, 0.87 mmol) is carried out according to Method 2 in order to give 18 (1.05 g, 86%). $[\alpha]_D$+40 (c=0.6, dichloromethane). $^1$H NMR (CDCl$_3$) δ 7.36–7.23 (m, 30H, 6 Ph), 5.83–5.78 (m, 1H, OCH (CH:CH$_2$)), 5.50 (d, 1H, J=3.5 Hz, H-1'''), 5.47 (d, 1H, J=3.5 Hz, H-1'), 5.25–5.21 (dd, 1H, J=1.6 Hz, J=17 Hz, OCH$_2$ (CH:CH$_2$)), 5.16–5.13 (dd, 1H, J=1.4 Hz, J=10 Hz, OCH$_2$ (CH:CH$_2$)), 4.38 (d, 1H, J=6.5 Hz, H-1''), 4.31 (d, 1H, J=6.5 Hz, H-1), 4.08–4.02 (m, 1H, OCH$_2$(CH:CH$_2$)), 3.59 (m, 1H, H-4'''), 3.67, 3.53, 3.39, 3.29 (4s, 12H, 4 OCH$_3$), 2.09, 1.86 (2s, 6H, 2 Ac)

PREPARATION 18

Allyl O-(2,6-Di-O-benzyl-4-O-levulinyl-3-O-methyl-α-D-glucopyranosyl)-(1→4)-[O-(2-O-acetyl-6-O-benzyl-3-O-methyl-β-D-glucopyranosyl)-(1→4)-O-(2,6-di-O-benzyl-3-O-methyl-α-D-glucopyranosyl)-(1→4)]$_3$-2-O-acetyl-6-O-benzyl-3-O-methyl-β-D-glucopyranoside (19)

A mixture of 18 (842 mg, 0.53 mmol) and 17 (1.17 g, 0.74 mmol) is treated according to Method 1. The product is purified on a Toyopearl® HW-50 column (110×3.2 cm; 1/1 dichloromethane/ethanol) in order to give 19 (1.44 g, 85%). $[\alpha]_D$+57 (c=1.01, dichloromethane). $^1$H NMR (CDCl$_3$) d 7.35–7.20 (m, 60H, 12 Ph), 5.83–5.78 (m, 1H, OCH$_2$ (CH:CH$_2$)), 5.24–5.21 (dd, 1H, OCH$_2$(CH:CH$_2$)), 5.16–5.13 (dd, 1H, OCH$_2$(CH:CH$_2$)), 3.59, 3.56, 3.51, 3.47, 3.33, 3.26 (6s, 24H, 8 OCH$_3$), 2.75–2.35 (m, 4H, O(C:O)CH$_2$CH$_2$ (C:O)CH$_3$), 2.15, 2.09, 1.85, 1.84 (4s, 15H, 4 Ac and O(C:O)CH$_2$CH$_2$(C:O)CH$_3$);

δ of the main anomeric protons: 5.48; 4.37; 4.29; 4.23 ppm.

Anal. Calculated for $C_{156}O47H_{188}$ (2815.51): C, 66.56; H, 6.73. Found: C, 66.22; H, 6.75.

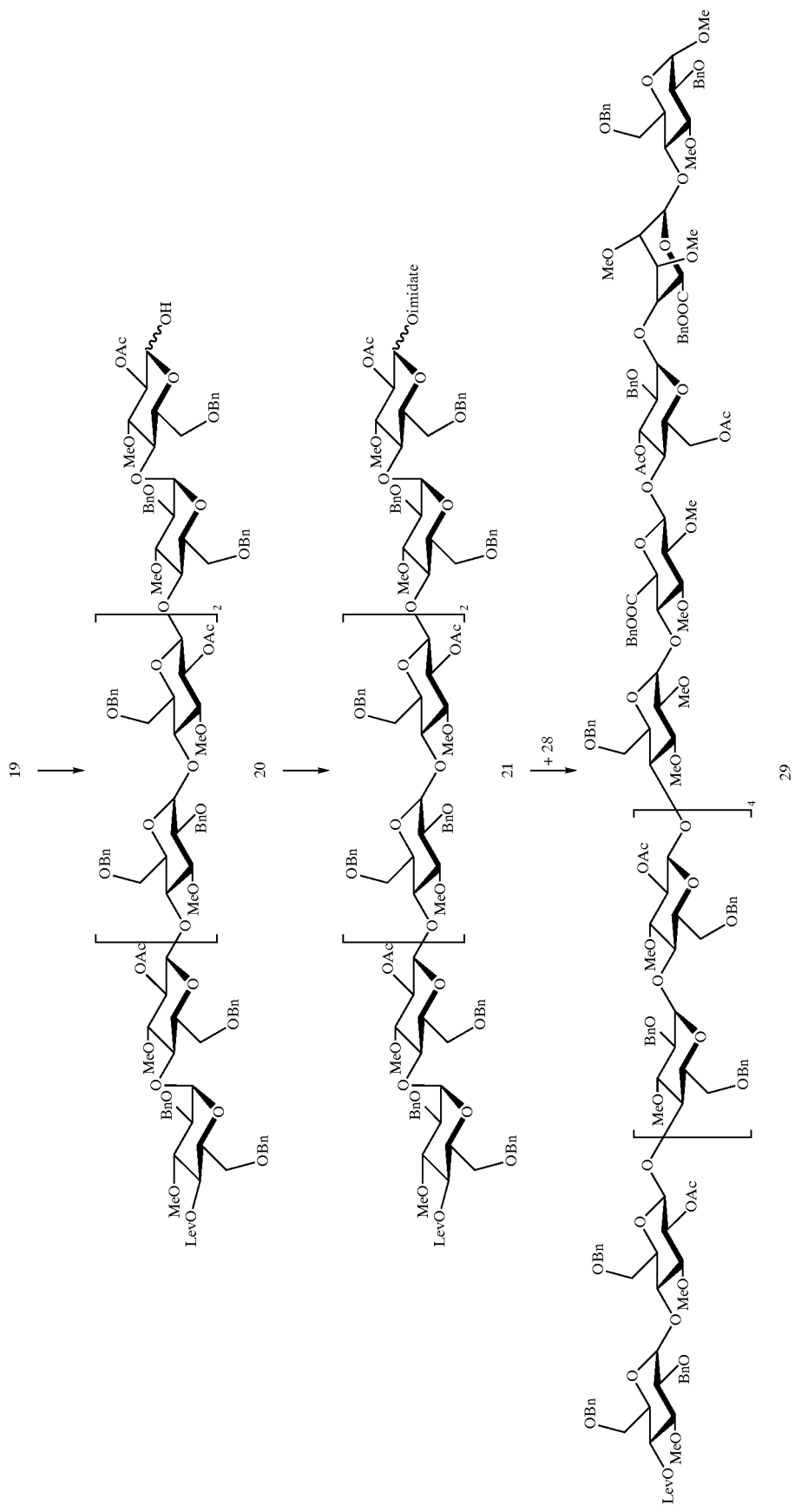
SCHEME 6
Synthesis of polysaccharide 29

PREPARATION 19

O-(2,6-Di-O-benzyl-4-O-levulinyl-3-O-methyl-α-D-glucopyranosyl)-(1-4)-[O-(2-O-acetyl-6-O-benzyl-3-O-methyl-β-D-glucopyranosyl)-(1-4)-O-(2,6-di-O-benzyl-3-O-methyl-α-D-glucopyranosyl)-(1-4)]₃-2-O-acetyl-6-O-benzyl-3-O-methyl-α,β-D-glucopyranose (20)

Compound 19 (720 mg, 0.25 mmol) is treated as in Preparation 15. The product is purified on a column of silica (3/2 and then 4/3 toluene/ethyl acetate) in order to obtain 20 (555 mg, 78%). [α]$_D$+70 (c=0.94, dichloromethane). TLC, R$_F$ 0.43, 1/1 toluene/ethyl acetate.

PREPARATION 20

O-(2,6-Di-O-benzyl-4-O-levulinyl-3-O-methyl-α-D-glucopyranosyl)-(1-4)-[O-(2-O-acetyl-6-O-benzyl-3-O-methyl-β-D-glucopyranosyl)-(1-4)-O(2,6-di-O-benzyl-3-O-methyl-α-D-glucopyranosyl)-(1-4)]₃-2-O-acetyl-6-O-benzyl-3-O-methyl-α,β-D-glucopyranose Trichloroacetimidate (21)

Compound 20 (540 mg, 0.195 mmol) is treated as in Preparation 16. The product is purified on a column of silica (3/2 toluene/ethyl acetate+1‰ of triethylamine) in order to give a mixture (α/β=27/73) of the imidates 21 (455 mg, 80%). TLC, RF 0.48, 3/2 toluene/ethyl acetate. ¹H NMR (CDCl₃) δ 8.60, 8.59 (2s, 1H, N:Hα and β), 7.35–7.21 (m, 60H, 12 Ph), 2.75–2.40 (m, 4H, O(C:O)CH₂CH₂(C:O)CH₃), 2.16, 2.06, 2.04, 1.85, 1.84 (5s, 15H, 4 Ac and O(C:O)CH₂CH₂(C:O)CH₃).

¹H NMR (CDCl₃) δ of the main anomeric protons: 6.50; 5.79; 5.51; 5.48; 4.29; 4.25 ppm.

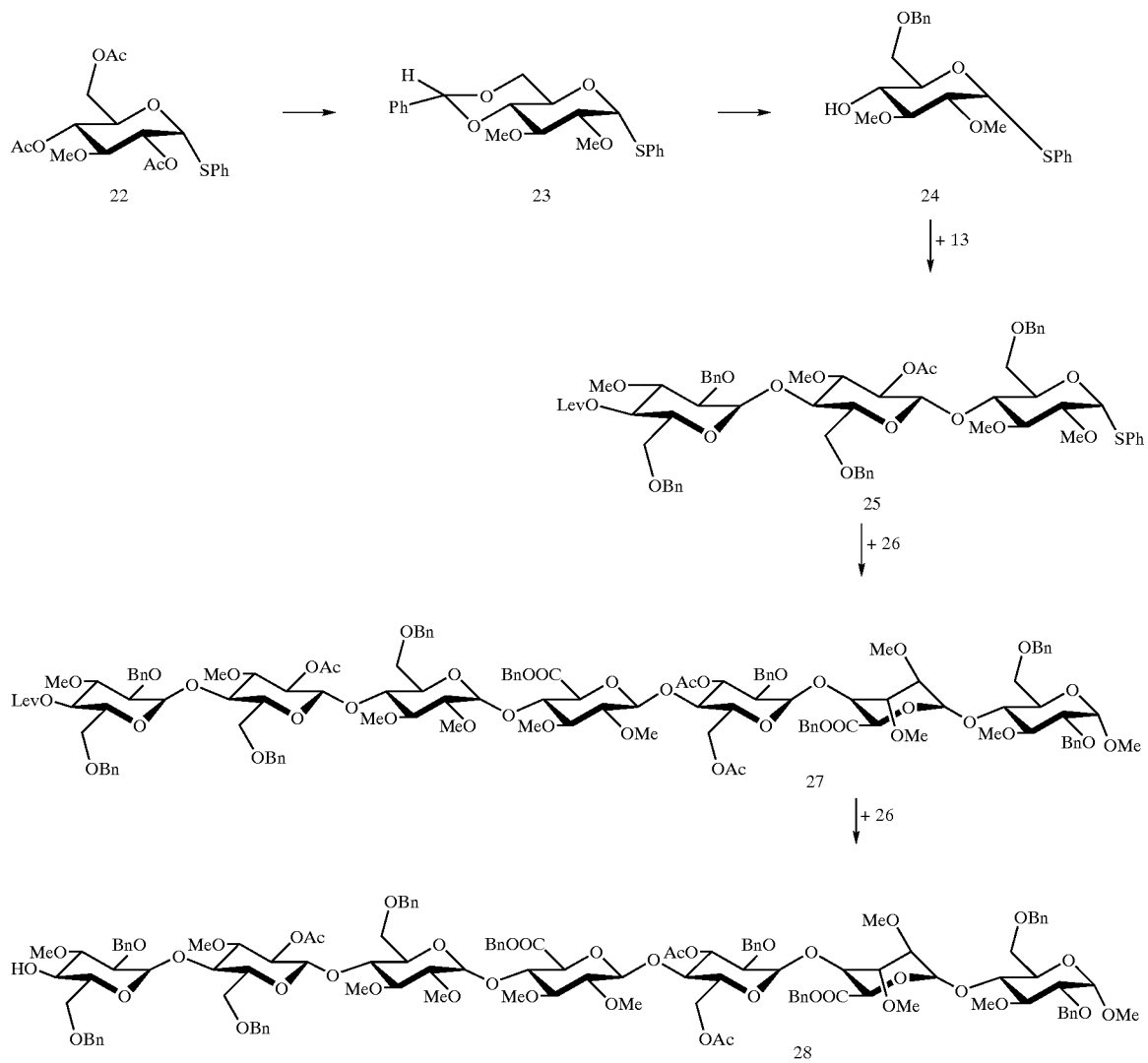

SCHEME 7
Synthesis of oligosaccharide 28

PREPARATION 21

Phenyl 2,4,6-Tri-O-acetyl-3-O-methyl-1-thio-α-D-glucopyranoside (22)

1,2,4,6-Tetra-O-acetyl-3-O-methyl-β-D-glucopyranose 1 (5.23 g, 14.4 mmol) is dissolved in toluene (45 ml). Thiophenol (3.0 ml, 28.8 mmol) is added, followed by dropwise addition of trifluoroborane diethyl etherate (1.77 ml, 14.4 mmol) and the mixture is then heated at 50° C. for 0.5 hour. It is diluted with dichloromethane, washed with saturated aqueous sodium hydrogen carbonate solution, with water, dried and concentrated. The residue is purified on a column of silica (5/2 cyclohexane/ethyl acetate) to give 22-α (1.00 g, 17%) and 22-β (2.71 g, 46%).

22-α, $R_F$ 0.44, 3/2 cyclohexane/ethyl acetate. $[α]_D$+230 (c=1, dichloromethane). ESIMS, positive mode: m/z+NaCl, 435 (M+Na)$^+$; +KF, 451 (M+K)$^+$. $^1$H NMR (CDCl$_3$) δ 7.46–7.27 (m, 5H, Ph), 5.89 (d, 1H, J=5.6 Hz, H-1), 5.05–4.97 (m, 2H, H-2 and H-4), 4.49–4.42 (m, 1H, H-5), 4.25–4.18 (m, 1H, H-6), 4.05–4.00 (m, 1H, H-6'), 3.66, (dd, 1H, J=9.5 Hz, H-3), 3.51 (s, 3H, OCH$_3$), 2.16, 2.12, 2.00 (3s, 9H, 3 Ac).

Anal. Calculated for $C_{19}H_{24}O_8S$ (412.46): C, 55.33; H, 5.87; S, 7.77. Found: C, 55.25; H, 5.90; S, 7.75.

PREPARATION 22

Phenyl 4,6-O-Benzylidene-2,3-di-O-methyl-1-thio-α-D-glycopyranoside (23)

Compound 22 (970 mg, 2.35 mmol) is dissolved in a 2/1 mixture of methanol and dichloromethane (18 ml). 2M sodium methoxide solution (150 ml) is added. After 0.5 hour at room temperature, the mixture is neutralized with Dowex® 50 (H+) resin, filtered and concentrated.

α,α-Dimethoxytoluene (0.7 ml, 4.0 mmol) and camphorsulphonic acid (51 mg, 0.22 mmol) are added to the above crude reaction mixture in acetonitrile (22 ml). The mixture is left stirring for 1 hour, neutralized by addition of triethylamine (0.50 ml) and concentrated.

Sodium hydride (73.0 mg, 2.80 mmol) is added, at 0° C., to a solution of the above crude product and methyl iodide (163 Al, 4.0 mmol) in N,N-dimethylformamide (9 ml). The mixture is left stirring for 1 hour and methanol is added. The mixture is extracted with ethyl acetate, washed with water, dried and concentrated to obtain 23 in solid form (840 mg, 94%). m.p.: 1780C. $[α]_D$+330 (c=1, dichloromethane). ESIMS, positive mode: m/z+NaCl, 411.4 (M+Na)$^+$; +KF, 427.4 (M+K). $^1$H NMR (CDCl$_3$) δ 7.50–7.24 (m, 10H, 2 Ph), 5.71 (d, 1H, J=3.4 Hz, H-1), 5.52 (s, 1H, C$_5$H$_5$CH), 3.62 (s, 3H, OCH), 3.55 (s, 3H, OCH$_3$).

Anal. Calculated for $C_{21}H_{24}O_5S$ (388.48): C, 64.92; H, 6.23; S, 8.25. Found: C, 64.87; H, 6.17; S, 7.85.

PREPARATION 23

Phenyl 6-O-Benzyl-2,3-di-O-methyl-1-thio-α-D-glucopyranoside (24)

Compound 23 (792 mg, 0.47 mmol) is treated as in Preparation 4. The product is purified on a column of silica (7/2 and then 2/1 cyclohexane/ethyl acetate) to give 24 (318 mg, 80%). $[α]_D$+243 (c=1, dichloromethane). ESIMS, positive mode: m/z+NaCl, 413 (M+Na)$^+$; +KF, 429 (M+K)$^+$. $^1$H NMR (CDCl$_3$) δ 7.52–7.22 (m, 10H, 2 Ph), 5.71 (d, 1H, J=5.3 Hz, H-1), 3.64 and 3.49 (2s, 6H, 2 OCH$_3$), 3.36 (dd, 1H, H-3).

Anal. Calculated for $C_{21}H_{26}O_5S$ (390.50): C, 64.59; H, 6.71; S, 8.21. Found: C, 64.05; H, 6.88; S, 7.74.

PREPARATION 24

Phenyl O-(2,6-Di-O-benzyl-4-O-levulinyl-3-O-methyl-α-D-glucopyranosyl)-(1-4)-α-(2-O-acetyl-6-O-benzyl-3-O-methyl-β-D-glucopyranosyl)-(1-4)-6-O-benzyl-2,3-di-O-methyl-1-thio-α-D-glucopyranoside (25)

A mixture of 13 (436 mg, 0.47 mmol) and 24 (153 mg, 0.39 mmol) is treated according to Method 1. The product is purified on a column (Sephadex® LH20, 1/1 ethanol/dichloromethane) to give pure 25 (309 mg, 68%). $[α]_D$144 (c=1, dichloromethane). ESIMS, positive mode: m/z+NaCl, 1175 (M+Na)$^+$; +KF, 1191 (M+K)$^+$. $^1$H NMR (CDCl$_3$) δ 7.51–7.21 (m, 25H, 5 Ph), 5.73 (d, 1H, J=5.2 Hz, H-1), 5.48 (d, 1H, J=3.5 Hz, H-1"), 4.46 (d, 1H, J=8 Hz, H-1'), 3.7, 3.54, 3.5, 3.31 (4s, 12H, 4 OCH$_3$), 2.70–2.41 (m, 4,H, O(C:O)CH$_2$CH$_2$(C:O)CH$_3$), 2.16, 2.01 (2s, 6H, 1 Ac and O(C:O)CH$_2$CH$_2$(C:O)CH$_3$).

Anal. Calculated for $C_{63}H_{76}O_{18}S$: C, 65.61; H, 6.64; S, 2.78. Found: C, 65.02; H, 6.60; S, 2.72.

PREPARATION 25

Methyl O-(2,6-Di-O-benzyl-4-O-levulinyl-3-O-methyl-α-D-glucopyranosyl)-(1-4)-O-(2-O-acetyl-6-O-benzyl-3-O-methyl-β-D-glucopyranosyl)-(1-4)-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-ax-D-glucopyranosyl)-(1-4)-O-(benzyl 2,3-di-O-methyl-α-L-idopyranosyluronate)-(1-4)-2,3,6-tri-O-benzyl-α-D-glucopyranoside (27)

A solution of N-iodosuccinimide (92 mg, 0.38 mmol) and triflic acid (37.5 μl, 0.38 mmol) in a 1/1 solution of 1,2-dichloroethane and ethyl ether (22 ml) is added, at −25° C. and under argon, to a mixture of 25 (451 mg, 0.39 mmol) and 26 (434 mg, 0.31 mmol), (P. Westerduin, et al. BioOrg. Med. Chem., 1994, 2, 1267) in 1,2-dichloroethane (7.5 ml) in the presence of 4 A molecular sieves (400 mg). After 30 minutes, solid sodium hydrogen carbonate is added. The solution is filtered, washed with sodium thiosulphate solution, with water, dried and evaporated. The residue is purified on a column of Sephadex® LH-20 (1/1 dichloromethane/ethanol) and then on a column of silica (1/1 and then 2/3 cyclohexane/ethyl acetate) to give pure 27 (487 mg, 64%). $[α]_D$+63 (c=0.54, dichloromethane). TLC, $R_F$ 0.28, 2/1 cyclohexane/ethyl acetate. ESIMS, positive mode: m/z+NaCl, 2454 (M+Na)$^+$; +KF, 2469 (M+K)$^+$. $^1$H NMR (CDCl$_3$) δ 7.38–7.2 (m, 50H, 10 Ph), 3.56, 3.52, 3.48, 3.46, 3.44, 3.42, 3.39, 3.30, 3.17 (9s, 27H, 9 OCH.), 2.75–2.4 (m, 4H, O-(C:O)CH$_2$CH$_2$C:O)CH$_3$), 2.15, 1.98, 1.97, 1.87, (4s, 12H, 3 Ac and O-(C:O)CH$_2$CH$_2$(C:C)CH$_3$); main anomeric protons: 5.57; 5.47; 5.30; 5.18; 4.57; 4.29; 4.08.

PREPARATION 26

Methyl O-(2,6-Di-O-benzyl-3-O-methyl-α-D-glucopyranosyl)-(1-4)-(2-O-acetyl-6-O-benzyl-3-O-methyl-β-D-glucopyranosyl)-(1-4)-O-(6-O-benzyl-2,3-di-O-methyl-α-D-glucopyranosyl)-(1-4)-O-(benzyl 2,3-di-O-methyl-β-D-glucopyranosyluronate)-(1-4)-α-(3,6-di-O-acetyl-2-O-benzyl-α-D-glucopyranosyl)-(1-4)-O-(benzyl 2,3-di-O-methyl-α-L-idopyranosyluronate)-(1-4)-2,3,6-tri-O-benzyl-α-D-glucopyranoside (28)

The delevulinization of 27 (498 mg, 0.2 mmol) is carried out according to Method 2 to give 28 (402 mg, 84%). $[\alpha]_D$+64 (c=1, $CH_2Cl_2$). ESIMS, positive mode: m/z 2352.9 $(M+NH_4)^+$. $^1H$ NMR ($CDCl_3$) δ 7.38–7.20 (m, 50H, 10 Ph), 3.67, 3.52, 3.49, 3.46, 3.44, 3.41, 3.40, 3.28, 3.17 (9s, 27H, 9 Ac), 2.65 (d, 1H, J=2.14 Hz, OH), 1.98, 1.96, 1.87 (3s, 9H, 3 Ac); main anomeric protons: 5.55; 5.49; 5.30; 5.18; 4.56; 4.31; 4.08.

Anal. Calculated for $C_{127}H_{152}O_{41}$ (2334.48): C, 65.34; H, 6.56. Found: C, 65.40; H, 6.62.

PREPARATION 27

Methyl O-(2,6-Di-O-benzyl-4-O-levulinyl-3-O-methyl-α-D-glucopyranosyl)-(1-4)-O-(2-O-acetyl-6-O-benzyl-3-O-methyl-β-D-glucopyranosyl)-(1-4)-[O-(2,6-di-O-benzyl-3-O-methyl-α-D-glucopyranosyl)-(1-4)-O-(2-O-acetyl-6-O-benzyl-3-O-methyl-β-D-glycopyranosyl)-(1-4) 14-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-(1-4)-2,3,6-tri-O-benzyl-α-D-glucopyranoside (29)

A mixture of 21 (340 mg, 1.16 mmol) and 28 (256 mg, 1.09 mmol) is treated according to Method 1. The residue is purified on a column of Toyopearl® HW-40 (3.2×70 cm, 1/1 dichloromethane/ethanol) to give the pure 15-mer 29 (421 mg, 76%). $[\alpha]_D$+65 (c=1, dichloromethane). ESIMS, positive mode: m/z+KF, 2584.3 $(M+2K)^{2+}$; 1736.5 $(M+3K)^{3+}$. $^1H$ NMR ($CDCl_3$) δ 7.35–7.18 (m, 105H, 21 Ph), 2.75–2.4 (m, 4H, O-(C:O)$CH_2CH_2$(C:O)$CH_3$), 2.15, 1.97, 1.95, 1.87, 1.84, 1.83 (6s, 24H, 7 Ac, and O(C:O)$CH_2CH_2$(C:O)$CH_2$); main anomeric protons: 5.55; 5.48; 5.30; 5.18; 4.56; 4.29; 4.22; 4.08.

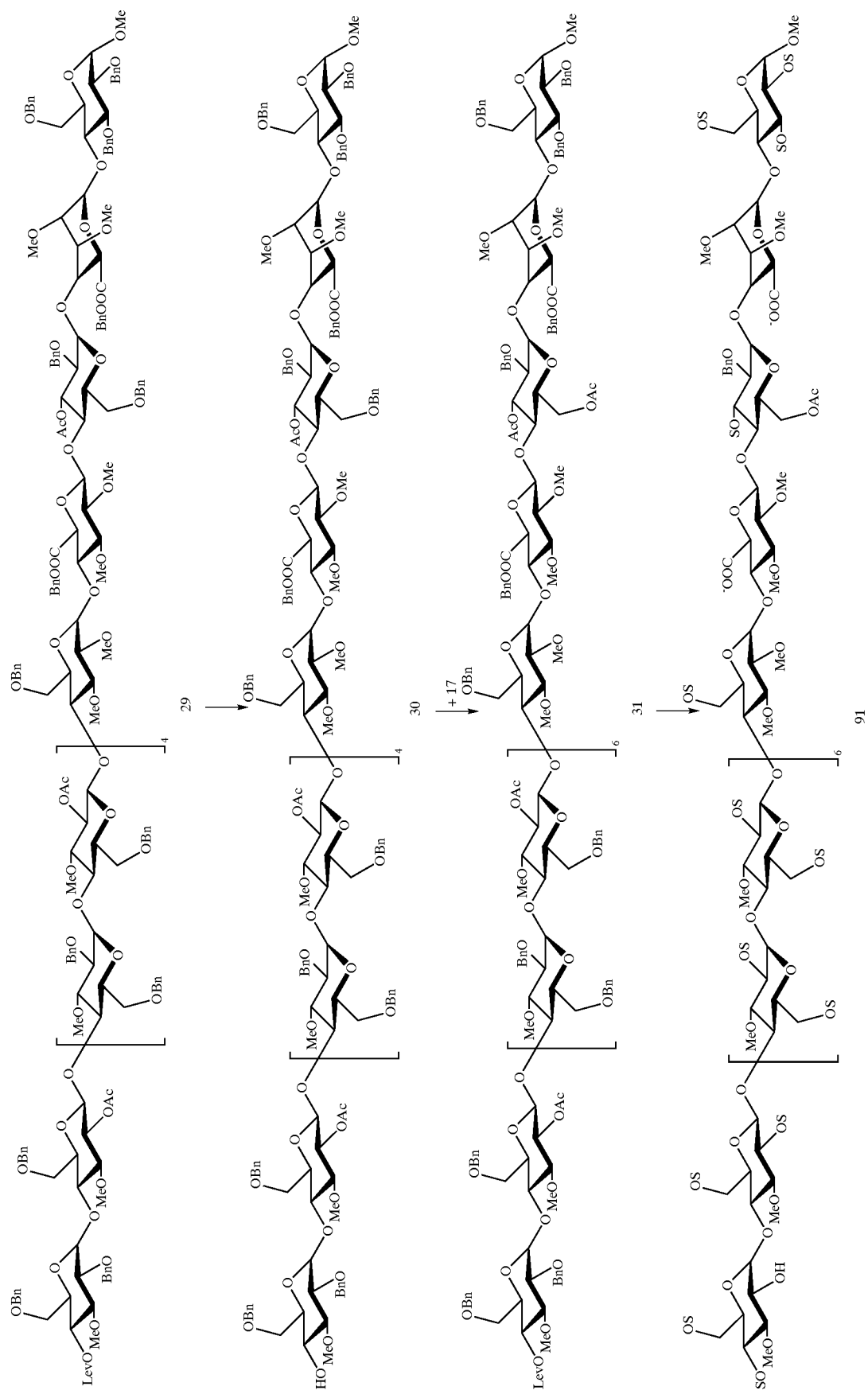

PREPARATION 28

Methyl O-(2,6-Di-O-benzyl-3-O-methyl-α-D-gluco-pyranosyl)-(1-4)-O-(2-O-acetyl-6-O-benzyl-3-O-methyl-β-D-glucopyranosyl)-(1-4)-[O-(2,6-di-O-benzyl-3-O-methyl-α-D-glucopyranosyl)-(1-4)-O-(2-O-acetyl-6-O-benzyl-3-O-methyl-β-D-glycopyranosyl)-(1-4)]-4-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-(1-4)-2,3,6-tri-O-benzyl-α-D-glucopyranoside (30)

Compound 29 (342 mg, 0.067 mmol) is treated according to Method 2 to give 30 (253 mg, 75%). $[\alpha]_D$+59 (c=0.92, dichloromethane). ESIMS, positive mode: m/z+KF, 2535.6 $(M+2K)^{2+}$. $^1$H NMR (CDCl$_3$) 6 of the main anomeric protons: 5.55; 5.50; 5.48; 5.30; 4.56; 4.30; 4.22; 4.08.

Anal. Calculated for $C_{275}H_{328}O_{85}$ (4993.37): C, 65.57; H, 6.60. Found: C, 65.09; H, 6.57.

PREPARATION 29

Methyl O-(2,6-Di-O-benzyl-4-O-levulinyl-3-O-methyl-α-D-glucopyranosyl)-(1-4)-O-(2-O-acetyl-6-O-benzyl-3-O-methyl-β-D-glucopyransoyl)-(1-4)-[O-(2,6-di-O-benzyl-3-O-methyl-α-D-glucopyranosyl)-(1-4)-O-(2-O-acetyl-6-O-benzyl-3-O-methyl-β-D-glycopyranosyl)-(1-4)]$_6$-(6-O-benzyl-2,3-di-O-methyl-α-D-glucopyranosyl)-(1-4)-O-(benzyl 2,3-di-O-Methyl-β-D-glucopyranosyluronate)-(1-4)-O-(3,6-di-O-acetyl-2-O-benzyl-α-D-glucopyranosyl)-(1-4)-(benzyl 2,3-di-O-methyl-α-L-idopyranosyluronate)-(1-4)-2,3,6-tri-O-benzyl-α-D-glucopyranoside (31)

A mixture of 17 (32.7 mg, 20.6 mmol) and 30 (80.7 mg, 16.3 nmol) is treated according to Method 1. The product is purified on a column of Toyopearl® HW-40 (1/1 dichloromethane/ethanol) to give 19-mer 31 (60 mg, 59%) $[\alpha]_D$+61 (c=0.82, dichloromethane). ESIMS, positive mode: m/z+NaCl, 2162.4 $(M+3Na)^{3+}$; +KF, 2178.5 $(M+3K)^{3+}$.

$^1$H NMR (CDCl$_3$) 6 of the main anomeric protons: 5.55; 5.48; 5.30; 5.17; $^{4.}5^6$; 4; 4.08.

SCHEME 9
Synthesis of disaccharide 37

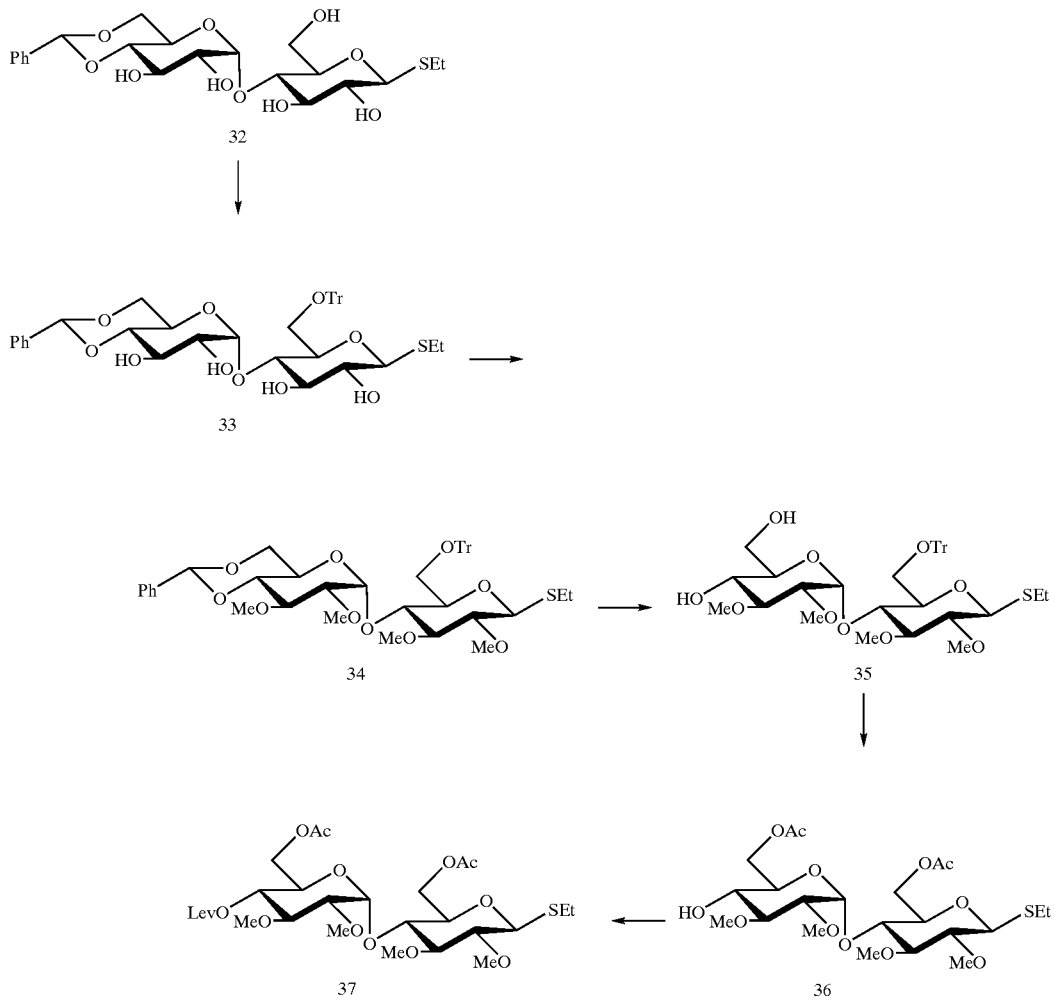

PREPARATION 30

Ethyl O-(4,6-O-Benzylidene-α-D-glucopyranosyl)-(1-4)-6-O-trityl-1-thio-β-D-glucopyranoside (33)

To a suspension of 32 (50.0 g, 0.105 mol) (J. Westman and M. Nilsson, J. Carbohydr. Chem., 1995, 14(7), 949–960) in dichloromethane (620 ml) under argon are added triethylamine (35 ml, 0.252 mol), trityl chloride (29.3 g, 0.105 mol) and 4-dimethylaminopyridine (1.28 g, 10 mmol). The mixture is maintained at reflux for 2 hours (TLC), left to cool to room temperature, diluted with dichloromethane (500 ml) and then washed successively with cold aqueous 10% potassium hydrogen sulphate solution, with water and with saturated sodium chloride solution. The solution is dried, concentrated and filtered on a column of silica (65/35 and then 50/50 toluene/acetone) in order to obtain the crude product 33, which is sufficiently pure to be used in the following step. An analytic sample is chromatographed. $[\alpha]_D$+53 (c=0.74, dichloromethane). ESIMS, negative mode: m/z 715 (M-H)$^-$. $^1$H NMR (CD$_2$Cl$_2$) δ 7.52–7.25 (m, 20H, 4Ph), 5.42 (s, C$_6$H$_5$CH), 4.97 (d, J=3.5 Hz, H-1'), 4.40 (d, J=9.6 Hz, H-1), 3.82 (t, J=9.3 Hz, H-3'), 3.70, 3.68 (m, 2H, H-3, H-4), 3.60 (dd, J≈2.0, 11.0 Hz, H-6a), 3.55 (td, J=5.2, 9.7, 9.7 Hz, H-5'), 3.49–3.45 (m, 3H, H-2, H-2', H-5), 3.38 (dd, J=10.5 Hz, H-6'a), 3.33 (dd, H-6'b), 3.30–3.27 (m, 2H, H-4', H-6b), 2.90–2.77 (m, 2 H, SCH$_2$CH$_3$), 1.40–1.37 (t, 3H, CH$_2$CH$_3$).

Anal. Calculated for C$_{40}$H$_{44}$O$_{10}$S: C, 67.02; H, 6.19; S, 4.47. Found: C, 66.83; H, 6.19; S, 4.19.

PREPARATION 31

Ethyl O-(4,6-O-Benzylidene-2,3-di-O-methyl-α-D-gluco-pyranosyl)-(1-4)-2,3-di-O-methyl-6-O-trityl-1-thio-β-D-lucopyranoside (34)

Methyl iodide (34 ml, 0.536 mol) is added dropwise, under argon, to a solution of compound 33 (64.1 g) in N,N-dimethylformamide (600 ml). The solution is cooled to 0° C. and sodium hydride (13.5 g, 0.536 mol) is added slowly. The suspension is stirred for 2 hours at room temperature and then cooled to 0° C. and methanol (35 ml) is added dropwise and, after stirring for 2 hours, the mixture is diluted in ethyl acetate (500 ml) and water (600 ml). The aqueous phase is extracted with ethyl acetate and the organic phases are washed with water, dried and concentrated. The residue 34 is sufficiently pure for the following step. An analytical sample is purified on a column of silica (70/30 cyclohexane/acetone). $[\alpha]_D$+45 (c=0.83, dichloromethane). ESIMS, positive mode: m/z+NaCl, 795 (M+Na)$^+$; +KF, 811 (M+K)$^+$. $^1$H NMR (CDCl$_3$) δ 7.52–7.19 (m, 20H, 4Ph), 5.51 (d, J=3.3 Hz, H-1'), 5.43 (s, C$_6$H$_5$CH), 4.45 (d, J=9.8 Hz, H-1), 3.60, 3.59, 3.51, 3.49 (4s, 12H, 4OCH$_3$), 2.86 (q, 2H, J=7.5 Hz, SCH$_2$CH$_3$), 1.40 (t, 3H, SCH$_2$CH$_3$).

Anal. Calculated for C$_{44}$H$_{52}$O$_{10}$S: C, 68.37; H, 6.78; S, 4.15. Found: C, 68.28; H, 6.98; S, 4.09.

PREPARATION 32

Ethyl O-(2,3-Di-O-methyl-α-D-glucopyranosyl)-(1-4)-2,3-di-O-methyl-1-thio-β-D-glucopyranoside (35)

A suspension of crude product 34 (67.4 g) is heated at 80° C. for 2 hours in aqueous 60% acetic acid solution (470 ml). The reaction mixture is cooled, filtered and concentrated. The residue is treated with sodium methoxide (940 mg) in methanol (200 ml) for 1 hour. The solution is then neutralized with Dowex® 50WX4 (H$^+$) resin and then filtered, concentrated and purified on a column of silica (60/40 toluene/acetone) in order to obtain 35 (27.9 g, 60% over three steps). $[\alpha]_D$+26 (c=1.07, dichloromethane). ESIMS, positive mode: m/z, +NaCl, 465 (M+Na)$^+$; +KF, 481 (M+K)$^-$. $^1$H NMR (CDCl$_3$) δ 5.62 (d, J=3.9 Hz, H-1'), 4.35 (d, J=9.8 Hz, H-1), 3.64, 3.64, 3.59, 3.58 (4s, 12H, 4OCH$_3$), 1.29 (t, 3H, J=7.4 Hz, SCH$_2$CH$_3$).

Anal. Calculated for C$_{18}$H$_{34}$O$_{10}$S. H$_2$O: C, 46.94; H, 7.87; S, 6.96. Found: C, 47.19; H, 7.72; S, 6.70.

PREPARATION 33

Ethyl O-(6-O-Acetyl-2,3-di-O-methyl-α-D-gluco-pyranosyl)-(1-4)-6-O-acetyl-2,3-di-O-methyl-1-thio-β-D-glucopyranoside (36)

A solution of triol 35 (5.86 g, 13.2 mmol) and N-acetylimidazole (3.21 g, 29.1 mmol) in 1,2-dichloroethane (120 ml) is refluxed for 16 hours. A further portion of N-acetylimidazole (440 mg, 3.96 mmol) is added and the mixture is stirred for 4 hours. It is left to cool to room temperature and methanol (2 ml) is then added. The mixture is stirred for a further 1 hour and then diluted with dichloromethane (1 l), washed successively with cold aqueous IM hydrochloric acid solution, with cold water, with saturated aqueous sodium hydrogen carbonate solution, with water, dried and concentrated. The residue is chromatographed (3.5/1 toluene/acetone) in order to obtain the diacetate 36 (3.97 g, 57%). $[\alpha]_D$+33 (c=1.90, dichloromethane). ESIMS, positive mode: m/z, +NaCl, 549 (M+Na)$^+$; +KF, 565 (M+K)$^+$. $^1$H NMR (CDCl$_3$) δ 5.51 (d, J=3.9 Hz, H-1'), 4.34 (d, J=9.8 Hz, H-1), 3.64, 3.63, 3.59, 3.56 (4s, 12H, 4OCH$_3$), 2.11, 2.06 (2s, 6H, 2Ac), 1.31 (t, 3H, J=7.4 Hz, SCH$_2$CH$_3$).

Anal. Calculated for C$_{22}$H$_{38}$O$_{12}$: C, 50.17; H, 7.27; S, 6.09. Found: C, 50.15; H, 7.49; S, 5.89.

PREPARATION 34

Ethyl O-(6-O-Acetyl-4-O-levulinyl-2,3-di-O-methyl-α-D-glucopyranosyl)-(1-4)-6-O-acetyl-2,3-di-O-methyl-1-thio-β-D-glucopyranoside (37)

To a solution of diacetate 36 (19.4 g, 36.8 mmol) in dioxane (400 ml), under argon, are added levulinic acid (7.53 ml, 73.5 mmol), 1-(3-dimethylaminopropyl)-3-ethylcarbodiimide hydrochloride (14.1 g, 73.5 mmol) and 4-dimethylaminopyridine (900 mg, 7.35 mmol). The mixture is stirred for 3.5 hours, diluted with dichloromethane (1.5 l) and then washed successively with water, with aqueous 10% otassium hydrogen sulphate solution, with water, with queous 2% sodium hydrogen carbonate solution, with water and then dried and concentrated. The residue is chromatographed (97/3 and then 79/21 dichloromethane/acetone) in order to obtain the derivative 37 (21.8 g, 95%). $[\alpha]_D$+40 (c=0.72, dichloromethane). ESIMS, positive mode: m/z, +NaCl, 647 (M+Na)$^+$; +KF, 663 (M+K)$^+$. $^1$H NMR (CDCl$_3$) δ 5.56 (d, J=3.9 Hz, H-1'), 4.35 (d, J 9.8 Hz, H-1), 3.64, 3.60, 3.58, 3.55 (4s, 12H, 4OCH$_3$), 2.76–2.71 (m, 4H, O(C:O)CH$_2$CH$_2$(C:O)CH$_3$), 2.19, 2.08, 2.07 (3s, 9H, 2Ac and O(C:O)CH$_2$CH$_2$(C:O)CH), 1.31 (t, 3H, J=7.4 Hz, SCH$_2$CH$_3$).

Anal. Calculated for C$_{27}$H$_{44}$O$_{14}$S: C, 51.91; H, 7.10; S, 5.13. Found: C, 51.88; H, 7.05; S, 4.96.

SCHEME 10
Synthesis of disaccharide 38 and 40

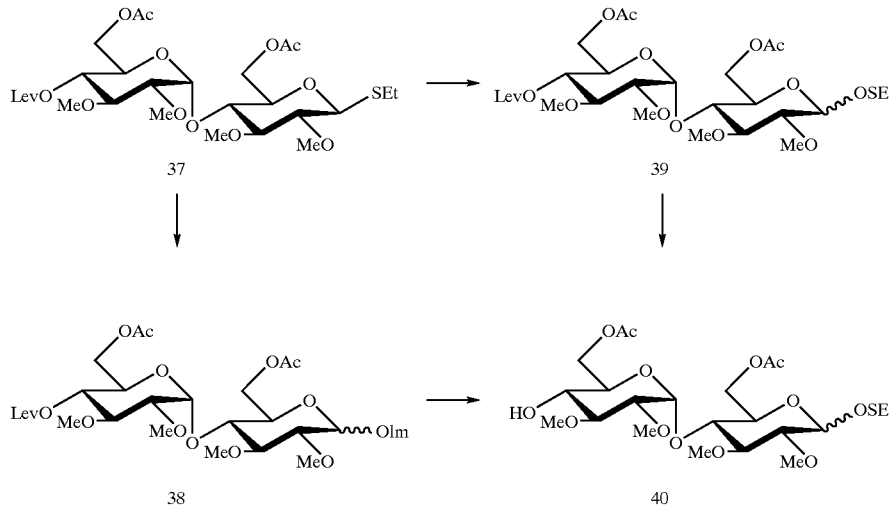

PREPARATION 35

O-(6-O-Acetyl-4-O-levulinyl-2,3-di-O-methyl-α-D-glucopyranosyl)-(1-4)-6-O-acetyl-2,3-di-O-methyl-α,β-D-glucopyranose trichloroacetimidate (38)

To a solution of thioglycoside 37 (9.53 g, 15.3 mmol) in a 1/1 dichloromethane/ethyl ether mixture (180 ml) are added water (1.4 ml, 76.3 mmol), N-iodosuccinimide (6.84 g, 30.5 mmol) and silver triflate (0.51 g, 1.98 mmol). After 15 minutes (TLC), saturated aqueous sodium hydrogen carbonate solution (5 ml) is added and the reaction mixture is diluted in dichloromethane (1.5 l), washed with water, aqueous 1M sodium thiosulphate solution and aqueous 2% sodium hydrogen carbonate solution. The solution is dried and concentrated and the residue is purified on a column of silica (80/40 and then 100/0 ethyl acetate/cyclohexane) in order to give a solid which is used, without characterization, in the following step. A solution of the above compound (7.88 g, 13.6 mmol) in dichloromethane (120 ml) under argon is treated with caesium carbonate (7.08 g, 21.7 mmol) and trichloroacetonitrile (6.81 ml, 67.9 mmol). After 40 minutes (TLC), the mixture is filtered, concentrated and purified (85/15 toluene/acetone) in order to obtain the imidate 38 (9.16 g, 83% over two steps). $[\alpha]_D$+118 (c=1.00, dichloromethane). ESIMS, positive mode: m/z+NaCl, 746 (M+Na)$^+$; 741 (M+NH$_4$)$^+$. $^1$H NMR (CDCl$_3$) δ 8.66, 8.65 (2s, 1H, α and β N:H), 6.52 (d, J=3.6 Hz, H-1α), 5.70 (d, J=7.5 Hz, H-1β), 5.58 (d, J=3.7 Hz, H-1'), 2.78–2.57 (m, 4H, O(C:O)CH$_2$CH$_2$(C:O)CH$_3$), 2.18, 2.07, 2.06 (3s, 9H, 2Ac and O(C:O)CH$_2$CH$_2$(C:O)CH$_3$).

Anal. Calculated for C$_{27}$H$_{40}$Cl$_3$NO$_{15}$. 0.5 H$_2$O: C, 44.18; H, 5.63; N, 1.98. Found: C, 44.14; H, 5.61; N, 1.97.

PREPARATION 36

2-(Trimethylsilyl)ethyl O-(6-O-Acetyl-4-O-levulinyl-2,3-di-O-methyl-α-D-glucopyranosyl)-(1-4)-6-O-acetyl-2,3-di-O-methyl-α,β-D-glucopyranoside (39)

The thioglycoside 37 (10.6 g, 16.94 mmol) is treated according to Method 3 with 2-(trimethylsilyl)ethanol (4.8 ml, 33.90 mmol) in a 1/2 dichloromethane/ethyl ether mixture (105 ml). The residue obtained is purified by chromatography (1/1 acetone/dichloromethane) in order to obtain compound 39 (9.80 g, 85%) in the form of a mixture of anomers (α/β 65/35). ESIMS, positive mode: m/z+NaCl, 703 (M+Na)$^+$. $^1$H NMR (CDCl$_3$) δ 5.58 (d, J=3.9 Hz, H-1'), 4.94 (d, J=3.5 Hz, H-1α), 4.26 (d, J=7.7 Hz, H-1β), 2.76–2.56 (m, 4H, O(C:O)CH$_2$CH$_2$(C:O)CH$_3$), 2.17, 2.08, 2.05 (3s, 9H, 2Ac and O(C:O)CH$_2$CH$_2$(C:O)CH$_3$), 1.18–0.88 (m, 2H, OCH$_2$CH$_2$Si(CH$_3$)$_3$), 0.02 (s, 9H, CH$_2$CH$_2$Si(CH)$_3$).

Anal. Calculated for C$_{30}$H$_{52}$O$_{15}$Si: C, 52.92; H, 7.69. Found: C, 53.29; H, 7.75.

PREPARATION 37

2-(Trimethylsilyl)ethyl O-(6-O-Acetyl-2,3-di-O-methyl-α-D-glucopyranosyl)-(1-4)-6-O-acetyl-2,3-di-O-methyl-α,β-D-glucopyranoside (40)

Compound 39 (9.41 g, 13.82 mmol) is treated according to Method 2 with hydrazine acetate (10 mol/mol) in a 1/2 toluene/ethanol mixture (21 ml/mmol). The residue is chromatographed (60/40 acetone/toluene) in order to obtain 40α (4.81 g, 60%) as well as a 40α/β mixture (3.06 g, 37%). 40α: $[\alpha]_D$+132 (c=0.61, dichloromethane). ESIMS, positive mode: m/z, +NaCl, 605 (M+Na)$^+$; +KF, 621 (M+K)$^+$. $^1$H NMR (CDCl$_3$) δ 5.55 (d, J=3.8 Hz, H-1'), 4.95 (d, J=3.6 Hz, H-1), 2.10, 2.08 (2s, 6H, 2Ac), 1.16–0.89 (m, 2H, OCH$_2$CH$_2$Si(CH$_3$)$_3$), 0.02 (s, 9H, OCH$_2$CH$_2$Si(CH$_3$)$_3$).

Anal. Calculated for C$_{25}$H$_{46}$O$_{13}$Si: C, 51.53; H, 7.96. Found: C, 51.37; H, 8.06.

SCHEME 11
Synthesis of tetrasaccharide 41

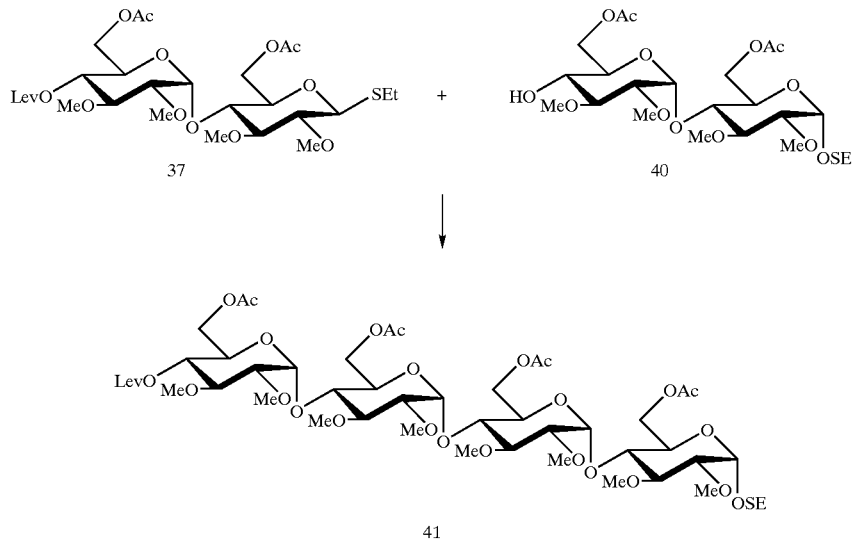

PREPARATION 38

2-(Trimethylsilyl)ethyl O-(6-O-Acetyl-4-O-levulinyl-2,3-di-O-methyl-α-D-glucopyranosyl)-(1-4)-[O-(6-O-acetyl-2,3-di-O-methyl-α-D-glucopyrano-syl)-(1-4)-]$_2$-6-(O-acetyl-2,3-di-O-methyl-α-D-glucopyranoside (41)

Thioglycoside 37 (4.21 g, 6.74 mmol) and the glycosyl acceptor 40 (3.57 g, 6.13 mmol) are treated according to Method 3 in a 1/2 dichloromethane/ethyl ether mixture (105 ml). The residue is purified by chromatography on silica (3/1 and then 9/1 acetone/cyclohexane) in order to obtain 41 (4.81 g, 69%). [α]$_D$+143 (c=0.56, dichloromethane). ESIMS, positive mode: m/z, +NaCl, 1167 (M+Na)$^+$; +KF, 1183 (M+K)$^+$. $^1$H NMR (CDCl$_3$) δ 5.57 (d, J=3.9 Hz, H-1'''), 5.44, 5.41 (2d, J=3.8 Hz, H-1", H-1'), 4,96 (d, J=3.6 Hz, H-1), 2.78–2.58 (m, 4H, O(C:O) CH$_2$CH$_2$(C:O)CH$_3$), 2.18, 2.12, 2.12, 2.09, 2.06, (5s, 15H, 4Ac and O(C:O)CH$_2$CH$_2$(C:O)CH$_3$), 1.21–0.97 (m, 2H, OCH$_2$CH$_2$Si(CH$_3$)$_3$), 0.03 (S, 9H, OCH$_2$CH$_2$Si(CH$_3$)$_3$).

Anal. Calculated for C$_{50}$H$_{84}$O$_{27}$Si: C, 52.44; H, 7.39. Found: C, 52.29; H, 7.46.

SCHEME 12
Synthesis of tetrasaccharide 42

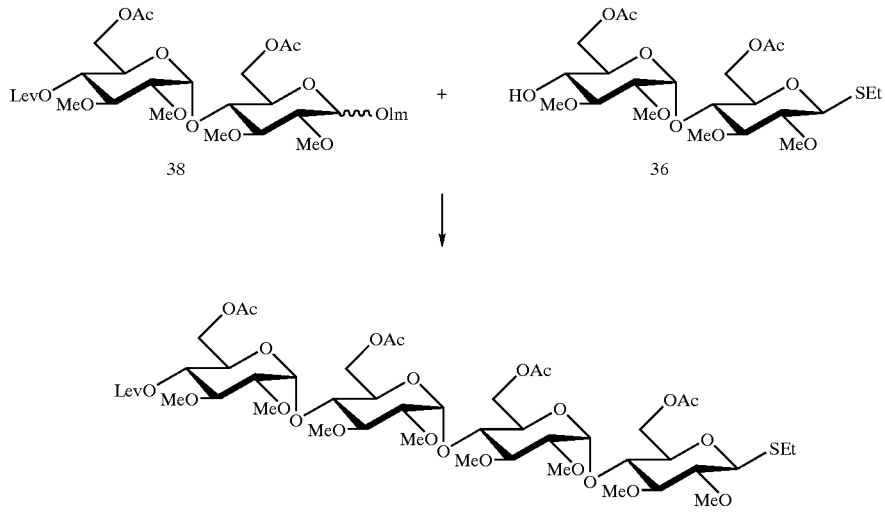

PREPARATION 39

Ethyl O-(6-O-Acetyl-4-O-levulinyl-2,3-di-O-methyl-α-D-glucopyranosyl)-(1-4)-[O-(6-O-acetyl-2,3-di-O-methyl-α-D-glucopyranosyl)-(1-4)-]$_2$-6-(O-acetyl-2,3-di-O-methyl-1-thio-β-D-glucopyranoside (42)

A solution of imidate 38 (1.10 g, 1.52 mmol) and glycosyl acceptor 36 (806 mg, 1.38 mmol) are treated in a 1/2 dichloromethane/ethyl ether mixture (22 ml) according to Method 1. The product is purified by chromatography on silica (2.5/1 and then 3/1 ethyl acetate/cyclohexane) in order to obtain 42 (1.12 g, 71%). $[\alpha]_D$+95 (c=1.00, dichloromethane). ESIMS, positive mode: m/z, +NaCl, 1111 (M+Na)$^+$; +KF, 1127 (M+K)$^+$. $^1$H NMR (CDCl$_3$) δ 5.55 (d, J=3.9 Hz, H-1'''), 5.39, 5.37 (2d, J=3.8 and 3.9 Hz, H-1'', H-1'), 4,34 (d, J=9.7 Hz, H-1), 2.84–2.51 (m, 6H, SCH$_2$CH$_3$, O(C:O)CH$_2$CH$_2$(C:O)CH$_3$), 2.17, 2.10, 2.09, 2.08, 2.04, (5s, 15H, 4Ac and O(C:O)CH$_2$CH$_2$(C:O)CH$_3$), 1.30(t,3H, J 7.4 Hz, SCH$_2$CH$_3$).

Anal. Calculated for C$_{47}$H$_{76}$O$_{26}$S: C, 51.83; H, 7.03; S, 2.94. Found: C, 51.66; H, 7.02; S, 2.94.

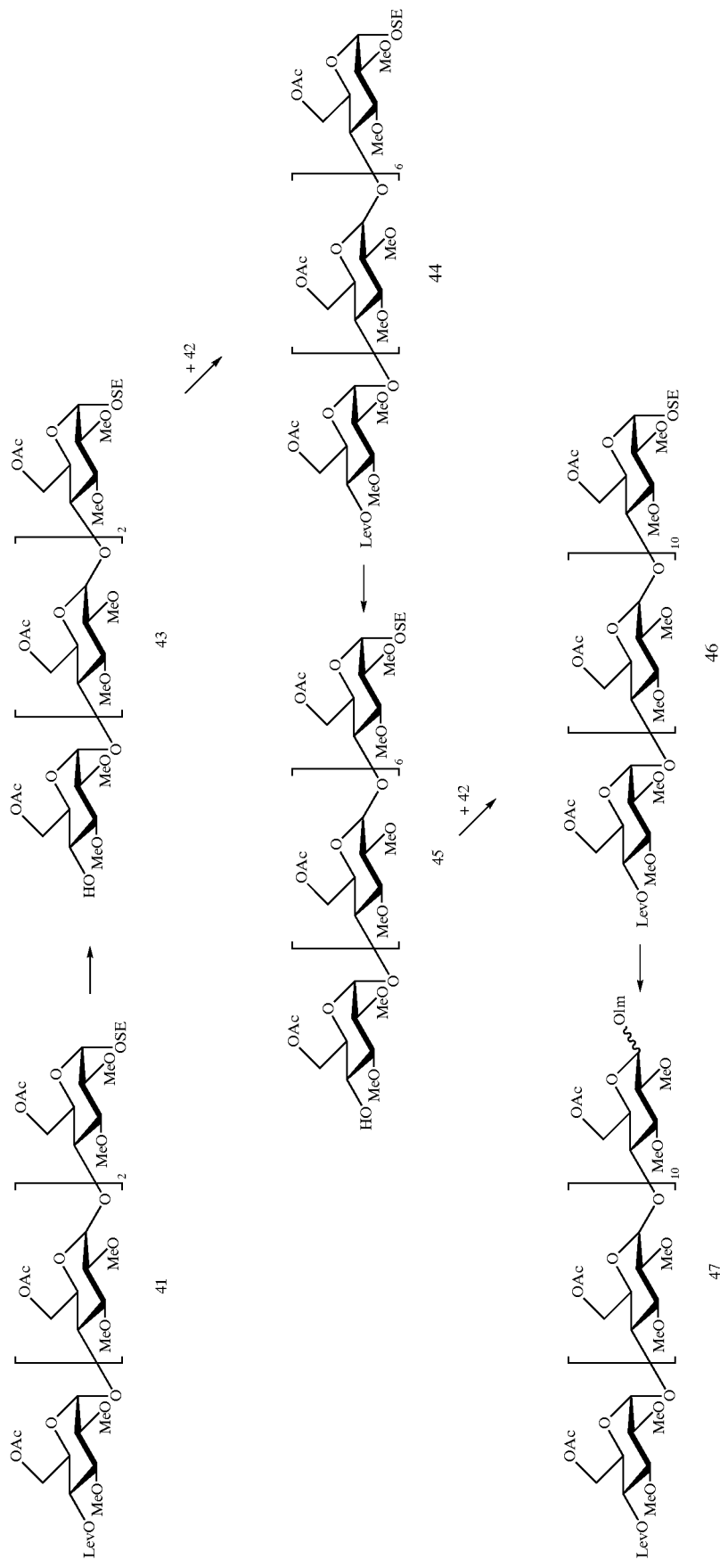

PREPARATION 40

2-(Trimethylsilyl)ethyl [O-(6-O-Acetyl-2,3-di-O-methyl-α-D-glucopyranosyl)-(1-4)-]$_3$-6-O-acetyl-2,3-di-O-methyl-α-D-glucopyranoside (43)

Compound 41 (4.71 g, 4.11 mmol) is reacted as in Preparation 37 in order to obtain, after column chromatography (3/2 cyclohexane/acetone), the derivative 43 (4.11 g, 95%). [α]$_D$+154 (c=0.63, dichloromethane). ESIMS, positive mode: m/z,+NaCl, 1069 (M+Na)$^+$; +KF, 1085 (M+K)$^+$. $^1$H NMR (CDCl$_3$) δ 5.46, 5.46 (2d, 3H, J=3.9 Hz, H-1', H-1", H-1'''), 4.95 (d, J=3.5 Hz, H-1), 2.81 (d, J=4.4 Hz, OH), 2.11, 2.09, 2.08 (3s, 12H, 4Ac), 1.19–0.97 (m, 2H, OCH$_2$CH$_2$Si(CH$_3$)$_3$), 0.03, (s, 9H, OCH$_2$CH$_2$Si(CH$_3$)$_3$).

Anal. Calculated for C$_{45}$H$_{78}$O$_{25}$Si: C, 51.61; H, 7.51. Found: C, 51.39; H, 7.54.

PREPARATION 41

2-(Trimethylsilyl)ethyl O-(6-O-Acetyl-4-O-levulinyl-2,3-di-O-methyl-α-D-glucopyranosyl)-(1-4)-[O-(6-O-acetyl-2,3-di-O-methyl-α-D-glucopyranosyl)-(1-4)-]$_6$-6-O-acetyl-2,3-di-O-methyl-α-D-glucopyranoside (44)

Thioglycoside 42 (3.86 g, 3.54 mmol) and the glycosyl acceptor 43 (3.60 g, 3.44 mmol) are treated according to Preparation 38. The product is chromatographed (7/2 and then 2/1 dichloromethane/acetone) in order to obtain 44 (5.71 g, 80%). [α]$_D$+161 (c=0.65, dichloromethane). ESIMS, positive mode: monoisotopic mass=2072.8, chemical mass=2074.2, experimental mass=2074±1 a.m.u. $^1$H NMR (CDCl$_3$) δ 5.54, (d, J=3.8 Hz, H-1 unit NR), 5.47–5.40 (m, 6H, H-1), 4.95 (d, J=3.7 Hz, H-1 unit R), 2.84–2.51 (m, 4H, O(C:O)CH$_2$CH$_2$(C:O)CH$_3$), 2.17, 2.13, 2.12, 2.11, 2.11, 2.08, 2.05 (7s, 27H, 8Ac and O(C:O)CH$_2$CH$_2$(C:O)CH$_3$, 1.18–0.97 (m, 2H, OCH$_2$CH$_2$Si(CH$_3$)$_3$), 0.03 (s, 9H, OCH$_2$CH$_2$Si(CH$_3$)$_3$).

Anal. Calculated for C$_{90}$H$_{148}$O$_{51}$Si: C, 52.12; H, 7.19. Found: C, 51.98; H, 7.25.

PREPARATION 42

2-(Trimethylsilyl)ethyl [O-(6-O-Acetyl-2,3-di-O-methyl-α-D-glucopyranosyl)-(1-4)-]$_7$-6-O-acetyl-2,3-di-O-methyl-α-D-glucopyranoside (45)

1M Hydrazine hydrate solution in a 3/2 acetic acid/pyridine mixture (7.3 ml) is added, at 0° C., to a solution of compound 44 (3.00 g, 1.45 mmol) in pyridine (5 ml). After stirring for 20 minutes, the reaction mixture is evaporated, diluted in dichloromethane (400 ml), washed with aqueous 10% potassium hydrogen sulphate solution, water, aqueous 2% sodium hydrogen carbonate solution and water. The solution is dried and concentrated and the residue is chromatographed in order to obtain 45 (2.43 g, 85%). [α]$_D$+167 (c=0.57, dichloromethane). ESIMS, positive mode: monoisotopic mass=1974.8, chemical mass=1976.1, experimental mass=1975.4±2 a.m.u. $^1$H NMR (CDCl$_3$) δ 5.47–5.40 (m, 7H, H-1), 4.95 (d, J=3.7 Hz, H-1 unit R), 2.80 (d, J=4.4 Hz, OH), 2.13, 2.11, 2.10, 2.08, 2.07 (5s, 24H, 8Ac), 1.18–0.97 (m, 2H, OCH$_2$CH$_2$Si(CH$_3$)$_3$), 0.03 (s, 9H, OCH$_2$CH$_2$Si(CH$_3$)$_3$).

Anal. Calculated for C$_{85}$H$_{142}$O$_{49}$Si: C, 51.66; H, 7.24. Found: C, 51.32; H, 7.26.

PREPARATION 43

2-(Trimethylsilyl)ethyl O-(6-O-Acetyl-4-O-levulinyl-2,3-di-O-methyl-α-D-glucopyranosyl)-(1-4)-[O-(6-O-acetyl-2,3-di-O-methyl-α-D-glucopyranosyl)-(1-4)-]$_{10}$-6-O-acetyl-2,3-di-O-methyl-α-D-glucopyranoside (46)

Compound 42 (1.35 g, 1.24 mmol) and compound 45 (2.38 g, 1.20 mmol) are treated according to Preparation 38. The residue is chromatographed (4/3 cyclohexane/acetone) in order to obtain 46 (2.56 g, 71%). [α]$_D$+166 (c=0.88, dichloromethane). ESIMS, positive mode: monoisotopic mass=3001.3, chemical mass=3003.2, experimental mass=3004±1 a.m.u. $^1$H NMR (CDCl$_3$) δ 5.54, (d, J=3.8 Hz, H-1 unit NR), 5.47–5.40, (m, 10H, H-1), 4.95 (d, J=3.7 Hz, H-1 unit R), 2.81–2.51 (m, 4H, O(C:O)CH$_2$CH$_2$(C:O)CH$_3$), 2.17, 2.13, 2.12, 2.11, 2.11, 2.08, 2.05 (7s, 39H, 12Ac and O(C:O)CH$_2$CH$_2$(C:O)CH$_3$), 1.17–0.96 (m, 2H, OCH$_2$CH$_2$Si(CH$_3$)$_3$), 0.03 (s, 9H, OCH$_2$CH$_2$Si(CH$_3$)$_3$).

Anal. Calculated for C$_{130}$H$_{212}$O$_{75}$Si: C, 51.99; H, 7.12. Found: C, 51.63; H, 7.12.

PREPARATION 44

(6-O-Acetyl-4-O-levulinyl-2,3-di-O-methyl-α-D-gluco-pyranosyl)-(1-4)-[O-(6-O-acetyl-2,3-di-O-methyl-α-D-glucopyranosyl)-(1-4)-]$_{10}$-6-O-acetyl-2,3-di-O-methyl-α,β-D-glucopyranose trichloroacetimidate (47)

(a) A solution of glycoside 46 (400 mg, 0.133 mmol) in a 2/1 trifluoroacetic acid/dichloromethane mixture (2 ml) is stirred for 1.5 hours (TLC). The solution is diluted in a 2/1 toluene/n-propyl acetate mixture (12 ml), concentrated and coevaporated with toluene (5×10 ml). The residue is purified (4/3 acetone/cyclohexane) in order to obtain a solid (364 mg).

(b) The solid obtained above is dissolved in dichloromethane (2.5 ml). Caesium carbonate (65 mg, 0.200 mmol) and trichloroacetonitrile (63 ml, 0.620 mmol) are added and the mixture is stirred for 2.5 hours and then filtered (Celite), concentrated and purified on a column of silica (50/50/0.1 cyclohexane/acetone/triethylamine) in order to obtain the imidate 47 (348 mg, 86%). [α]$_D$+185 (c=0.91, dichloromethane). ESIMS, positive mode: monoisotopic mass=3044.1, chemical mass=3047.3, experimental mass=3046.9±0.2 a.m.u. $^1$H NMR (CD$_2$Cl$_2$) δ 8.61, 8.58 (2s, 1H, α and β N:H), 6.35 (d, J=3.7 Hz, H-1a unit R), 5.59, (d, J=7.5 Hz, H-1b unit R), 5.38 (d, J=3.8 Hz, H-1 unit NR), 5.32–5.25 (m, 10H, H-1), 2.64–2.40 (m, 4H, O(C:O)CH$_2$CH$_2$(C:O)CH$_3$), 2.02, 1.96, 1.95, 1.94, 1.93, 1.89 (6s, 39H, 12Ac and O(C:O)CH$_2$CH$_2$(C:O)CH$_3$).

Anal. Calculated for C$_{127}$H$_{200}$Cl$_3$NO$_{25}$: C, 50.06; H, 6.61; N, 0.46. Found: C, 49.93; H, 6.52; N, 0.42.

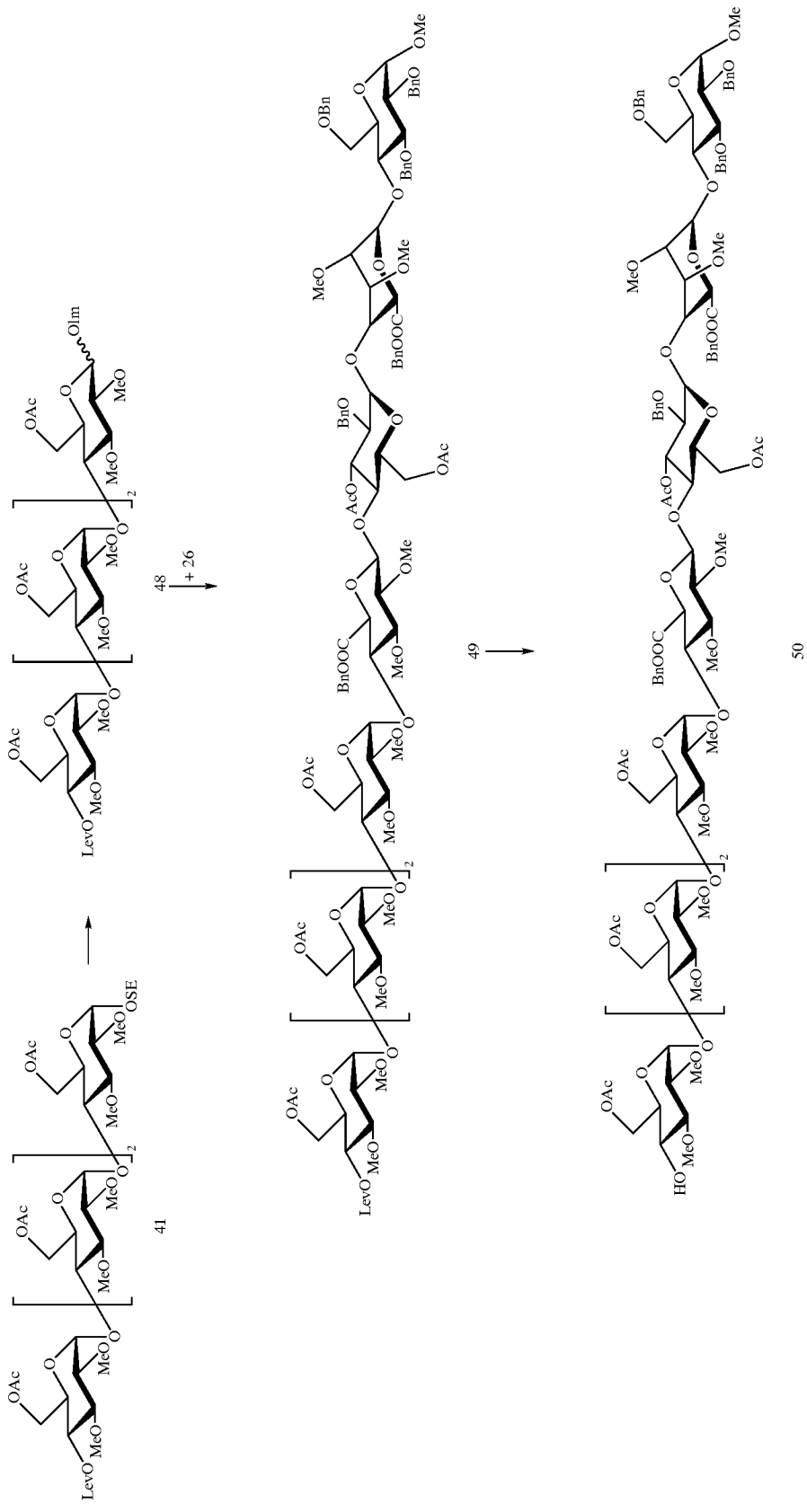
SCHEME 14
Synthesis of oligosaccharide 50

PREPARATION 45

(6-O-Acetyl-4-O-levulinyl-2,3-di-O-methyl-α-D-gluco-pyranosyl)-(1-4)-[O-(6-O-acetyl-2,3-di-O-methyl-α-D-glucopyranosyl)-(1-4)-]$_2$-6-O-acetyl-2,3-di-O-methyl-α,β-D-glucopyranose trichloroacetimidate (48)

Compound 41 (200 mg, 0.174 mmol) is treated according to Preparation 44. The reaction mixture is purified on a column of silica (3/2 toluene/acetone) in order to obtain the imidate 48 (230 mg, 77%). ESIMS, positive mode: m/z, +NaCl, 1210 (M+Na)$^+$; +KF, 1226 (M+K)$^+$. $^1$H NMR (CDCl$_3$) δ 8.66–8.64 (2s, 1H, α and β N:H), 6.51 (d, J=3.6 Hz, H-1β), 5.71 (d, J=7.5 Hz, H-1β), 2.90–2.52 (m, 4H, O(C:O)CH$_2$CH$_2$(C:O)CH$_3$), 2.17, 2.11, 2.11, 2.09, 2.05 (5s, 4Ac and O(C:O)CH$_2$CH$_2$)(C:O) CH$_3$).

PREPARATION 46

Methyl O-(6-O-Acetyl-4-O-levulinyl-2,3-di-O-methyl-(α-D-glucopyranosyl)-(1-4)-[O-(6-O-acetyl-2,3-di-O-methyl-α-D-glucopyranosyl)-(1-4)-]$_2$-6-O-(benzyl-2,3-di-O-methyl-O-β-D-glucopyranosyluronate)-(1-4)-O-(3,6-di-O-acetyl-2-O-benzyl-α-D-glucopyranosyl)-(1-4)-O-(benzyl-2,3-di-O-methyl-(α-L-ido-pyranosyluronate)-(1-4)-2,3,6-tri-O-benzyl-α-D-glucopyranoside (49)

The imidate 48 (73 mg, 0.061 mmol) and the glycosyl acceptor 26 (82 mg, 0.059 mmol) are treated according to Preparation 39. The compound is purified on a Sephadex® LH-20 chromatography column (1/1 dichloromethane/ethanol) and then on a column of silica (3/1 toluene/acetone) to give the derivative 49 (98 mg, 69%). [α]$_D$+95 (c=1.01, dichloromethane). ESIMS, positive mode: monoisotopic mass=2414.97, chemical mass=2416.97, experimental mass=2416.2. $^1$H NMR (CDCl$_3$) δ 7.43–7.20 (m, 30H, 6Ph), 5.55 (d, J=3.9 Hz, H-1 unit NR), 5.50 (d, J=3.9 Hz, H-1 unit NR-3), 5.44, 5.38 (2d, J=3.7 and 3.9 Hz, H-1 unit NR-1, unit NR-2), 5.29 (d, J=6.8 Hz, H-1 unit R-1), 5.17 (d, J=3.5 Hz, H-1 unit R-2), 4.56 (d, J=3.7 Hz, H-1 unit R), 4.10 (d, J=7.9 Hz, H-1 unit R-3), 2.81–2.50 (m, 4H, O(C:O)CH$_2$CH$_2$(C:O) CH$_3$), 2.17, 2.15, 2.11, 2.09, 2.05, 2.00 (7s, 21H, 6Ac and O(C:O)CH$_2$CH$_2$(C:O)CH$_3$).

Anal. Calculated for C$_{120}$H$_{158}$Cl$_3$O$_{51}$: C, 59.63; H, 6.59. Found: C, 59.23; H, 6.58.

PREPARATION 47

Methyl[O-(6-O-Acetyl-2,3-di-O-methyl-α-D-glucopyrano-syl)-(1-4)-]$_3$-O-(benzyl-2,3-di-O-methyl-,-D-glucopyrano-syluronate)-(1-4)-O-(3,6-di-O-acetyl-2-O-benzyl-α-D-glucopyranosyl)-(1-4)-O-(benzyl-2,3-di-O-methyl-α-L-idopyranosyluronate)-(1-4)-2,3,6-tri-O-benzyl-α-D-glucopyranoside (50)

The octasaccharide 49 (120 mg, 0.050 mmol) is reacted as in Preparation 37. The residue is purified on a column of silica (3/1 toluene/acetone) in order to obtain compound 50 (95 mg, 83%). [α]$_D$+80 (C=0.62, dichloromethane). ESIMS, positive mode: monoisotopic mass=2316.9, chemical mass=2318.4, experimental mass=2318.2±0.4 a.m.u. $^1$H NMR (CDCl$_3$) δ 7.42–7.12 (m, 30H, 6Ph), 5.50, 5.46, 5.43, 5.40 (d, J=3.9, 3.9, 3.7, 3.7 Hz, H-1 unit NR, unit NR-1, unit NR-2, unit NR-3), 2.14, 2.10, 2.09, 2.08, 2.00, 1.88 (6s, 18H, 6Ac).

Anal. Calculated for C$_{115}$H$_{152}$O$_{49}$: C, 59.57; H, 6.60. Found: C, 59.49; H, 6.61.

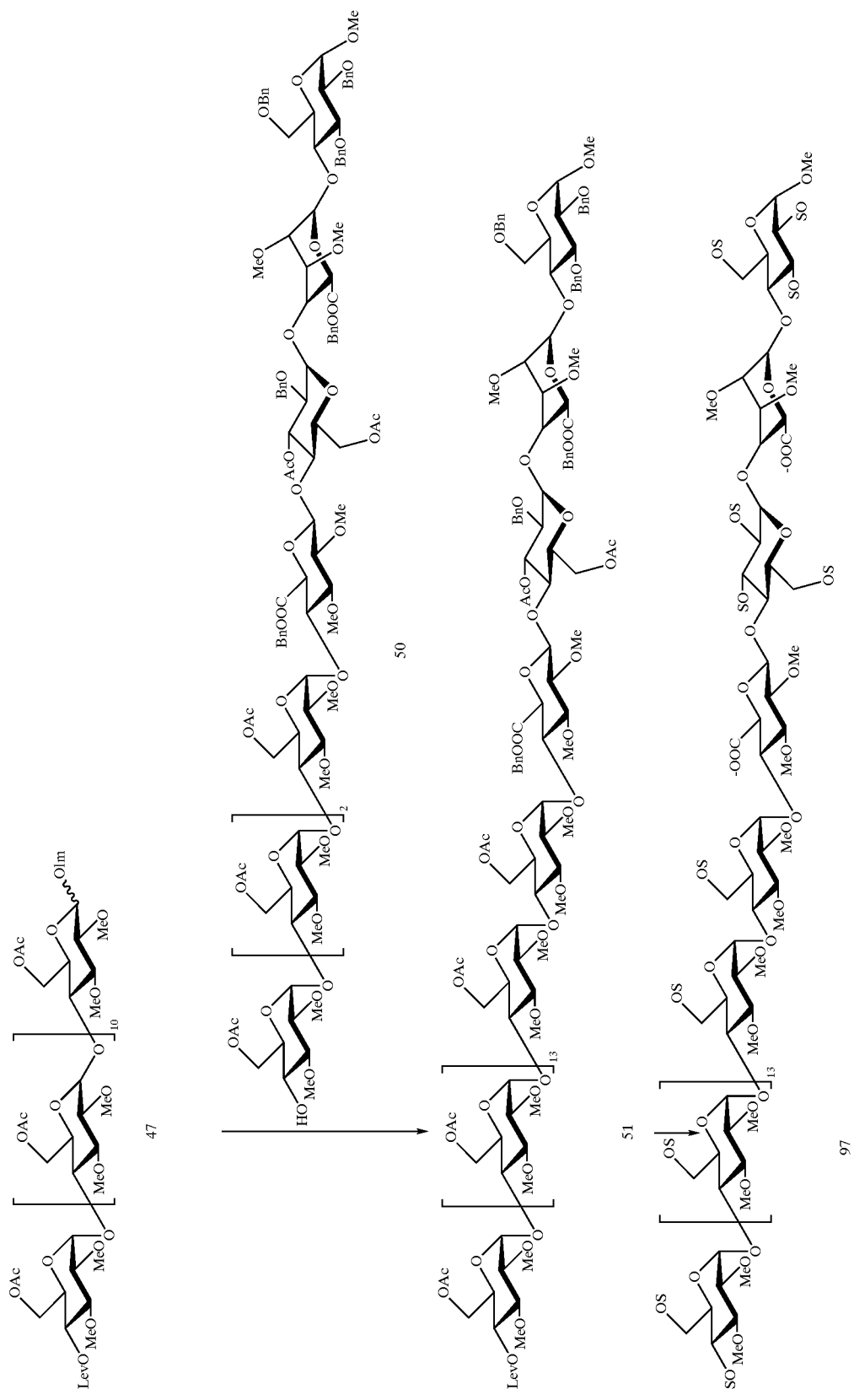
SCHEME 15
Synthesis of polysaccharide 97 (Example 4)

PREPARATION 48

Methyl O-(6-O-Acetyl-4-O-levulinyl-2,3-di-O-methyl-α-D-glucopyranosyl)-(1-4)-[O-(6-O-acetyl-2,3-di-O-methyl-α-D-glucopyranosyl)-(1-4)-]$_{15}$-O-(benzyl-2,3-di-O-methyl-β-D-glucopyranosyluronate)-(1-4)-O-(3,6-di-O-acetyl-2-O-benzyl-α-D-glucopyranosyl)-(1-4)-O-(benzyl-2,3-di-O-methyl-α-L-ido-pyranosyluronate)-(1-4)-2,3,6-tri-O-benzyl-α-D-glucopyranoside (51)

The imidate 47 (84 mg, 0.027 mmol) is treated with the glycosyl acceptor 50 (62 mg, 0.027 mmol) according to Preparation 39. The residue is first purified on a column of Toyopearl® HW-40 and then on a column of silica (1/1 cyclohexane/acetone) in order to obtain the derivative 51 (71 mg, 51% not optimized). [α]$_D$+136 (c=0.95, dichloromethane). ESIMS, positive mode: monoisotopic mass=5200.11, chemical mass 5203.39, experimental mass=5203.5. $^1$H NMR (CDCl$_3$) δ 7.42–7.18 (m, 30H, 6Ph), 5.54 (d, J=3.8 Hz, H-1 unit NR), 5.51–5.40 (m, 15 H-1), 5.30 (d, J=6.8 Hz, H-1 unit R-1), 5.17 (d, J=3.5 Hz, H-1 unit R-2), 4.56 (d, J=3.7 Hz, H-1 unit R), 4.09 (d, J=7.9 Hz, H-1 unit R-3), 2.85–2.53 (m, 4H, O(C:O)CH$_2$CH$_2$(C:O)CH$_3$), 2.17, 2.16, 2.13, 2.11, 2.08, 2.05, 2.00, 1.88 (8s, 57H, 18Ac and O(C:O)CH$_2$CH$_2$(C:O)CH$_3$).

Anal. Calculated for C$_{240}$H$_{350}$O$_{123}$. 4H$_2$O: C, 54.64; H, 6.84. Found: C, 54.51; H, 6.79.

PREPARATION 49

Ethyl O-(4,6-O-p-Methoxybenzylidene-α-D-glucopyrano-syl)-(1-4)-1-thio-β-D-glucopyranoside (53)

Anisaldehyde dimethyl acetal (35.8 ml, 0.21 mol) and camphorsulphonic acid (4.44 g, 19.1 mmol) are added, at +5° C. and under argon, to a solution of compound 52 (73.89 g, 0.19 mmol) (W. E. Dick Jr et J. E. Hodge, Methods in Carbohydrate Chemistry, 7, 1976, 15–18) in a 3.5/1 acetonitrile/N,N-dimethylformamide mixture (990 mmol). After stirring for 1.5 hours at room temperature, the mixture is neutralized by addition of triethylamine (2.96 ml, 21.0 eq.). The mixture is concentrated and the syrup is purified on a column of silica (100/0 and then 50/50 dichloromethane/methanol) in order to obtain 53 (58.6 g, 61%, not optimized) [α]$_D$+47 (c=1.03, methanol). ESIMS, positive mode: m/z, 503 (M-H)$^-$. $^1$H NMR (CD$_3$OD) δ 7.41, 6.89 (2d, 4H, CH$_3$OC$_6$H$_4$), 5.51 (s, CHC$_6$CH$_4$), 5.20 (d, J=3.6 Hz, H-1'), 4.39 (d, J 7.1 Hz, H-1), 3.78 (s, 3H, CH$_3$OC$_6$H$_4$), 2.75 (q, 2H, J 7.0 Hz, SCH$_2$CH$_3$), 1.29 (t, 3H, SCH$_2$CH$_3$).

Anal. Calculated for C$_{22}$H$_{32}$O$_{11}$S: C, 52.37; H, 6.39; S, 6.35. Found: C, 52.15; H, 6.61; S, 5.84.

PREPARATION 50

Ethyl O-(2,3-di-O-Acetyl-4,6-p-methoxybenzylidene-α-D-glucopyranosyl)-(1-4)-2,3,6-tri-O-acetyl-1-thio-β-D-glucopyranoside (54)

Triethylamine (65 ml, 0.47 mol) and acetic anhydride (89 ml, 0.94 mol) are added dropwise, at 0° C., to a suspension SCHEME16
Synthesis of disaccharide 57

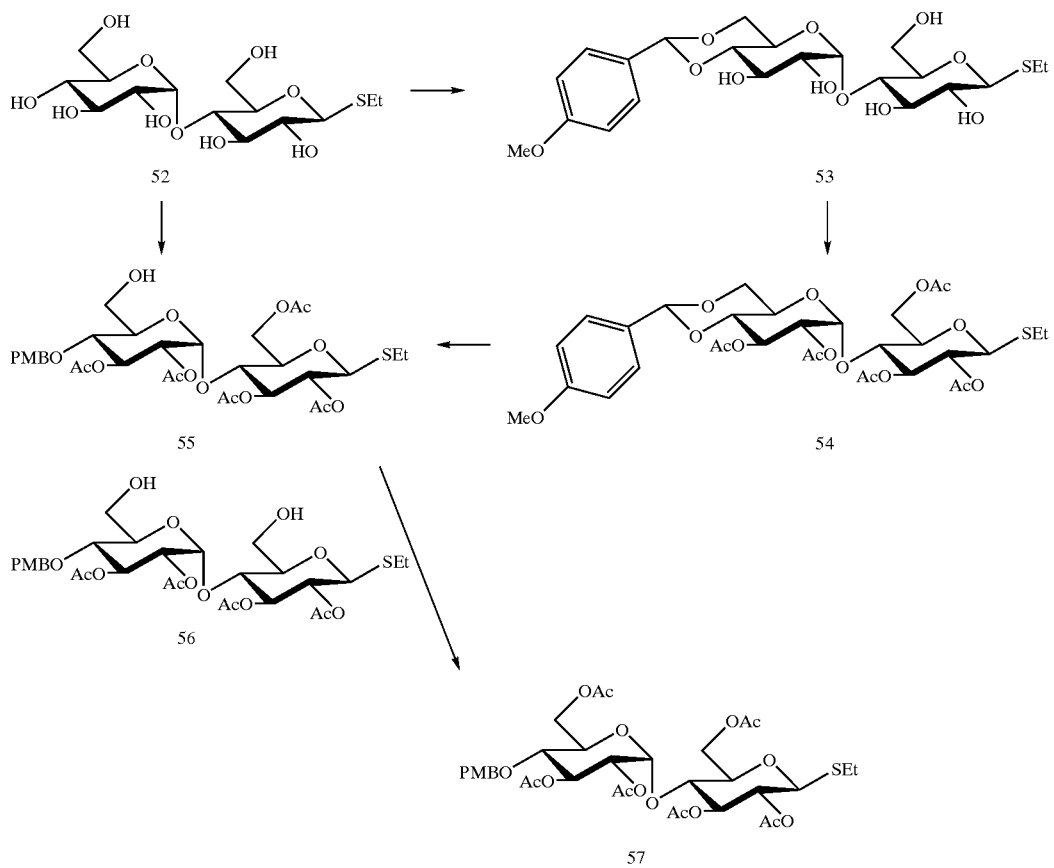

of 53 (47.22 g, 93.6 mmol) in dichloromethane (450 ml). 4-Dimethylaminopyridine (5.71 g, 46.8 mmol) is then added and the mixture is left stirring for 1.5 hours at room temperature. The reaction is stopped by addition of methanol (45 ml, 1.12 mol) and then washed successively with cold aqueous 10% potassium hydrogen sulphate solution, water, saturated sodium hydrogen carbonate solution and water. The solution is dried, concentrated and crystallized (cyclohexane/ethyl acetate) in order to obtain 54 (64.9 g, 97%). $[\alpha]_D$+21 (c=1.00, dichloromethane). pf 213–215° C. ESIMS, positive mode: m/z+NaCl, 737 (M+Na)$^+$, +KF, 753 (M+K)$^+$. $^1$H NMR (CDCl$_3$) δ 7.34, 6.86 (2d, 4H, CH$_3$OC$_6$H$_4$), 5.43 (s, CHC$_6$H$_4$), 5.34 (d, J=4.1 Hz, H-1'), 4.54 (d, J=9.9 Hz, H-1), 3.78 (s, 3H, CH$_3$OC$_6$H$_4$), 2.74–2.60 (m, 2H, SCH$_2$CH$_3$), 2.10, 2.06, 2.03, 2.01 (4s, 15H, 5Ac), 1.26 (t, 3H, SCH$_2$CH$_3$).

Anal. Calculated for $C_{32}H_{42}O_{16}S$: C, 53.78; H, 5.92; S, 4.49. Found: C, 53.74; H, 6.08; S, 4.40.

PREPARATION 51

Ethyl O-(2,3-di-O-Acetyl-4-p-methoxybenzyl-α-D-gluco-pyranosyl)-(1-4)-2,3,6-tri-O-acetyl-1-thio-β-D-gluco-pyranoside (55) and ethyl O-(2,3-di-O-acetyl-4-p-methoxybenzyl-α-D-glucopyranosyl)-(1-4)-2,3-di-O-acetyl-1-thio-β-D-glucopyranoside (56)

A suspension of 54 (25.0 g, 35.0 mmol), borane/trimethylamine complex (20.4 g, 0.28 mol) and molecular sieves (33 g, 4Å) is stirred for 1 hour under argon in toluene (810 ml). The mixture is cooled to 0° C. and aluminium chloride (14.0 g, 0.11 mol) is added slowly. The reaction medium is stirred for 25 minutes (TLC), poured into cold, aqueous 20% potassium hydrogen sulphate solution, stirred for 1 hour at 0° C. and then filtered (Celite). The organic phase is washed with water, with aqueous 2% sodium hydrogen carbonate solution, with water, dried and concentrated. The residue is purified on a column of silica in order to obtain 55 (7.37 g, 29%, not optimized) and 56 (1.36 g, 6%). An analytical sample of 55 is crystallized from a cyclohexane/ethyl acetate mixture. $[\alpha]_D$+30 (c=1.00, dichloromethane). m.p. 151–153° C. ESIMS, positive mode: m/z, +NaCl, 739 (M+Na)$^+$, +KF, 755 (M+K)$^+$. $^1$H NMR (CDCl$_3$) δ 7.19, 6.87 (2d, 4H, CH$_3$OC$_6$H$_4$), 5.36 (d, J=3.5 Hz, H-1'), 4.54 (s, 2H, C$_6$H$_4$CH$_2$), 4.53 (d, J=9.0 Hz, H-1), 2.70–2.65 (m, 2H, SCH$_2$CH$_3$).

Anal. Calculated for $C_{32}H_{42}O_{16}S$: C, 53.62; H, 6.19; S, 4.47. Found: C, 53.57; H, 6.21; S, 4.43.

Compound 56: $[\alpha]_D$+19 (c=1.11, dichloromethane). ESIMS, positive mode: m/z+NaCl, 697 (M+Na)$^+$, +KF, 713 (M+K)$^+$. $^1$H NMR (CDCl$_3$) δ 7.17, 6.84 (2d, 4H, CH$_3$OC$_6$CH$_4$), 5.36 (d, J=4.5 Hz, H-1'), 4.54 (d, J=10.1 Hz, H-1), 4.49 (s, 2H, C$_6$H$_4$CH$_2$), 2.69–2.64 (m, 2H, SCH$_2$CH$_3$), 2.02, 2.01, 2.00, 1.96 (4s, 12H, 4Ac), 1.25 (t, 3H, SCH$_2$CH$_3$).

Anal. Calculated for $C_{30}H_{42}O_{15}S$: C, 53.40; H, 6.27; S, 4.75. Found: C, 53.29; H, 6.39; S, 4.53.

PREPARATION 52

Ethyl O-(2,3-tri-O-Acetyl-4-p-methoxybenzyl-α-D-gluco-pyranosyl)-(1-4)-2,3,6-tri-O-acetyl-1-thio-β-D-gluco-pyranoside (57)

Acetic anhydride (1.47 ml, 15.5 mmol) is added, at 0° C., to a mixture of 55 (5.6 g, 7.77 mmol), triethylamine (1.19 ml, 8.54 mmol) and 4-dimethylaminopyridine (190 mg, 1.55 mmol) in dichloromethane (40 ml). After stirring for 40 minutes (TLC) at room temperature, the mixture is diluted with dichloromethane (50 ml) and washed with cold, aqueous 10% potassium hydrogen sulphate solution, water, saturated sodium hydrogen carbonate solution and water. The solution is dried and concentrated and the residue is purified on a column of silica (35/65 ethyl acetate/cyclohexane) in order to obtain 57 (5.66 g, 96%). $[\alpha]_D$+44 (c=1.03, dichloromethane). ESIMS, positive mode: m/z, +NaCl, 781 (M+Na)$^+$, +KF, 797 (M+K)$^+$. $^1$H NMR (CDCl$_3$) δ 7.15, 6.85 (2d, 4H, CH$_3$OC$_6$H$_4$), 5.30 (d, J=4.2 Hz, H-1'), 4.53 (d, J=10.0 Hz, H-1), 2.69–2.64 (m, 2H, SCH$_2$CH$_3$), 2.09, 2.07, 2.04, 2.01, 2.00, 1.98 (6s, 18H, 6Ac), 1.25 (t, 3H, SCH$_2$CH$_3$).

Anal. Calculated for $C_{34}H_{46}O_{17}S$: C, 53.82; H, 6.11; S, 4.22. Found: C, 53.77; H, 6.24; S, 4.09.

SCHEME 17
Synthesis of trisaccharide 62

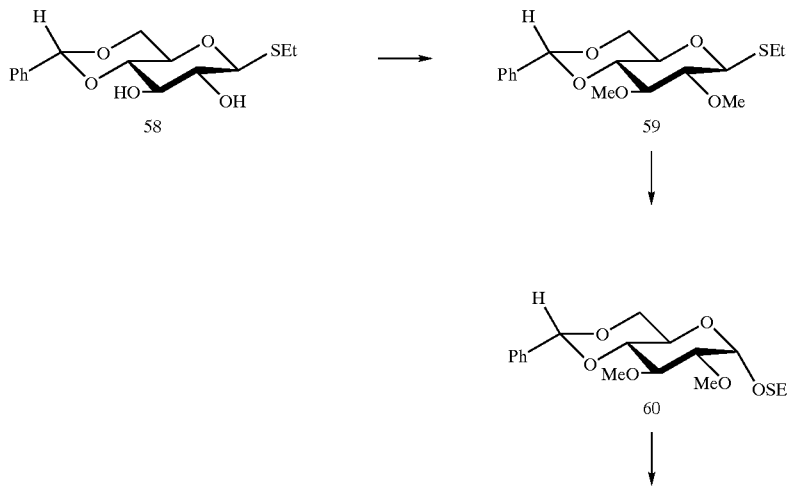

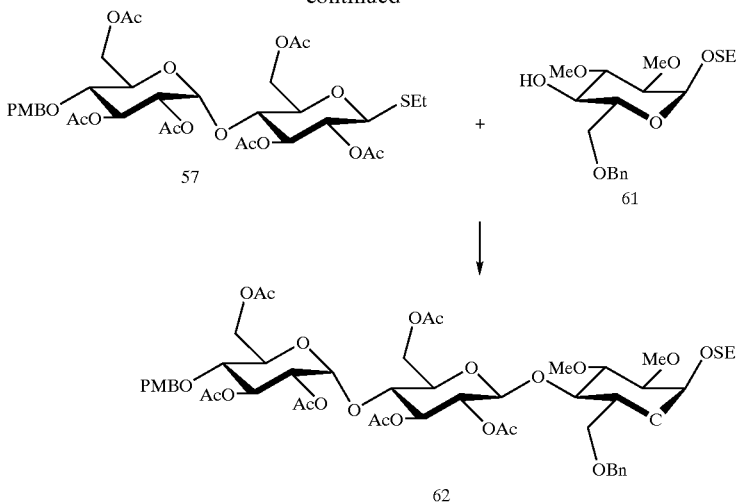

PREPARATION 53

Ethyl 4,6-O-Benzylidene-2,3-di-O-methyl-1-thio-β-D-glucopyranoside (59)

Sodium hydride (500 mg, 19.9 mmol) is added, at 0° C., to a mixture of compound 58 (2.59 g, 8.29 mmol) (A. F. Bochkov et al., Izv. Akad. Nauk SSSR, Ser. Khim. (1968), (1), 179) and methyl iodide (1.70 ml, 19.9 mmol) in N,N-dimethylformamide (25 ml) and the mixture is allowed to return to a temperature of 20° C. The mixture is left stirring for 30 minutes (TLC) and methanol is then added. The mixture is poured into water and extracted with ethyl acetate. The organic phase is washed successively with aqueous 1M sodium thiosulphate solution and water, dried and concentrated. The residue is triturated in ethyl ether in order to obtain 59 (0.42 g, 15%); purification of the mother liquors on a column of silica (12/1 toluene/acetone) followed by crystallization allows an additional fraction of 59 (1.6 g, overall yield: 71%) to be obtained. m.p.: 108° C. $[\alpha]_D$–78 (c=1.00, dichloromethane). LSIMS, positive mode: m/z thioglycerol+NaCl, 363 (M+Na)$^+$; thioglycerol+KF, 379 (M+K)$^+$. $^1$H NMR (CDCl$_3$) δ 7.51–7.33 (m, 5H, Ph), 5.52 (s, 1H, C$_6$H$_5$CH), 4.45 (d, 1H, J=9.8 Hz, H-1), 3.64 (s, 3H, OCH$_3$), 3.62 (s, 3H, OCH$_3$), 2.78–2.68 (m, 2H, SCH$_2$CH$_3$), 1.31 (t, 3H, J=2.7 Hz, SCH$_2$CH$_3$).

Anal. Calculated for C$_{17}$H$_{24}$O$_5$S (340.44): C, 59.98; H, 7.11; S, 9.42. Found: C, 59.91; H, 7.15; S, 8.96.

PREPARATION 54

2-(Trimethylsilyl)ethyl 4,6-O-Benzylidene-2,3-di-O-methyl-α-D-glucopyranoside (60)

Compound 59 (23.0 g, 67.5 mmol) and 2-(trimethylsilyl) ethanol (19.4 ml, 135 mmol) are dissolved in a 2/1 mixture of ethyl ether and dichloromethane (345 ml) and 4 Å molecular sieves (11 g) are added. The mixture is left stirring for 1 hour at 25° C. and N-iodosuccinimide (49.7 g, 220 mmol) is added, followed, at 0° C., by silver triflate (2.20 g, 8.78 mmol). The mixture is left stirring for 20 minutes (TLC), and solid sodium hydrogen carbonate is then added. The mixture is diluted with dichloromethane, filtered through Celite, washed successively with aqueous 1M sodium thiosulphate solution and water, dried and evaporated to dryness. The residue is purified on a column of silica (15/1 and then 5/1 cyclohexane/ethyl acetate) in order to obtain 60β (4.20 g, 15%) and 60α (8.40 g, 31%).

Compound 60α. $[\alpha]_D$+96 (c=0.4, dichloromethane). ESIMS, positive mode: m/z, 419 (M+Na)$^+$; 435 (M+K)$^+$. $^1$H NMR (CDCl$_3$) δ 7.52–7.35 (m, 5H, Ph), 5.54 (s, 1H, C$_6$H$_5$CH), 4.98 (d, 1H, J=3.7 Hz, H-1), 3.64 (s, 3H, OCH$_3$), 3.62 (s,3H, OCH), 1.24–0.96 (m, 2H, OCH$_2$CH$_2$Si(CH$_3$)$_3$), 0.00 (s, 9H, OCH$_2$CH$_2$Si(CH$_3$) 3)

Anal. Calculated for C$_{20}$H$_{32}$O$_6$S (396.56): C, 60.58; H, 8.13. Found: C, 60.26; H, 8.39.

PREPARATION 55

2-(Trimethylsilyl)ethyl 6-O-Benzyl-2,3-di-O-methyl-α-D-glucopyranoside (61)

Compound 60 (21.1 g, 53.3 mmol) is dissolved in dichloromethane (154 ml). Triethylsilane (34 ml, 213 mmol) is added at room temperature, followed by dropwise addition of a mixture of trifluoroacetic acid (16.3 ml, 213 mmol) and trifluoroacetic anhydride (0.49 ml, 3.47 mmol). The mixture is left stirring for 2 hours and aqueous 1M sodium hydroxide solution is added until the pH is basic. After separation of the phases by settling, the aqueous phase is extracted with ethyl acetate and the organic phases are then combined, dried and concentrated. The residue is purified on a column of silica (14/1 and then 12/1 dichloromethane/acetone) in order to obtain 61 (12.5 g, 59%). $[\alpha]_D$+100 (c=1.45, dichloromethane). $^1$H NMR δ 7.40–7.20 (m, 5H, Ph), 4.98 (d, 1H, J=3.5 Hz, H-1), 3.62 (s, 3H, OCH$_3$), 3.49 (s, 3H, OCH$_3$), 1.14–0.91 (m, 2H, CH$_2$CH$_2$Si(CH$_3$)$_3$), 0.00 (s, 9H, CH$_2$CH$_2$Si(CH$_3$)$_3$)

Anal. Calculated for C$_{20}$H$_{30}$O$_6$Si(398.58): C, 60.27; H, 8.60. Found: C, 60.18; H, 8.81.

PREPARATION 56

2-(Trimethylsilyl)ethyl O-(2,3,6-tri-O-Acetyl-4-O-p-methoxybenzyl-α-D-glucopyranosyl)-(1-4)-O-(2,3,6-tri-O-acetyl-β-D-glucopyranosyl-(1-4)-6-O-benzyl-2,3-di-O-methyl-α-D-glucopyranoside (62)

A mixture of thioglycoside 57 (19.1 g, 25.1 mmol) and the glycosyl acceptor 61 (7.5 g, 18.7 mmol) is treated according to Method 3 in order to obtain, after purification on a column of silica (20/1 and then 10/1 dichloromethane/acetone), 62 (19.7 g, 95%). $[\alpha]_D$+90 (c=1.15, dichloromethane).

Anal. Calculated for C$_{52}$H$_{74}$O$_{23}$Si(1095.24): C, 57.03; H, 6.81. Found: C, 57.38; H, 6.85.

SCHEME 18
Synthesis of oligosaccharide 66

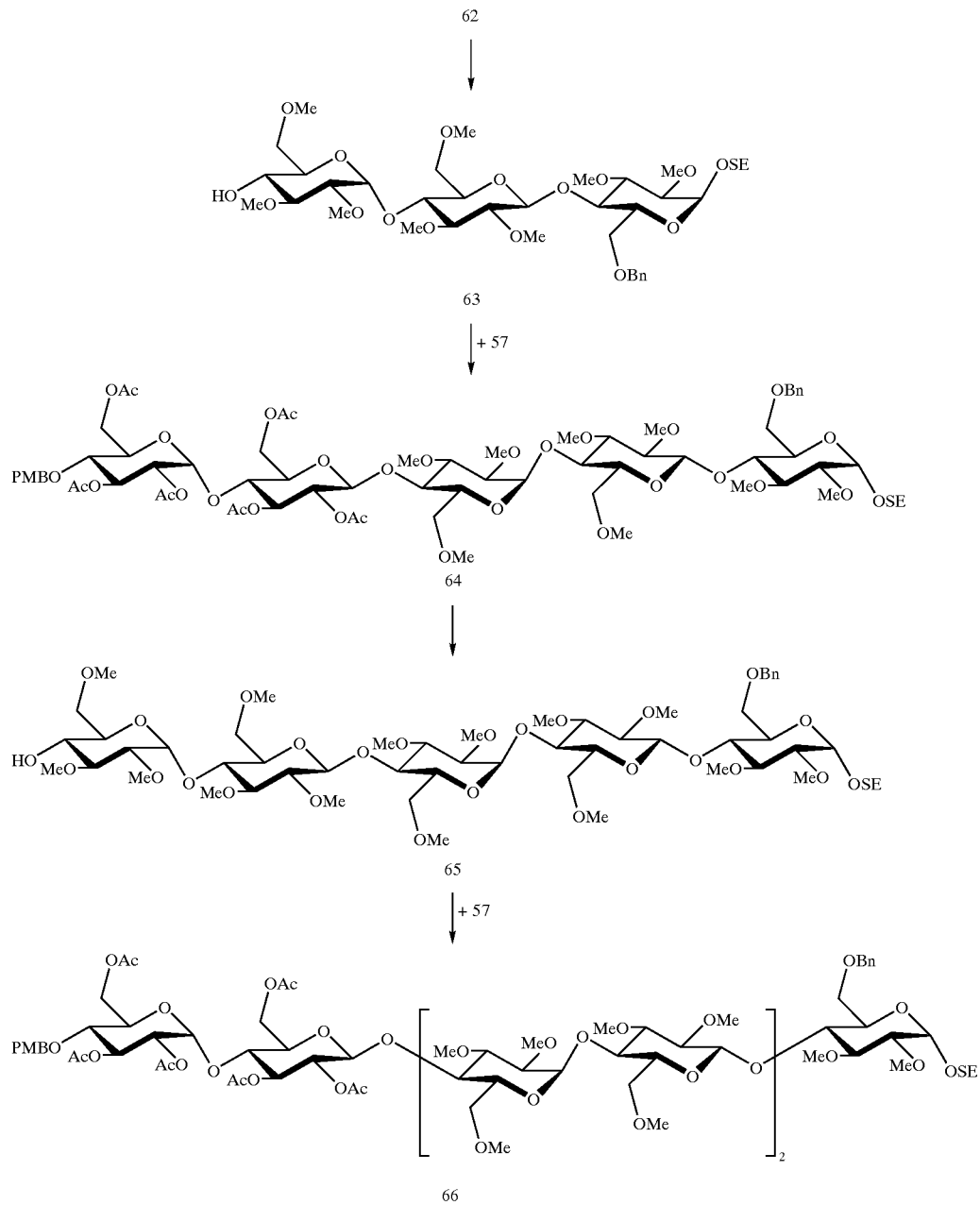

PREPARATION 57

2-(Trimethylsilyl)ethyl O-(2,3,6-tri-O-Methyl-α-D-glucopyranosyl)-(1-4)-O-(2,3,6-tri-O-methyl-β-D-glucopyranosyl)-(1-4)-6-O-benzyl-2,3-di-O-methyl-α-D-glucopyranoside (63)

Compound 62 (19.7 g, 18.0 mmol) is treated according to method 4 in order to obtain, after purification on a column of silica (3/1 and then 2/1 toluene/acetone), compound 63 (11.2 g, 79% over the three steps). $[\alpha]_D$+95 (c=1.15, dichloromethane) ESIMS, positive mode: m/z +NaCl, 829 (M+Na)$^+$; +KF, 845 (M+K)$^+$. $^1$H NMR (CDCl$_3$) δ 7.34–7.25 (m, 5H, Ph), 5.60 (d, 1H, J=3.8 Hz, H-1"), 4.96 (d, 1H, J=3.8 Hz, H-1, 4.29 (d, 1H, J=8.0 Hz, H-1'), 1.08–0.91 (m, 2H, CH$_2$CH$_2$Si(CH$_3$)$_3$, 0.00 (s, 9H, CH$_2$CH$_2$Si(CH$_3$)$_3$.

PREPARATION 58

2-(Trimethylsilyl)ethyl O-(2,3,6-tri-O-Acetyl-4-O-p-methoxybenzyl-α-D-glucopyranosyl)-(1-4)-O-(2,3,6-tri-O-acetyl-β-D-glucopyranosyl)-(1-4)-O-(2,3,6-tri-O-methyl-α-D-glucopyranosyl)-(1-4)-O-(2,3,6-tri-O-methyl-β-D-glucopyranosyl)-(1-4)-6-O-benzyl-2,3-di-O-methyl-α-D-glucopyranoside (64)

A mixture of thioglycoside 57 (6.87 g, 9.10 mmol) and the glycosyl acceptor 63 (6.67 g, 8.30 mmol) is treated according to Method 3 and the residue is purified on a column of silica (2/5 toluene/acetone) in order to obtain 64 (10.7 g, 86%). $[\alpha]_D$+90 (C=0.83, dichloromethane). ESIMS, positive mode: m/z+NaCl, 1525 (M+Na)$^+$; +KF, 1541 (M+K)$^+$. $^1$H NMR (CDCl$_3$) δ 7.33–7.25 (m, 5H, Ph), 7.15–6.84 (m, 4H, C$_6$H$_4$OCH$_3$), 5.56 (d, 1H, J=3.9 Hz, H-1"), 5.29 (d, 1H, J=4.0 Hz, H-1""), 4.97 (d, 1H, J=8.1 Hz, H-1'''), 4.27 (d, 1H, J=7.9 Hz, H-1'), 1.08–0.91 (m, 2H, CH$_2$CH$_2$Si(CH$_3$)$_3$), 0.00 (s, 9H, CH$_2$CH$_2$Si(CH$_3$)$_3$).

Anal. Calculated for C$_{70}$H$_{106}$O$_{33}$Si(1503.69): C, 55.91; H, 7.11. Found: C, 56.05; H, 7.24.

PREPARATION 59

2-(Trimethylsilyl)ethyl [O-(2,3,6-tri-O-Methyl-α-D-glucopyranosyl)-(1-4)-O-(2,3,6-tri-O-methyl-β-D-glucopyranosyl-(1-4)]$_2$-6-O-benzyl-2,3-di-O-methyl-α-D-glucopyranoside (65)

Compound 64 (10.7 g, 7.2 mmol) is treated according to Method 4 and the residue is purified on a column of silica (2/1 and then 6/5 toluene/acetone) in order to obtain 65 (6.50 g, 74% over the three steps). $[\alpha]_D$+102 (c=0.68, dichloromethane). $^1$H NMR (CDCl$_3$) δ 7.33–7.25 (m, 5H, Ph), 5.65 (d, 1H, J=3.8 Hz H-1""), 5.62 (d, 1H, J=3.8 Hz, H-1"), 4.98 (d, 1H, J=3.7 Hz, H-1), 4.31 (d, 1H, J=8.1 Hz, H-1'"), 4.29 (d, 1H, J=7.9 Hz, H-1'), 1.08–0.91 (m, 2H, CH$_2$CH$_2$Si(CH$_3$)$_3$), 0.00 (s, 9H, CH$_2$CH$_2$Si(CH$_3$)$_3$).

Anal. Calculated for C$_{56}$H$_{98}$O$_{26}$Si(1215.48): C, 55.34; H, 8.13. Found: C, 55.31; H, 8.19.

PREPARATION 60

2-(Trimethylsilyl)ethyl O-(2,3,6-tri-O-Acetyl-4-O-p-methoxybenzyl-α-D-glucopyranosyl)-(1-4)-O-2,3,6-tri-O-acetyl-β-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_2$-6-O-benzyl-2,3-di-O-methyl-α-D-glucopyranoside (66)

A mixture of thioglycoside 57 (4.03 g, 5.31 mmol) and the glycosyl acceptor 65 (5.78 g, 4.75 mmol) is treated according to Method 3 and the residue is purified on a column of silica (2/5 toluene/acetone) in order to obtain 66 (8.63 g, 95 ) $[\alpha]_D$+94 (c=0.74, dichloromethane). ESIMS, positive mode: monoisotopic mass=1910.83, chemical mass=1912.14, experimental mass=1911.61±0.12 a.m.u. $^1$H NMR (CDCl$_3$) δ 7.33–7.25, (m, 5H, Ph), 7.15–6.83 (m, 4H, C$_6$H$_4$OCH$_3$), 5.62 (d, 1H, J=3.8 Hz, H-1 unit R-2), 5.60 (d, 1H, J=3.8 Hz, H-1 unit NR-2), 5.30 (d, 1H, J=4.0 Hz, H-1 unit NR), 4.98 (d, 1H, J=3.7 Hz, H-1 unit R), 4.71 (d, 1H, J=7.9 Hz, H-1 unit NR-1), 4.30 (d, 1H, J=8.1 Hz, H-1 unit C), 4.29 (d, 1H, J=8.4 Hz, H-1 unit R-1), 2.08 (s, 3H, Ac), 2.07 (s, 3H, Ac), 2.03 (s, 3H, Ac), 1.99 (s, 3H, Ac), 1.98 (s, 3H, Ac), 1.96 (s, 3H, Ac), 1.08–0.91 (m, 2H, CH$_2$CH$_2$Si(CH$_3$)$_3$), 0.00 s, 9H, CH$_2$CH$_2$Si(CH$_3$)$_3$)

Anal. Calculated for C$_{88}$H$_{138}$O$_{43}$Si(1912.14): C, 55.28; H, 7.27. Found: C, 55.61; H, 7.35.

75 76
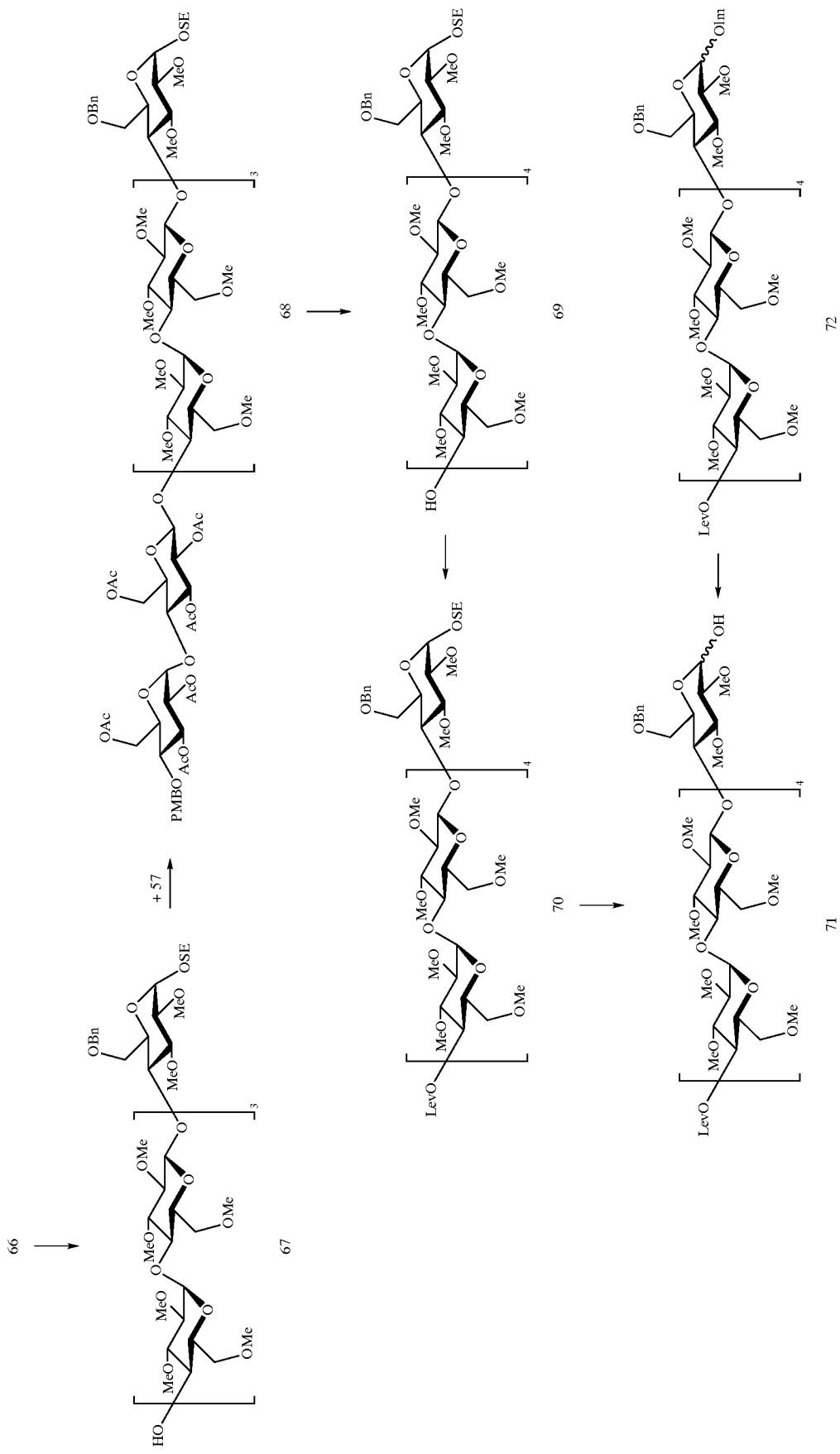
SCHEME 19
Synthesis of oligosaccharide 72

PREPARATION 61

2-(Trimethylsilyl)ethyl [O-(2,3,6-tri-O-Methyl-α-D-glucopyranosyl)-(1-4)-O-(2,3,6-tri-O-methyl-β-D-glucopyranosyl-(1-4)]$_3$-6-O-benzyl-2,3-di-O-methyl-α-D-glucopyranoside (67)

Compound 66 (8.63 g, 4.50 mmol) is treated according to Method 4 and the residue is purified on a column of silica (3/2 and then 4/3 toluene/acetone) in order to obtain 67 (5.67 g, 77% over the three steps). [α]$_D$+102 (c=0.70, dichloromethane). LSIMS, positive mode: m/z thioglycerol+NaCl, 1645.9 (M+Na)$^+$. $^1$H NMR (CDCl$_3$) δ 7.33–7.32 (m, 5H, Ph), 5.65 (d, 2H, J=3.8 Hz, H-1 unit NR and H-1 unit NR-2), 5.62 (d, 1H, J=3.8 Hz, H-1 unit R-2), 4.98 (d, 1H, J=3.7 Hz, H-1 unit R), 4.31 (d, 1H, J=8.1 Hz, H-1 unit NR-1), 4.30 (d, 1H, J=7.9 Hz, H-1 unit C), 4.29 (d, 1H, J=7.9 Hz, H-1 unit R-1), 1.08–0.91 (m, 2H, CH$_2$CH$_2$Si(CH$_3$)$_3$) 0.00 (s, 9H, CH$_2$CH$_2$Si(CH$_3$)$_3$).

Anal. Calculated for C$_{74}$H$_{130}$O$_{36}$Si(1912.14): C, 54.73; H, 8.07. Found: C, 54.61; H, 8.07.

PREPARATION 62

2-(Trimethylsilyl)ethyl O-(2,3,6-tri-O-Acetyl-4-O-p-methoxybenzyl-α-D-glucopyranosyl)-(1-4)-O-(2,3,6-tri-O-acetyl-β-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_3$-6-O-benzyl-2,3-di-O-methyl-α-D-glucopyranoside (68)

A mixture of thioglycoside 57 (1.47 g, 1.95 mmol) and the glycosyl acceptor 67 (2.89 g, 1.77 mmol) is treated according to Method 3. The residue is filtered on a column of silica (3/2 cyclohexane/acetone) in order to obtain 68 (3.71 g, 92%). An analytical sample is purified on a column of silica (3/2 toluene/acetone). [α]$_D$+99 (c=0.58, dichloromethane); ESIMS, positive mode: monoisotopic mass=2319.03, chemical mass=2320.59, experimental mass=2319.03±0.12 a.m.u. $^1$H NMR (CDCl$_3$) δ 7.33–7.32, (m, 5H, Ph), 7.15–6.83 (m, 4H, C$_6$H$_4$OCH$_3$), 5.62 (d, 1H, J=3.8 Hz, H-1 unit R-2), 5.60 (d, 2H, J=3.8 Hz, H-1 unit NR-2 and unit C), 5.29 (d, 1H, J=4.0 Hz, H-1 unit NR), 4.97 (d, 1H, J=3.7 Hz, H-1 unit R), 4.70 (d, 1H, J=7.9 Hz, H-1 unit NR-1), 4.30 (d, 2H, J=8.1 Hz, H-1 unit NR-3 and unit R-3), 4.29 (d, 1H, J=7.9 Hz, H-1 unit R-1), 2.08 (s, 3H, Ac), 2.06 (s, 3H, Ac), 2.02 (s, 3H, Ac), 1.99 (s, 3H, Ac), 1.98 (s, 3H, Ac), 1.96 (s, 3H, Ac), 1.08–0.91 (m, 2H, CH$_2$CH$_2$Si(CH$_3$)$_3$), 0.00 (s, 9H, CH$_2$CH$_2$Si(CH$_3$)$_3$).

Anal. Calculated for C$_{106}$H$_{170}$O$_{53}$Si(2320.59): C, 54.86; H, 7.38. Found: C, 54.76; H, 7.45.

PREPARATION 63

2-(Trimethylsilyl)ethyl [O-(2,3,6-tri-O-Methyl-α-D-glucopyranosyl)-(1-4)-O-(2,3,6-tri-O-methyl-β-D-glucopyranosyl-(1-4)]$_4$-6-O-benzyl-2,3-di-O-methyl-α-D-glucopyranoside (69)

Compound 68 (3.61 g, 1.55 mmol) is treated according to Method 4 and the residue is then purified on a column of silica (4/5 toluene/acetone) in order to obtain 69 (2.22 g, 70% over the three steps). [α]$_D$+103 (c=0.80, dichloromethane). ESIMS, positive mode: monoisotopic mass=2031.01, chemical mass=2032.38, experimental mass=2032.38 a.m.u. $^1$H NMR (CDCl$_3$) δ 7.33–7.32 (m, 5H, Ph), 5.65 (d, 1H, J=3.8 Hz H-1 unit NR), 5.64 (d, 1H, J=3.8 Hz, H-1 unit NR-2), 5.62 (d, 2H, J=3.8 Hz, H-1 unit C and unit R-2), 4.97 (d, 1H, J=3.7 Hz, H-1 unit R), 4.30 (d, 1H, J=7.9 Hz, H-1 unit NR-1), 4.29 (d, 3H, J=7.9 Hz, H-1 unit R-1, unit R-3 and unit NR-3), 1.08–0.91 (m, 2H, CH$_2$CH$_2$Si(CH$_3$)$_3$), 0.00 (s, 9H, CH$_2$CH$_2$Si(CH$_3$)$_3$)

Anal. Calculated for C$_{92}$H$_{162}$O$_{46}$Si(2032.38): C, 54.37; H, 8.03. Found: C, 54.51; H, 8.04.

PREPARATION 64

2-(Trimethylsilyl)ethyl O-(4-O-levulinyl-2,3,6-tri-O-Methyl-α-D-glucopyranosyl)-(1-4)-O-(2,3,6-tri-O-methyl-β-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_3$-6-O-benzyl-2,3-di-O-methyl-α-D-glucopyranoside (70)

Compound 69 (855 mg, 0.42 mmol) is dissolved in dichloromethane (8 ml) and triethylamine (83 μl, 0.59 mmol), 4-dimethylaminopyridine (5.14 mg, 0.04 mmol) and levulinic anhydride (117 mg, 0.55 mmol) are added at 25° C. After stirring for 2 hours (TLC), dichloromethane is then added and the mixture is washed with aqueous 10% potassium hydrogen sulphate solution and then with water, dried and evaporated to dryness. This compound may be used crude in the following step without carrying out a purification. An analytical sample is purified on a column of silica (5/4 cyclohexane/acetone) to give pure 70. [α]$_D$+101 (c=0.89, dichloromethane). ESIMS, positive mode: monoisotopic mass=2129.05, chemical mass=2130.48, experimental mass=2130.00 a.m.u. $^1$H NMR (CDCl$_3$) δ 7.33–7.32 (m, 5H, Ph), 5.65 (d, 3H, J=3.8 Hz, H-1 unit NR, unit NR-2 and unit C), 5.63 (d, 2H, J=3.8 Hz, H-1 unit R-2), 5.02 (t, 1H, J=10.1 Hz, H-4 unit NR), 4.98 (d, 1H, J=3.7 Hz, H-1 unit R), 4.32 (d, 1H, J=7.9 Hz, H-1 unit NR-1), 4.30 (d, 2H, J=7.9 Hz, H-1 unit NR-3 and unit R-3), 4.29 (d, 1H, J=7.9 Hz, H-1 unit R-1), 2.80–2.50 (m, 4H, O(C:O)CH$_2$CH$_2$(C:O)CH$_3$), 2.18 (s, 3H, O(C:O)CH$_2$CH$_2$(C:O)CH$_3$), 1.08–0.91 (m, 2H, CH$_2$CH$_2$Si(CH$_3$)$_3$), 0.00 (s, 9H, CH$_2$CH$_2$Si(CH$_3$)$_3$).

Anal. Calculated for C$_{97}$H$_{168}$O$_{48}$Si(2032.38): C, 54.69; H, 7.95. Found: C, 54.55; H, 8.07.

PREPARATION 65

O-(4-O-Levulinyl-2,3,6-tri-O-Methyl-α-D-glucopyranosyl)-(1-4)-O-(2,3,6-tri-O-methyl-β-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_3$-6-O-benzyl-2,3-di-O-methyl-α,β-D-glucopyranose (71)

Compound 70 (876 mg, 0.41 mmol) is treated as in Preparation 44 (a). The residue is purified on a column of silica in order to obtain a mixture of isomers (a/b=60/40) of 71 (600 mg, 50% over the two steps). [α]$_D$+89 (c=0.74, dichloromethane). ESIMS, positive mode: monoisotopic mass=2028.97, chemical mass=2030.24, experimental mass=2030.19±0.09 a.m.u. $^1$H NMR (CDCl$_3$) δ 7.33–7.32 (m, 5H, Ph), 5.65 (d, 3H, J=3.8 Hz H-1 unit NR, unit NR-2 and unit C), 5.63 (d, 1H, J=3.8 Hz, H-1 unit R-2), 5.33 (d, 1H, J=3.2 Hz, H-1α unit R), 5.02 (t, 1H, J=10.1 Hz, H-4 unit NR), 4.59 (d, 1H, J=5.3 Hz, H-1β unit R), 4.32 (d, 1H, J=7.9 Hz, H-1 unit NR-1), 4.30 (d, 2H, J=7.9 Hz, H-1 unit NR-3 and unit R-3), 4.29 (d, 1H, J=7.9 Hz, H-1 unit R-1), 2.80–2.50 (m, 4H, O(C:O)CH$_2$CH$_2$(C:O)CH$_3$), 2.18 (s, 3H, C(C:O)CH$_2$CH$_2$(C:O)CH$_3$).

PREPARATION 66

O-(4-O-Levulinyl-2,3,6-tri-O-Methyl-α-D-gluco-pyranosyl)-(1-4)-O-(2,3,6-tri-O-methyl-β-D-gluco-pyranosyl)-(1-4)-[O-(2,3,6-tri-O-methyl-α-D-gluco-pyranosyl)-(1-4)-O-(2,3,6-tri-O-methyl-β-D-gluco-pyranosyl)-(1-4)]$_3$-6-O-benzyl-2,3-di-O-methyl-α,β-D-glucopyranose trichloroacetimidate (72)

To a solution of 71 (593 mg, 0.29 mmol) in dichloromethane (7 ml) are added potassium carbonate (72.2 mg, 0.52 mmol) and trichloroacetonitrile (176 μl, 1.75 mmol). The mixture is left stirring for 16 hours, filtered and evaporated. The residue is filtered through silica gel (5/4 cyclohexane/acetone+1% of triethylamine) in order to obtain a mixture of the anomers (α/β=47/53) of the imidate 72 (414 mg, 46%). [α]$_D$+86 (c=0.84, dichloromethane). $^1$H NMR (CDCl$_3$) δ 7.33–7.32 (m, 5H, Ph), 6.50 (d, 1H, J=3.5 Hz, H-1α unit R), 5.65 (d, 1H, J=8.2 Hz, H-1β, unit R), 5.65 (d, 1H, J=3.8 Hz, H-1 unit NR), 5.64 (d, 2H, J=3.8 Hz, H-1 unit R-2 and unit C), 5.61 (d, 1H, J=3.8 Hz, H-1 unit R-2), 5.02 (t, 1H, J=10.1 Hz, H-4 unit NR), 4.37 (d, 1H, J=7.9 Hz, H-1 unit R-1), 4.30 (d, 3H, J=7.9 Hz, H-1 unit NR-1, unit NR-3 and unit R-3), 2.80–2.50 (m, 4H, O(C:O)CH$_2$CH$_2$(C:O)CH$_3$), 2.18 (s, 3H, O(C:O)CH$_2$CH$_2$(C:O)CH$_3$).

PREPARATION 67

Methyl O-(4-O-Levulinyl-2,3,6-tri-O-methyl-α-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_3$-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-(1-4)-2,3,6-tri-O-benzyl-α-D-glucopyranoside (73)

The glycosyl acceptor 26 (220 mg, 0.16 mmol) and imidate 72 (344 mg, 0.16 mmol) are dissolved in a 1/2 dichloromethane/ethyl ether mixture (5 ml). 4 Å molecular sieves (750 mg/mmol) are added and the mixture is left stirring at 25° C. for 1 hour. The mixture is cooled to −25° C. and a 1M solution of tertbutyldimethylsilyl triflate in dichloromethane (0.20 mol/mol of imidate) is added. After stirring for 15 minutes, solid sodium hydrogen carbonate is then added and the mixture is filtered and concentrated. The residue is placed on a column of Toyopearl® HW-50 (1/1 dichloromethane/ethanol) and the fraction containing the glycosyl acceptor is returned to the reaction and then treated as above. Successive purifications are carried out on a column of silica (5/4 and then 1/1 toluene/acetone) in order to obtain a fraction 73α/β=7/3 (107 mg) and a fraction in 73α/β=9/1 (201 mg) in an overall yield of 57% (308 mg). $^1$H NMR (CDCl$_3$) δ 7.33–7.25 (m, 35H, 7Ph), 5.65 (d, 3H, J=3.5 Hz, H-1 unit A, unit C and unit E), 5.57 (d, 1H, J 3.9 Hz, H-1 unit G), 5.52 (d, 1H, J=3.3 Hz, H-1 unit I), 5.29 (d, 1H, J=6.8 Hz, H-1 unit L), 5.17 (d, 1H, J=3.5 Hz, H-1 unit K), 4.56 (d, 1H, J=3.5 Hz, H-1 unit M), 4.31 (d, 3H, J=7.9 Hz, H-1 unit B, unit D and unit F), 4.27 (d, 1H, J=8.0 Hz, H-1 unit H), 4.08 (d, 1H, J=8.0 Hz, H-1 unit J), 2.80–2.50 (m, 4H, O(C:O)CH$_2$CH$_1$(C:O)CH$_3$), 2.18 (s, 3H, O(C:O)CH$_2$CH$_2$(C:O)CH$_3$), 1.97 (s, 3H, Ac), 1.81 (s, 3H, Ac).

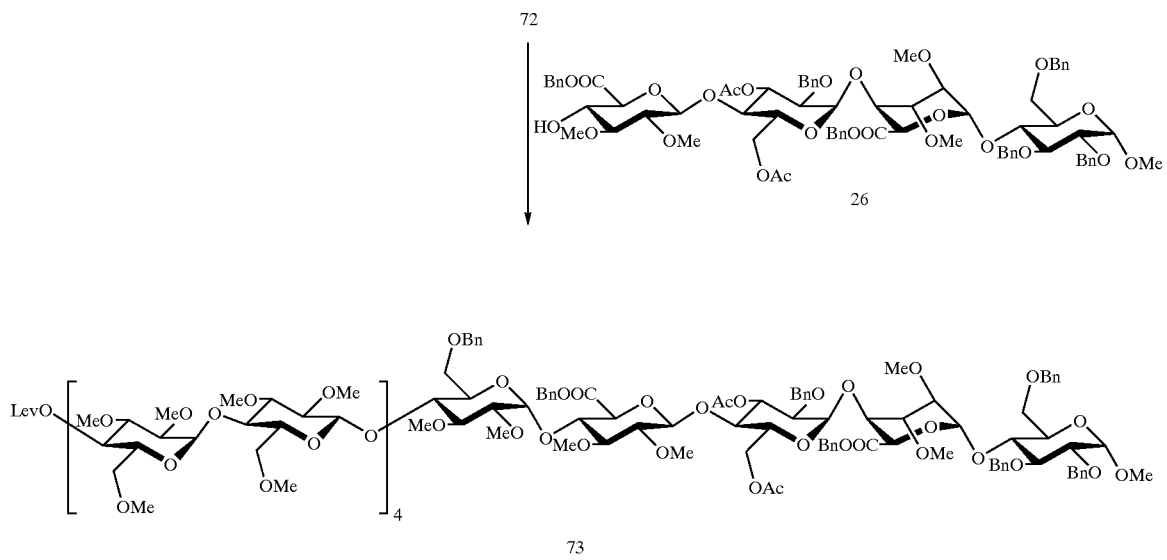

SCHEME 20
Synthesis of polysaccharide 73

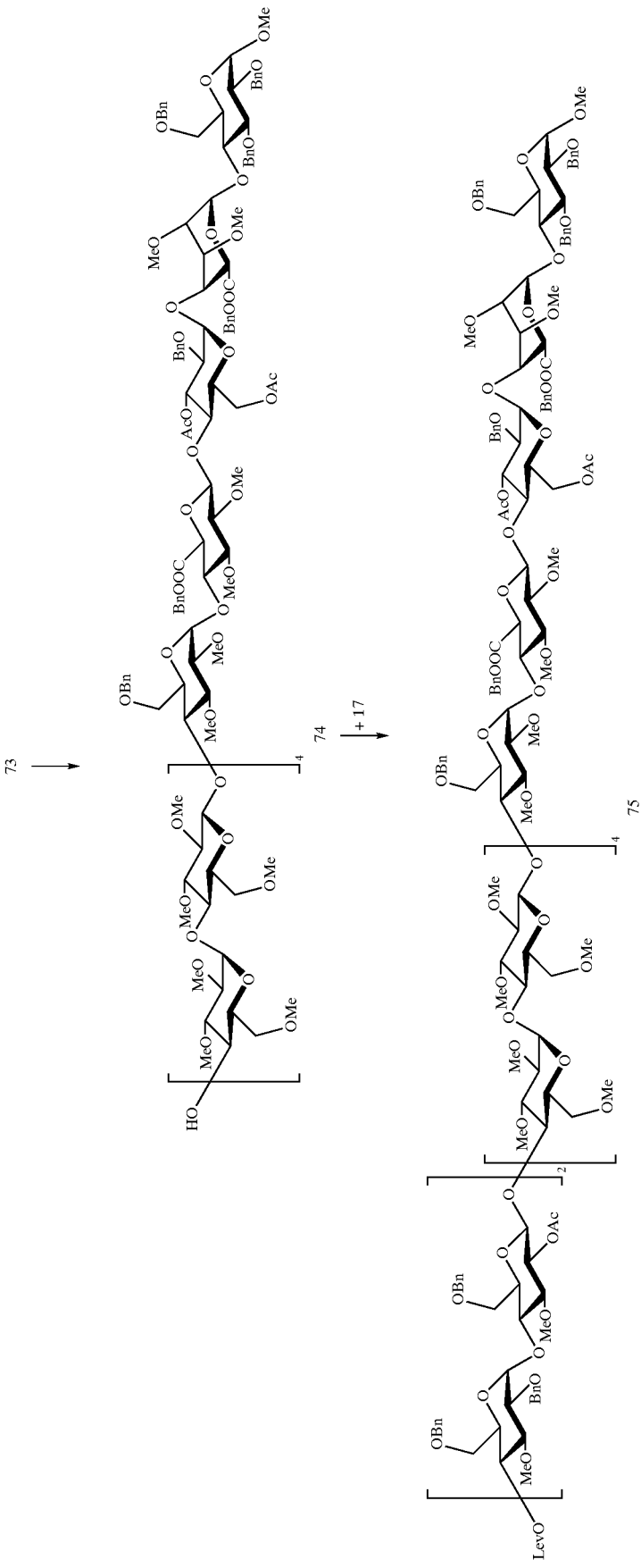

PREPARATION 68

Methyl [O-(2,3,6-Tri-O-methyl-α-D-glucopyranosyl)-(1-4)-O-(2,3,6-tri-O-methyl-β-D-glucopyranosyl)-(1-4)]₄-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyl-uronate)-(1-4)-2,3,6-tri-O-benzyl-α-D-glucopyranoside (74)

Compound 73 (130 mg, 38.2 μmol) is treated according to Method 2 and the crude product is purified on a column of silica in order to obtain 74 (118 mg, 93%). [α]$_D$+78 (c=0.48, dichloromethane); ESIMS, positive mode: monoisotopic mass=3301.49; chemical mass=3303.65; experimental mass=3302.40 a.m.u. ¹H NMR (CDCl₃) δ 7.33–7.25 (m, 35H, 7Ph), 5.64 (d, 3H, J=3.5 Hz, H-1 unit A, unit C and unit E), 5.57 (d, 1H, J=3.9 Hz, H-1 unit G), 5.52 (d, 1H, J=3.3 Hz, H-1 unit I), 5.29 (d, 1H, J=6.8 Hz, H-1 unit L), 5.17 (d, 1H, J=3.5 Hz, H-1 unit K), 4.56 (d, 1H, J=3.5 Hz, H-1 unit M), 4.31 (d, 3H, J=7.9 Hz, H-1 unit B, unit D and unit F), 4.27 (d, 1H, J=8.0 Hz, H-1 unit H), 4.08 (d, 1H, J=8.0 Hz, H-1 unit J), 1.97 (s, 3H, Ac), 1.81 (s, 3H, Ac).

PREPARATION 69

Methyl O-(2,6-Di-O-benzyl-4-O-levulinyl-3-O-methyl-α-D-glucopyranosyl)-(1-4)-O-(2-O-acetyl-6-O-benzyl-3-O-methyl-β-D-glucopyranosyl)-(1-4)-O-(2,6-di-O-benzyl-3-O-methyl-α-D-glucopyranosyl)-(1-4)-O-(2-O-acetyl-6-O-benzyl-3-O-methyl-β-D-glucopyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]₄-O-(6-O-benzyl-2,3-di-O-methyl-α-D-glucopyranosyl)-(1-4)-O-(benzyl 2,3-di-O-methyl-β-D-glucopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate-(1-4)-2,3,6-tri-O-benzyl-α-D-glucopyranoside (75)

The glycosyl acceptor 74 (112 mg, 33.9 μmol) and the imidate 17 (59.1 mg, 37.2 μmol) (see Preparation 16) are dissolved in toluene (2 ml). 4 Å molecular sieves (42 mg) are added and the mixture is left stirring at 25° C. for 1 hour. The mixture is cooled to −20° C. and a 1M solution of tert-butyldimethylsilyl triflate in toluene (0.20 mol/mol of imidate) is added. After stirring for 15 minutes, solid sodium hydrogen carbonate is then added and the mixture is filtered and concentrated. The residue is placed on a column of Toyopearl® HW-50 (1/1 dichloromethane/ethanol) and the fraction containing the acceptor and the 17-mer is returned to the reaction and treated as above. The product is purified successively on a column of Toyopearl® HW-50 and on a column of silica in order to obtain 75 (71 mg, 44%). [α]$_D$+80 (c 0.26, dichloromethane). ESIMS, positive mode: monoisotopic mass=4728.10; chemical mass=4731.26; experimental mass=4731.27±0.39 a.m.u. ¹H NMR (CDCl₃) δ of the main anomeric protons: 5.64; 5.57; 5.52; 5.48; 5.47; 5.29; 5.17; 4.56; 4.50; 4.29; 4.27; 4.08 ppm.

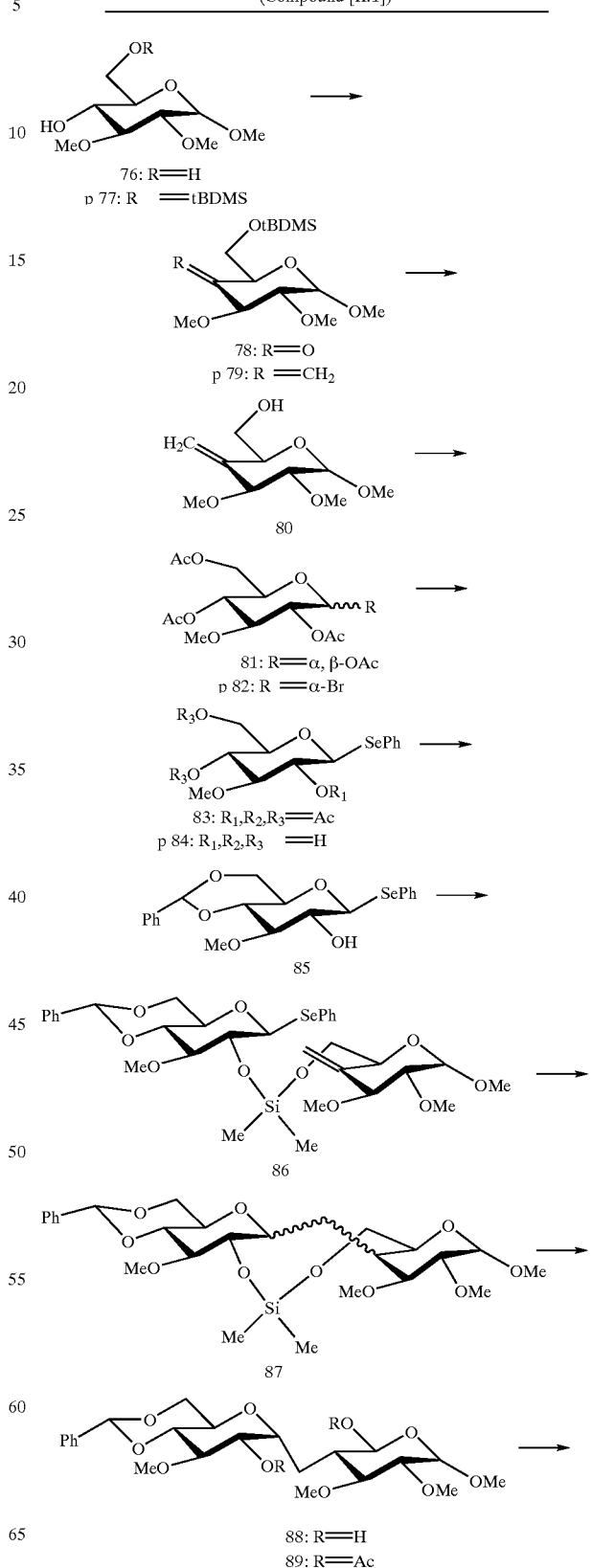

SCHEME 22
Preparation of a synthon which is useful for the synthesis of a pentasaccharide Pe possing a C - interglycoside linkage (Compound [II.1])

-continued

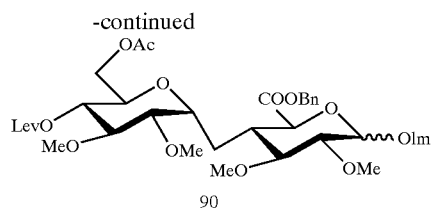

90

PREPARATION 70

Methyl 2,3-Di-O-Methyl-6-O-tert-butyldimethylsilyl-α-D-glucopyranoside (77)

Tert-butyldimethylsilyl chloride (14.0 g, 92.9 mmol), triethylamine (15 ml, 108 mmol) and 4-dimethylaminopyridine (260 mg, 2.13 mmol) are added, under argon, to a solution of 76 (D. Trimmell, W. M. Doane, C. R. Russel, C. E. Rist, Carbohydr. Res., (1969) 11, 497) (15.84 g, 71.3 mmol) in dichloromethane (300 ml). After stirring for 15 hours at room temperature, the solution is diluted with dichloromethane, washed with saturated aqueous sodium hydrogen carbonate solution, dried (magnesium sulphate), filtered and concentrated. The residue is purified by flash chromatography (1.3/1 cyclohexane/ethyl acetate) in order to obtain 77 (22.79 g, 95%) in the form of a colourless syrup. $[\alpha]_D$+87 (c=1.2, chloroform)

PREPARATION 71

Methyl 2,3-Di-O-Methyl-6-O-tert-butyldimethylsilyl-α-D-xylo-4-hexulopyranoside (78)

A solution of dimethyl sulphoxide (8.7 ml, 123 mmol) in dichloromethane (20 ml) is added, under argon and at −70° C., to a solution of oxalyl chloride (5.4 ml, 61.9 mmol) in dichloromethane (120 ml). After minutes, a solution of 77 (18.78 g, 55.8 mmol) in dichloromethane is added dropwise. After magnetic stirring for 15 minutes, triethylamine (37 ml, 265 mmol) is added and, after 15 minutes, the mixture is allowed to return to room temperature. Water (150 ml) is added and the aqueous phase is extracted with dichloromethane (150 ml). The organic phases are combined, washed with saturated aqueous sodium chloride solution, dried (magnesium sulphate) and concentrated. The residue is purified by flash chromatography (9/1 and then 4/1 cyclohexane/ethyl acetate) in order to obtain 78 (17.3 g, 93 i) in the form of a colourless oil. $[\alpha]_D$+98 (c 1.0, chloroform).

PREPARATION 72

Methyl 4-Deoxy-2,3-di-O-methyl-4-C-methylene-6-O-tert-butyldimethylsilyl-α-D-xylo-hexapyranoside (79)

A 1.6 M solution of n-butyllithium in n-hexane (75 ml) is added dropwise, under argon, to a suspension of methyltriphenylphosphonium bromide (43.3 g, 127 mmol) in tetrahydrofuran (250 ml). After 30 minutes at room temperature, the mixture is cooled to −70° C. A solution of 78 (13.97 g, 41.8 mmol) in tetrahydrofuran (60 ml) is then added. After 30 minutes at −70° C., the mixture is allowed to return to room temperature. After 1 hour, saturated aqueous ammonium chloride solution (300 ml) is added and the aqueous phase is extracted with ether. The organic phase is dried (magnesium sulphate), filtered and concentrated. The residue is purified by flash chromatography (7/1 and then 4/1 cyclohexane/ethyl acetate) in order to obtain 79 (8.30 g, 60%) in the form of a colourless oil. $[\alpha]_D$+151 (c=1.3, chloroform).

PREPARATION 73

Methyl 4-Deoxy-2,3-di-O-methyl-4-C-methylene-α-D-xylo-hexapyranoside (80)

Camphorsulphonic acid (pH 1) is added to a solution of 79 (8.50 g, 25.6 mmol) in a 5/1 dichloromethane/methanol mixture (250 ml). After complete disappearance of the starting material (TLC, 1/1 cyclohexane/ethyl acetate), the solution is neutralized by addition of triethylamine. After concentrating, the residue is purified by flash chromatography (1/1 and then 1/2 cyclohexane/ethyl acetate) to give 80 (5.32 g, 95%) in the form of a colourless syrup. $[\alpha]_D$+239 (c=1.0, chloroform).

PREPARATION 74

Phenyl 2,4,6-tri-O-Acetyl-3-O-methyl-1-seleno-β-D-glucopyranoside (83)

Method 1: Selenophenol (5.7 ml, 53.7 mmol) is added to a solution of 81 (E. L. Hirst, E. Percival, Methods Carbohydrate Chem., (1963) 2, 145) (1/1 mixture of anomers: 13.05 g, 36.0 mmol) in dichloromethane (120 ml) under argon. The reaction medium is cooled to 0° C. and 48% trifluoroborane diethyl etherate solution (8.8 ml, 71.9 mmol) is added dropwise. After 3 hours at room temperature, the reaction mixture is diluted with dichloromethane (100 ml), washed with saturated aqueous sodium hydrogen carbonate solution, dried (magnesium sulphate), filtered and concentrated. The crude compound 83 (8.17 g, 68%) from 81) is used directly in the deacetylation reaction.

Method 2: Sodium borohydride (510 mg, 14.6 mmol) is added, at 0° C. and under argon, to a suspension of diphenyl diselenide (2.27 g, 7.27 mmol) in ethanol. A further portion of trifluoroborane diethyl etherate is added if the reaction medium has not lost its original yellow colour within 15 minutes. This solution is transferred under argon to a solution of 82 (A. K. Sen, K. K. Sakar, N. Banerji, J. Carbohydr. Chem., (1988) 7, 645) (4.22 g, 11.0 mmol) in dichloromethane (25 ml). After refluxing for 3 hours, the mixture is left to cool to room temperature, the sodium bromide is filtered off and the filtrate is concentrated. The residue is dissolved in dichloromethane (100 ml) and washed with aqueous 1M sodium hydroxide solution (50 ml) and saturated aqueous ammonium chloride solution (50 ml). The aqueous phases are extracted with dichloromethane (20 ml) and the organic phases are dried (magnesium sulphate), filtered and concentrated. The residue is purified by flash chromatography (1.7/1 cyclohexane/ethyl acetate) and then crystallized from ethyl acetate in order to obtain 83 (4.35 g, 86%). m.p. 101–102° C. $[\alpha]_D$−20 (c=1.0, chloroform).

PREPARATION 75

Phenyl 3-O-Methyl-1-seleno-β-D-glucopyranoside (84)

The crude compound 83 obtained from 82 (32.3 g, 84.3 mmol) is dissolved in methanol (500 ml) and sodium (1.2 g)

is introduced slowly. After 1 hour, the solution is neutralized by addition of IR-120 (H⁺) resin, filtered and concentrated. The residue is purified by flash chromatography (1.5/1/1 cyclohexane/ethyl acetate/acetone) in order to obtain 84 in the form of a syrup (22.7 g, 81% from 82). $[\alpha]_D$–58 (c=1.0, methanol).

PREPARATION 76

Phenyl 4,6-O-Benzylidene-3-O-methyl-1-seleno-α-D-gluco-pyranoside (85)

P-Toluenesulphonic acid (45 mg) and benzaldehyde dimethyl acetal (5.4 ml, 36.0 mmol) are added, under argon, to a solution of triol 84 (7.65 g, 23.0 mmol) in acetonitrile (150 ml). After stirring for 2 hours at room temperature, potassium carbonate (1.5 g) is added. After 30 minutes, the solution is filtered and then concentrated. The residue is purified by flash chromatography (3.5/1 cyclohexane/ethyl acetate) in order to obtain 85 (8.55 g, 88%) in the form of white crystals. m.p. 123–124° C. (cyclohexane/ethyl acetate). $[\alpha]_D$–38 (c=1.0, chloroform).

PREPARATION 77

Phenyl 4,6-O-Benzylidene-3-O-methyl-2-O-(methyl-4-deoxy-6-O-dimethylsilyl-2,3-di-O-methyl-4-C-methylene-α-D-xylo-hexopyranoside)-1-seleno-β-D-glucopyranoside (86)

A 1.6 M solution of n-butyllithium (7.0 ml, 11.2 mmol) is added, under argon and at –70° C., to a solution of 85 (4.30 g, 10.2 mmol) in tetrahydrofuran (30 ml) placed in a Schlenck tube. After 10 minutes, dichlorodimethylsilane (5.0 ml, 41.2 mmol) is added and the reaction medium is warmed to room temperature. After 3 hours, the mixture is concentrated and a solution of 80 (2.10 g, 9.62 mmol) and imidazole (985 mg, 14.4 mmol) in tetrahydrofuran (20 ml) is added. After 30 minutes at room temperature, the solution is concentrated, water (50 ml) is added and the mixture is extracted with dichloromethane. The organic phase is dried (magnesium sulphate), filtered and concentrated. An analytical sample of 86 is purified by flash chromatography (25/1 toluene/acetone containing 0.5% triethylamine). A colourless syrup is obtained in a yield of 90%.

$^1$H NMR (400 MHz, C₆D₆) d 7.77–6.99 (m, 10H, aromatic), 5.51 (m, 1H, C:CH₂), 5.24 (m, 1H, C:CH₂), 5.16 (s, 1H, CHPh), 4.85 (d, 1H, J=3.7 Hz, H-1), 4.81 (d, 1H, J=9.8 Hz, H-1'), 4.45 (m, 1H, H-5), 4.38 (dd, 1H, J=10.8 Hz, 4.8 Hz, H-6a), 4.33 (dd, 1H, J=6.2 Hz, H-6b), 4.20 (m, 1H, J=9.2 Hz, H-3), 4.05 (dd, 1H, J=10.3 Hz, 4.9 Hz, H-6a'), 3.87 (dd, 1H, J=8.1 Hz, H-2'), 3.52, 3.38, 3.31 and 3.27 (s, 3H, OCH₃), 3.37 (t, 1H, J=10.3 Hz, H-6b'), 3.35 (t, 1H, H-4'), 3.32 (dd, 1H, H-2), 3.22 (dd, 1H, J=9.3 Hz, H-3'), 3.05 (ddd, 1H, J=9.3 Hz, H-5'), 0.38 and 0.37 (s, 3H, Si(CH₃)₂. MS (m/z): 714 (M+NH₄)⁺.

PREPARATION 78

Radical Cyclization Reaction (formation of 87) and Cleavage of the Tether (88)

A solution of tributyltin hydride (6.1 ml, 22.7 mmol) and 2,2'-azobisisobutyronitrile (200 mg, 1.22 mmol) in degassed toluene (14 ml) is added, over a period of 8 hours, to a solution of crude 86 in toluene (850 ml), obtained from 85 (10.2 mmol) and 80 (9.62 mmol).

After the radical cyclization, the mixture is concentrated and the residue is dissolved in tetrahydrofuran. An excess (20 equivalents) of hydrofluoric acid (at a concentration of 40% in water) is added. After complete desilylation (TLC, 4/1 toluene/acetone), the solution is neutralized by addition of solid sodium hydrogen carbonate, filtered and concentrated. The major compound 88 may be purified by crystallization. m.p. 105° C. $[\alpha]_D$+119 (c=1.1, chloroform). $^1$C NMR (62.896 MHz, CDCl₃) d 137.29 (quarternary aromatic C), 128.88–125.96 (aromatic C), 101.11 (CHPh), 97.64 (C-1), 83.52 (C-2), 82.76, 81.95, 80.84, 72.01, 71.92 and 64.31 (C-3, C-5, C-2', C-3', C-4', C-5'), 75.19 (C-1'), 69.41 (C-6'), 62.69 (C-6), 60.93, 60.70, 58.31 and 55.20 (OCH₃), 38.80 (C-4), 25.58 (methylene C).

Anal. Calculated for C₂₄H₃₆O₁₀.H₂O (502.558): C, 57.36; H, 7.62. Found: C, 57.31; H, 7.54.

PREPARATION 79

Methyl 6-O-Acetyl-4-C-(2-O-acetyl-4,6-O-benzylidene-3-O-methyl-α-D-glucopyranosylmethyl)-4-deoxy-2,3-di-O-methyl-α-D-glucopyranoside (89)

Compound 88 is acetylated quantitatively in a mixture of 1/1 acetic anhydride/pyridine, in the presence of a catalytic amount of 4-dimethylamino-pyridine. The product is obtained after concentration and chromatography. $[\alpha]_D$+87 (c=1.0, chloroform) $^1$H NMR (500 MHz, CDCl₃): see Table 1. $^{13}$C NMR (62.896 MHz, CDCl₃) d 170.81, 169.80 (C:O), 137.18 (quarternary aromatic C), 128.92–125.95 (aromatic C), 101.31 (CHPh), 97.51 (C-1), 83.22 (C-2), 81.94, 69.25 and 63.83 (C-5, C-4', C-5'), 81.81 (C-3), 78.78 (C-3'), 72.74 (C-2'), 71.96 (C-1'), 69.49 (C-6'), 64.17 (C-6), 60.64, 59.82, 58.30 and 55.19 (OCH₃), 39.00 (C-4), 26.47 (methylene C), 20.91, 20.76 (OCOCH₃). Mass spectrum (m/z): 586 (M+NH₄)⁺, 569 (M+H)⁺, 554 (M-OMe+NH₃)⁺, 537 (M-OMe)⁺.

Anal. Calculated for C₂₈H₄₀O₁₂.H₂O (586.632): C, 57.33; H, 7.22. Found: C, 57.28; H, 7.07.

The final part of the synthesis consists in converting 89 into imidate 90. To do this, the benzylidene is opened using sodium cyanoborohydride and hydrochloric acid. The hydroxyl group thus freed is temporarily protected in the form of the p-methoxy-benzyl ether. After deacetylation, the primary alcohol function is protected by selective introduction of tert-butyldimethylsilyl ether, and the compound thus obtained is methylated. Oxidation under the Jones conditions leads to the uronic acid, which is benzylated. The p-methoxybenzyl ether is subsequently cleaved off and a levulinic ester is introduced in this position. A system using a sulphuric acid/acetic acid/acetic anhydride mixture leads to acetolysis of the anomeric methyl group as well as of the benzyl ether in position 6', and gives a mixture of two anomeric acetates. Selective deacetylation of position 1 is carried out using hydrazine in dimethylformamide, and the mixture of anomers, dissolved in dichloro-methane, is converted into 90 with trichloroaceto-nitrile in the presence of 1,8-diazabicyclo[5.4.0]-undec-7-ene.

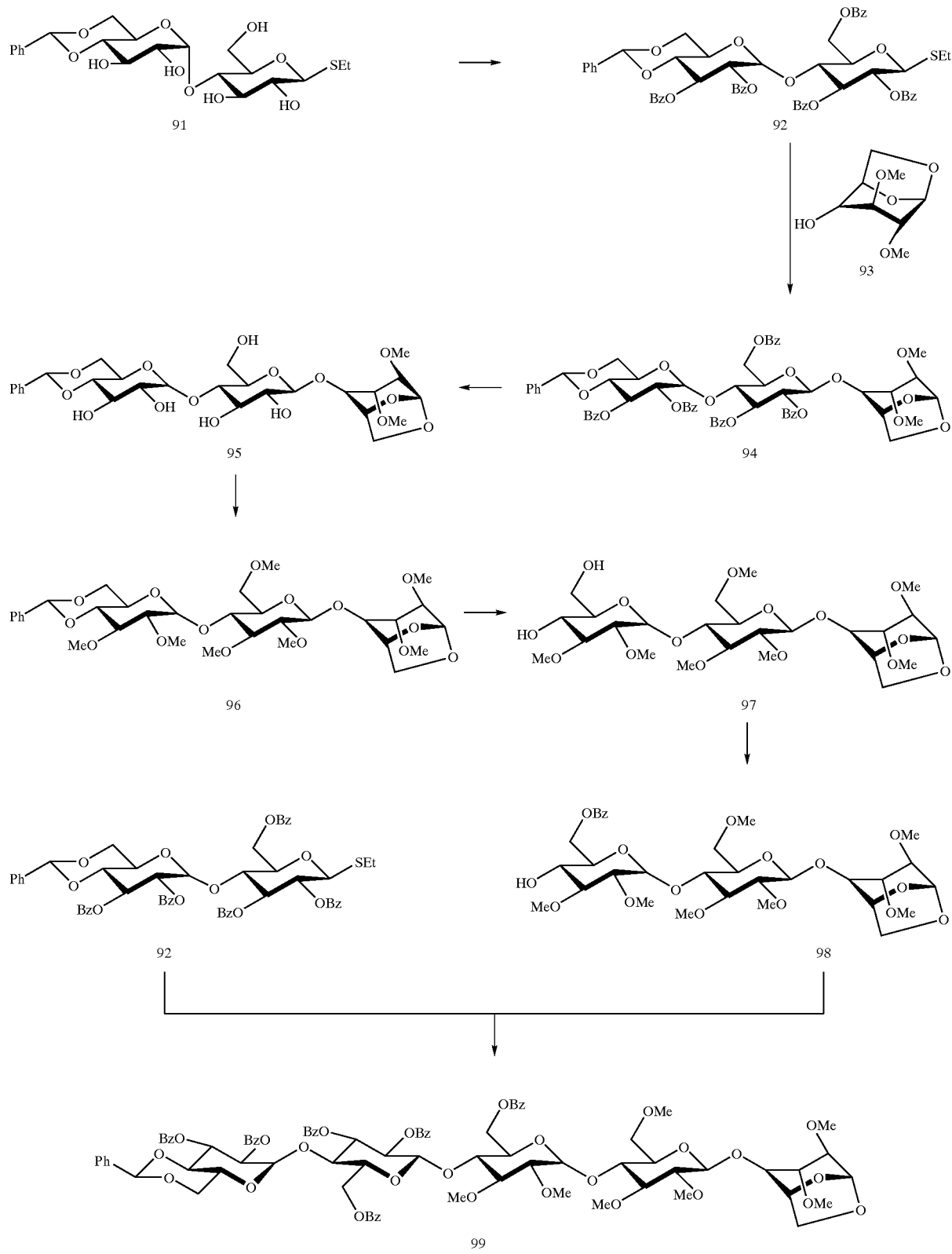
SCHEME 23
Synthesis of the pentasaccharide 99

PREPARATION 80

Ethyl O-(2,3-di-O-Benzoyl-4,6-O-benzylidene-α-D-gluco-pyranosyl)-(1→4)-2,3,6-tri-O-benzoyl-1-thio-β-D-glucopyranose (92)

Benzoyl chloride (24.5 ml, 211 mmol) is added dropwise over 20 minutes to a cooled (0° C.) solution of compound 91 (16.7 g, 35.2 mmol) (J. Westman and M. Nisson, *J. Carbohydr. Chem.*, 1995, 14(7), 949–960) in pyridine (202 ml). The reaction mixture is stirred for 20 hours at room temperature; TLC reveals an approximately 50% conversion. The mixture is diluted with water and dichloromethane. After extraction, the organic phase is washed with 10% sodium hydrogen carbonate solution, water, dried over magnesium sulphate and concentrated. The residue is again treated with benzoyl chloride according to the procedure described above. The crude product is purified by chromatography on a column of silica gel to give 22 g of compound 92.

TLC: Rf=0.80, silica gel, 9/1 v/v toluene/ethanol

PREPARATION 81

O-(2,3-Di-O-Benzoyl-4,6-O-benzylidene-α-D-glucopyranosyl)-(1→4)-O-(2,3,6-tri-O-benzoyl-α-D-glucopyranosyl)-(1→4)-1,6-anhydro-2,3-di-O-methyl-α-D-glucopyranose (94)

A mixture of thioglycoside 92 (1.05 g, 1.05 mmol), compound 93 (200 mg, 1.05 mmol) (Jeanioz et al., J. Org. Chem. 1961, 26, 3939–3944) and powdered 4 Å molecular sieves (1.1 g) in toluene (18 ml) is stirred under a nitrogen atmosphere for 15 minutes. The mixture is then cooled to −20° C. and a freshly prepared solution of N-iodosuccinimide (1.11 mmol) and trifluoromethanesulfonic acid (0.125 mmol) in 1/1 v/v dichloromethane/dioxane (6 ml) is introduced therein. After 10 minutes, the red reaction mixture is filtered, diluted with dichloromethane, extracted, washed successively with 10% sodium thiosulphate solution, 10% sodium hydrogen carbonate solution and water, dried over magnesium sulphate and then concentrated under vacuum. The residue is purified by chromatography, on a column of silica gel in order to obtain 1.25 g of compound 94.

TLC: Rf=0.55, silica gel, 4/6 v/v heptane/ethyl acetate

PREPARATION 82

O-(4,6-O-Benzylidene-α-D-glucopyranosyl)-(1→4)-O-(β-D-glucopyranosyl)-(1→4)-1,6-anhydro-2,3-di-O-methyl-β-D-glucopyranose (95)

Potassium tert-butoxide (about 50 mg) is added to a solution of compound 94 (1.24 g, 1.11 mmol) in 1/1 v/v methanol/dioxane (7 ml). The mixture is stirred for one hour and a further 50 mg of potassium tert-butoxide are then added; the mixture is then stirred for a further 60 minutes. The reaction mixture is neutralized with a Dowex® 50WX8 H⁺ resin, filtered and concentrated under vacuum. After chromatography on a column of silica gel, 665 mg of compound 95 are isolated in the form of an oil.

TLC: Rf=0.50, silica gel, 85/15 v/v dichloromethane/methanol

PREPARATION 83

O-(4,6-O-Benzylidene-2,3-di-O-methyl-α-D-glucopyranosyl)-(1→4)-O-(2,3,6-tri-O-methyl-α-D-glucopyranosyl)-(1→4)-1,6-anhydro-2,3-di-O-methyl-α-D-glucopyranose (96)

Sodium hydride (387 mg, 9.65 mmol) is added under a nitrogen atmosphere to a cooled (5° C.) solution of compound 95 (660 mg, 1.1 mmol) in dry tetrahydrofuran (8 ml). Methyl iodide (0.51 ml, 8.22 mmol) is added dropwise and the mixture is stirred for 20 hours at room temperature. The excess sodium hydride is destroyed with methanol and the mixture is poured into 50 ml of ice-cold water. After extraction with ethyl acetate (3 times 20 ml), the organic phase is washed with sodium chloride solution, dried over magnesium sulphate and concentrated to give 690 mg of pure compound 96.

TLC: Rf=0.25, silica gel, 95/5 v/v dichloromethane/methanol

PREPARATION 84

O-(2,3-Di-O-Methyl-α-D-glucopyranosyl)-(1→4)-O-2,3,6-tri-O-methyl-β-D-glucopyranosyl)-(1→4)-1,6-anhydro-2,3-di-O-methyl-β-D-glucopyranose (97)

The pure compound 96 (690 mg, 1.03 mmol) is dissolved in 80% acetic acid (7.3 ml) and stirred for hours at 40° C. The mixture is concentrated under vacuum and co-evaporated with toluene. Chromatography on a column of silica gel in 8/1/1 dichloromethane/ethyl acetate/methanol allows 569 mg of compound 97 to be obtained.

TLC: Rf=0.40, silica gel, 9/1 v/v dichloromethane/methanol

PREPARATION 85

O-(6-O-Benzoyl-2,3-di-O-methyl-α-D-glucopyranosyl)-(1→4)-O-(2,3,6-tri-O-methyl-β-D-glucopyranosyl)-(1→4)-1,6-anhydro-2,3-di-O-methyl-α-D-glucopyranose (98)

1-Benzoyloxy-1H-benzotriazole (227 mg, 1.05 mmol) and triethylamine (1.15 mmol) are added to a solution of compound 97 (560 mg, 0.96 mmol) in dichloromethane and the mixture is then stirred for 20 hours at room temperature. The reaction mixture is diluted with dichoromethane and washed with 10% sodium hydrogen carbonate solution and water. The organic phase is dried over magnesium sulphate, filtered and evaporated to dryness. The product is purified by chromatography on a column of silica gel in order to obtain 600 mg of compound 98.

TLC: Rf=0.50, silica gel, 9/1 v/v dichloromethane/methanol

PREPARATION 86

O-(2,3-Di-O-Benzoyl-4,6-O-benzylidene-α-D-glucopyranosyl)-(1→4)-O-(2,3,6-tri-O-benzoyl-β-D-glucopyranosyl)-(1→4)-O-(6-O-benzoyl-2,3-di-O-methyl-β-D-glucopyranosyl)-(1→4)-O-(2,3,6-tri-O-methyl-α-D-glucopyranosyl)-(1→4)-1,6-anhydro-2,3-di-O-methyl-α-D-glucopyranose (99)

Compound 98 is converted into compound 99 according to the procedure described for the preparation of compound 94. The coupling reaction is carried out at 5° C.

TLC: Rf=0.50, silica gel, 2/8 v/v heptane/ethyl acetate

SCHEME 24
Synthesis of the heptasaccharide 104
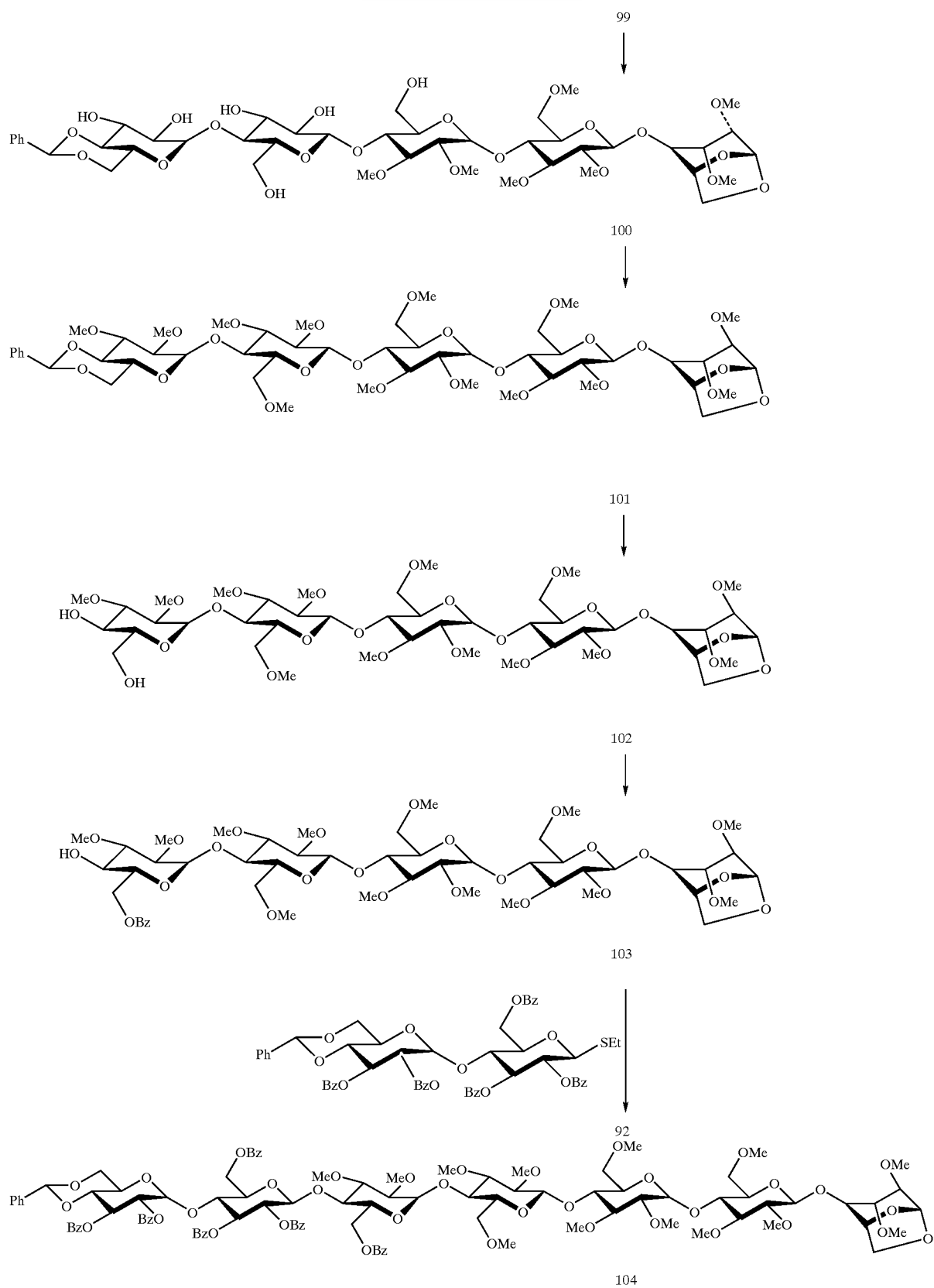

PREPARATION 87

O-(4,6-O-Benzylidene-α-D-glucopyranosyl)-(1→4)-
O-(⊖-D-glucopyranosyl)-(1→4)-O-(2,3-di-O-
methyl-α-D-glucopyranosyl)-(1→4)-O-(2,3,6-tri-O-
methyl-β-D-glucopyranosyl)-(1→4)-1,6-anhydro-2,
3-di-O-methyl-β-D-glucopyranose (100)

Compound 99 is converted into compound 100 according to the same procedure as that described for the preparation of compound 95.
TLC: Rf=0.35, silica gel, 9/1 v/v dichloromethane/methanol

PREPARATION 88

O-(4,6-O-Benzylidene-2,3-di-O-methyl-α-D-
glucopyranosyl)-(1→4)-O-(2,3,6-tri-O-methyl-β-D-
glucopyranosyl)-(1→4)-O-(2,3,6-tri-O-methyl-α-D-
glucopyranosyl)-(1→4)-O-(2,3,6-tri-O-methyl-β-D-
glucopyranosyl)-(1→4)-1,6-anhydro-2,3-di-O-
methyl-β-D-glucopyranose (101)

Compound 100 is converted into compound 101 according to the same procedure as that described for the preparation of compound 96.
TLC: Rf=0.50, silica gel, 9/1 v/v dicholoromethane/methanol

PREPARATION 89

O-(2,3-Di-O-Methyl-α-D-glucopyranosyl)-(1→4)-
O-(2,3,6-tri-O-methyl-β-D-glucopyranosyl)-(1→4)-
O-(2,3,6-tri-O-methyl-α-D-glucopyranosyl)-(1→4)-
O-(2,3,6-tri-O-methyl-β-D-glucopyranosyl)-(1→4)-
1,6-anhydro-2,3-di-O-methyl-β-D-glucopyranose (102)

Compound 101 is converted into compound 102 according to the same procedure as that described for the preparation of compound 97.
TLC: Rf=0.35, silica gel, 9/1 v/v dichloromethane/methanol

PREPARATION 90

O-(6-O-Benzoyl-2,3-di-O-methyl-α-D-
glucopyranosyl)-(1→4)-O-(2,3,6-tri-O-methyl-β-D-
glucopyranosyl)-(1→4)-O-(2,3,6-tri-O-methyl-α-D-
glucopyranosyl)-(1→4)-O-(2,3,6-tri-O-methyl-β-D-
glucopyranosyl)-(1→4)-1,6-anhydro-2,3-di-O-
methyl-α-D-glucopyranose (103)

Compound 102 is converted into compound 103 according to the same procedure as that described for the preparation of compound 98.

TLC: Rf=0.40, silica gel, 7.0/1.5/1.5 v/v/v toluene/ethyl acetate/ethanol

PREPARATION 91

O-(2,3-Di-O-Benzoyl-4,6-O-benzylidene-α-D-
glucopyranosyl)-(1→4)-O-(2,3,6-tri-O-benzoyl-β-D-
glucopyranosyl)-(1→4)-O-(6-O-benzoyl-2,3-di-O-
methyl-α-D-glucopyranosyl)-(1→4)-O-(2,3,6-tri-O-
methyl-O-D-glucopyranosyl)-(1→4)-O-(2,3,6-tri-O-
methyl-β-D-glucopyranosyl)-(1→4)-O-(2,3,6-tri-O-
methyl-α-D-glucopyranosyl)-(1→4)-1,6-anhydro-2,
3-di-O-methyl-β-D-glucopyranose (104)

The coupling reaction of compound 103 with the disaccharide 2 is carried out according to the procedure described for the preparation of compound 99.

TLC: Rf=0.40, silica gel, 7.0/1.5/1.5 v/v/v toluene/ethyl acetate/ethanol

SCHEME 25
Synthesis of the oligosaccharide 109

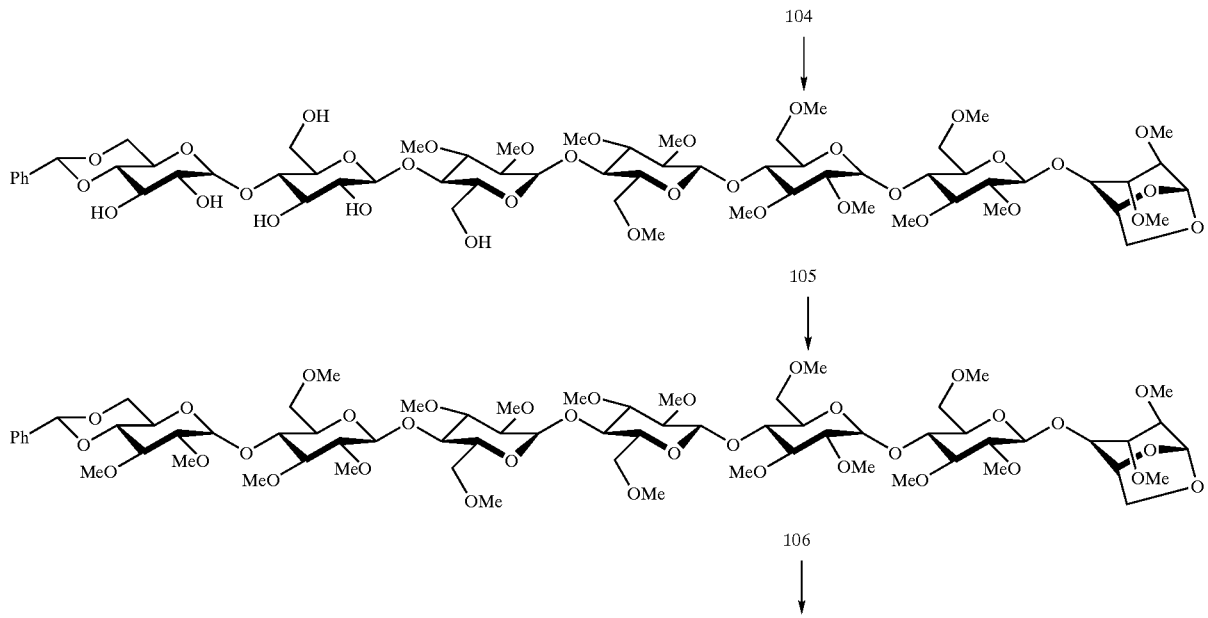

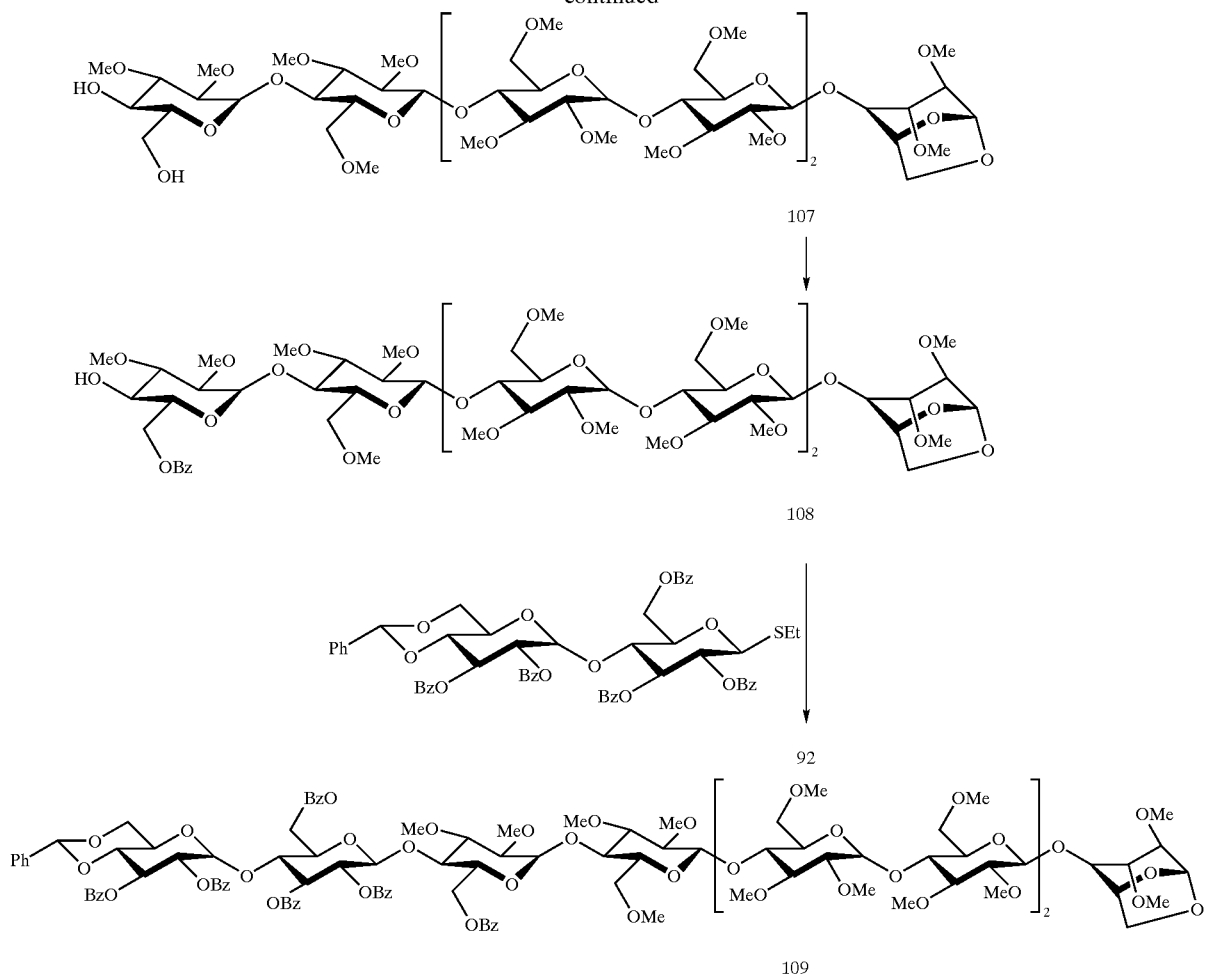

PREPARATION 92

O-(4,6-O-Benzylidene-α-D-glucopyranosyl)-(1→44)-O-β-D-glucopyranosyl)-(1→4)-O-(2,3-di-O-methyl-α-D-glucopyranosyl)-(→4)-O-(2,3,6-tri-O-methyl-β-D-glucopyranosyl)-(1→4)-O-(2,3,6-tri-O-methyl-α-D-glucopyranosyl)-(1→4)-O-(2,3,6-tri-O-methyl-β-D-glucopyranosyl)-(1→4)-1,6-anhydro-2,3-di-O-methyl-α-D-glucopyranose (105)

Compound 104 is converted into compound 105 according to the same procedure as that described for the preparation of compound 95.

TLC: Rf=0.60, silica gel, 9/1 v/v dichloromethane/methanol

PREPARATION 93

O-(4,6-O-Benzylidene-2,3-di-O-methyl-α-D-glucopyranosyl)-(1→44)-O-(2,3,6-tri-O-methyl-α-D-glucopyranosyl)-(1→4)-(O-(2,3,6-tri-O-methyl-α-D-glucopyranosyl)-(1→4)-O-(2,3,6-tri-O-methyl-α-D-glucopyranosyl)-(1→4)]₂-1,6-anhydro-2,3-di-O-methyl-O-D-glucopyranose (106)

Compound 105 is converted into compound 106 according to the same procedure as that described for the preparation of compound 96.

TLC: Rf=0.70, silica gel, 9/1 v/v dichloromethane/methanol

PREPARATION 94

O-(2,3-Di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₂-1,6-anhydro-2,3-di-O-methyl-β-D-glucopyranose (107)

A solution of compound 106 (5.05 g, 2.0 mmol) in 80% acetic acid (50 ml) is stirred for 20 hours at 40° C. The mixture is concentrated under vacuum and co-evaporated with toluene. The residue is dissolved in thyl acetate and extracted with water The aqueous hase is extracted with dichloromethane and the organic phase is dried over magnesium sulphate, filtered and evaporated to dryness to give 2.68 g of compound 107.

TLC: Rf=0.50, silica gel, 9/1 v/v dichloromethane/methanol

PREPARATION 95

O-(6-O-Benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₂-1,6-anhydro-2,3-di-O-methyl-β-D-glucopyranose (108)

Compound 107 is converted into compound 108 according to the same procedure as that described for the preparation of compound 98.

TLC: Rf=0.80, silica gel, 7.0/1.5/1.5 v/v/v toluene/ethyl acetate/ethanol

PREPARATION 96

O-(2,3-Di-O-Benzoyl-4,6-O-benzylidene-α-D-glucopyranosyl)-(1→4)-O-(2,3,6-tri-O-benzoyl-β-D-glucopyranosyl)-(1,4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_2$-1,6-anhydro-2,3-di-O-methyl-β-D-glucopyranose (109)

A mixture of the thioglycoside 92 (1.97 g, 2.0 mmol, 3.5 eq), heptasaccharide 108 (0.86 g, 0.57 mmol) and powdered 4 Å molecular sieves in toluene (22 ml) is stirred under a nitrogen atmosphere for 15 minutes. A freshly prepared solution containing N-iodosuccinimide (496 mg, 2.2 mmol) and trifluoromethanesulphonic acid (0.808 mmol) in 1/1 v/v dichloromethane/dioxane (12 ml) is then added dropwise at room temperature. After 10 minutes, the reaction mixture is filtered, diluted with dichloromethane, extracted, washed with 10% sodium thiosulphate solution and with 10% sodium hydrogen carbonate solution, dried over magnesium sulphate and concentrated under vacuum. The crude product is purified by chromatography on acolumn of silica gel, to give 1.09 g of compound 109.

TLC: Rf=0.80, silica gel, 6/2/2 v/v/v toluene/ethyl acetate/ethanol

SCHEME 26
Synthesis of the oligosaccharide 115

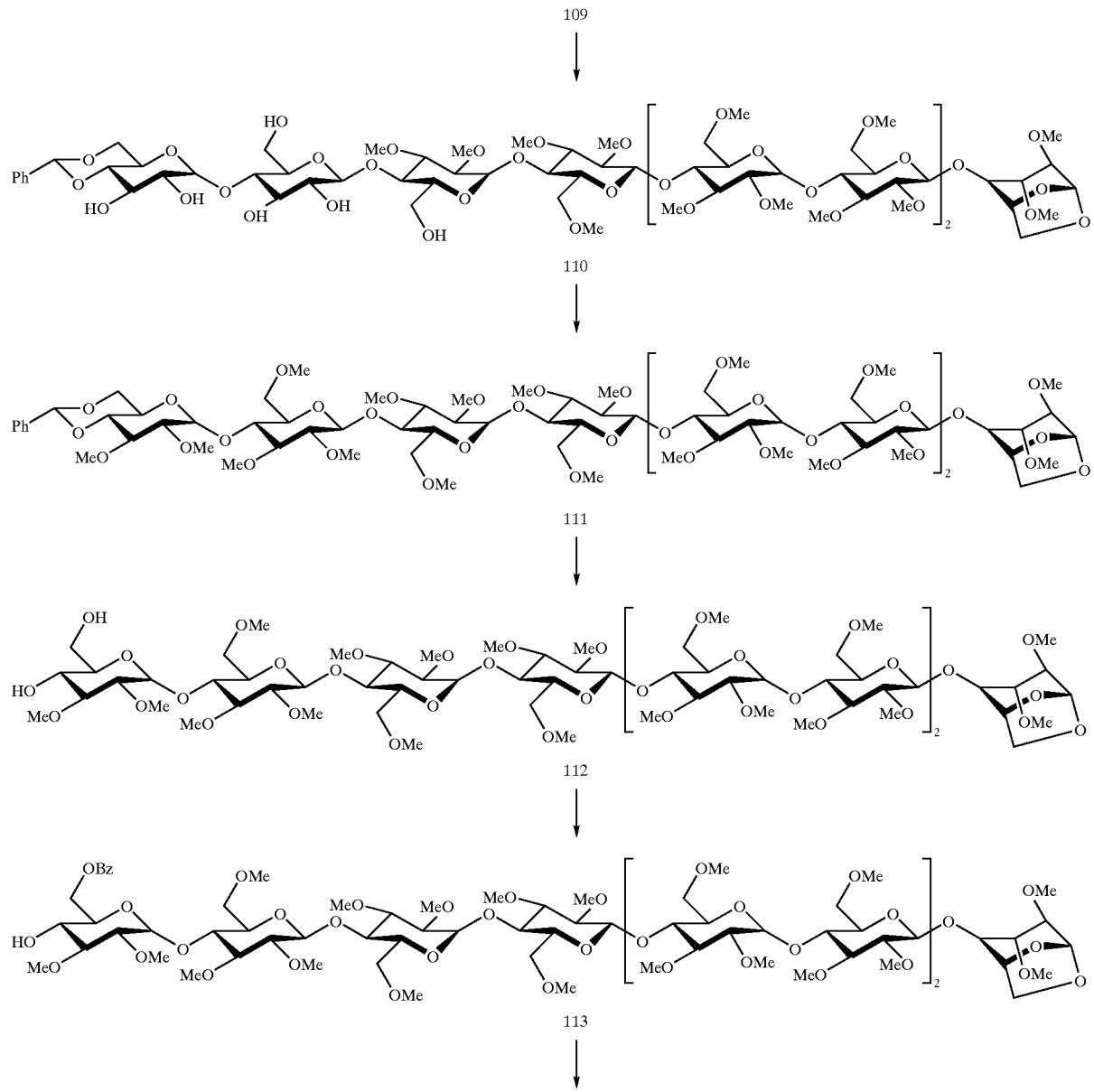

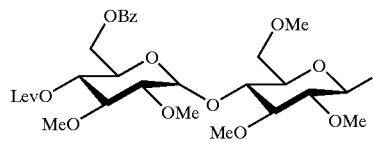 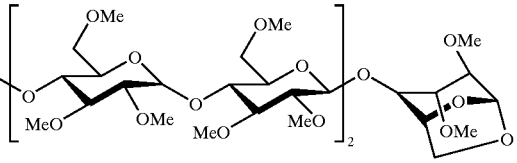

-continued

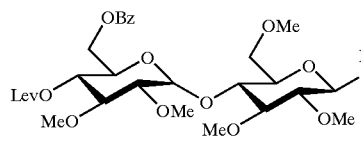 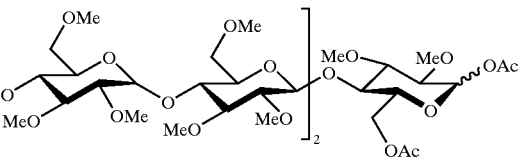

114 ↓

115

PREPARATION 97

O-(4,6-O-Benzylidene-α-D-glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-[(1→4)-O-(2,3,6-tri-O-methyl-α-D-glucopyranosyl)-(1→4)-O-(2,3,6-tri-O-methyl-β-D-glucopyranosyl)]₂-(1→4)-1,6-anhydro-2,3-di-O-methyl-β-D-glucopyranose (110)

Compound 109 is converted into compound 110 according to the same procedure as that described for the preparation of compound 95.
TLC: Rf=0.25, silica gel, 5.0/2.5/2.5 v/v/v toluene/ethyl acetate/ethanol

PREPARATION 98

O-(4,6-O-Benzylidene-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-anhydro-2,3-di-O-methyl-β-D-glucopyranose (111)

Compound 110 is converted into compound 111 according to the same procedure as that described for the preparation of compound 96.
TLC: Rf=0.50, silica gel, 6/2/2 v/v/v toluene/ethyl acetate/ethanol

PREPARATION 99

O-(2,3-Di-O-Methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranbsyl)-(1→4)-O-(2,3,6-tri-β-methyl-α-D-glucopyranosyl)-(1→4)]₃-1,6-anhydro-2,3-di-O-methyl-β-D-glucopyranose (112)

Compound 111 is converted into compound 112 according to the same procedure as that described for the preparation of compound 97.
TLC: Rf=0.20, silica gel, 6/2/2 v/v/v toluene/ethyl acetate/ethanol

PREPARATION 100

O-(6-O-Benzoyl-2,3-di-O-methyl-α-D-glucopyranosyl)-(1→4)-O-(2,3,6-tri-O-methyl-β-D-glucopyranosyl)-(1→4)-[-O-(2,3,6-tri-O-methyl-α-D-glucopyranosyl)-(1→4)-O-(2,3,6-tri-O-methyl-β-D-glucopyranosyl)-(1→4)]₃-1,6-anhydro-2,3-di-O-methyl-α-D-glucopyranose (113)

Compound 112 is converted into compound 113 according to the same procedure as that described for the preparation of compound 98.
TLC: Rf=0.20, silica gel, 6/2/2 v/v/v toluene/ethyl acetate/ethanol

PREPARATION 101

O-(6-O-Benzoyl-4-O-levulinyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-anhydro-2,3-di-O-methyl-α-D-glucopyranose (114)

1-(3-Dimethylaminopropyl)-3-ethylcarbodiimide hydrochloride (48 mg, 0.25 mmol), levulinic acid (29 mg, 0.25 mmol) and dimethylaminopyridine (4 mg, 0.033 mmol) are added to a solution of compound 113 (320 mg, 0.167 mmol) in dioxane (1 ml). The reaction mixture is stirred for 3 hours at room temperature under a nitrogen atmosphere. Dichloromethane and water are then added and, after extraction, the organic phase is washed with water, dried over magnesium sulphate, filtered and concentrated. The crude product is purified by chromatography on a column of silica gel to give 312 mg of compound 114.
TLC: Rf=0.50, silica gel, 6/2/2 v/v/v toluene/ethyl acetate/ethanol

PREPARATION 102

O-(6-Benzoyl-4-O-levuylinyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-1,6-di-O-acetyl-2,3-di-O-methyl-α,β-D-glucopyranose (115)

A solution of compound 114 (312 mg, 0.155 mmol) in a mixture of acetic anhydride (2.25 ml), acetic acid (50 ul) and trifluoroacetic acid (0.14 ml) is stirred for 4 hours at room temperature. After addition of toluene (10 ml), the mixture is concentrated and co-evaporated with toluene (3 times 10 ml). After chromatography on a column of silica gel, 324 mg of compound 115 are isolated.

TLC: Rf=0.65, silica gel, 6/2/2 v/v/v toluene/ethyl acetate/ethanol

SCHEME 27
Synthesis of the oligosaccharide 117

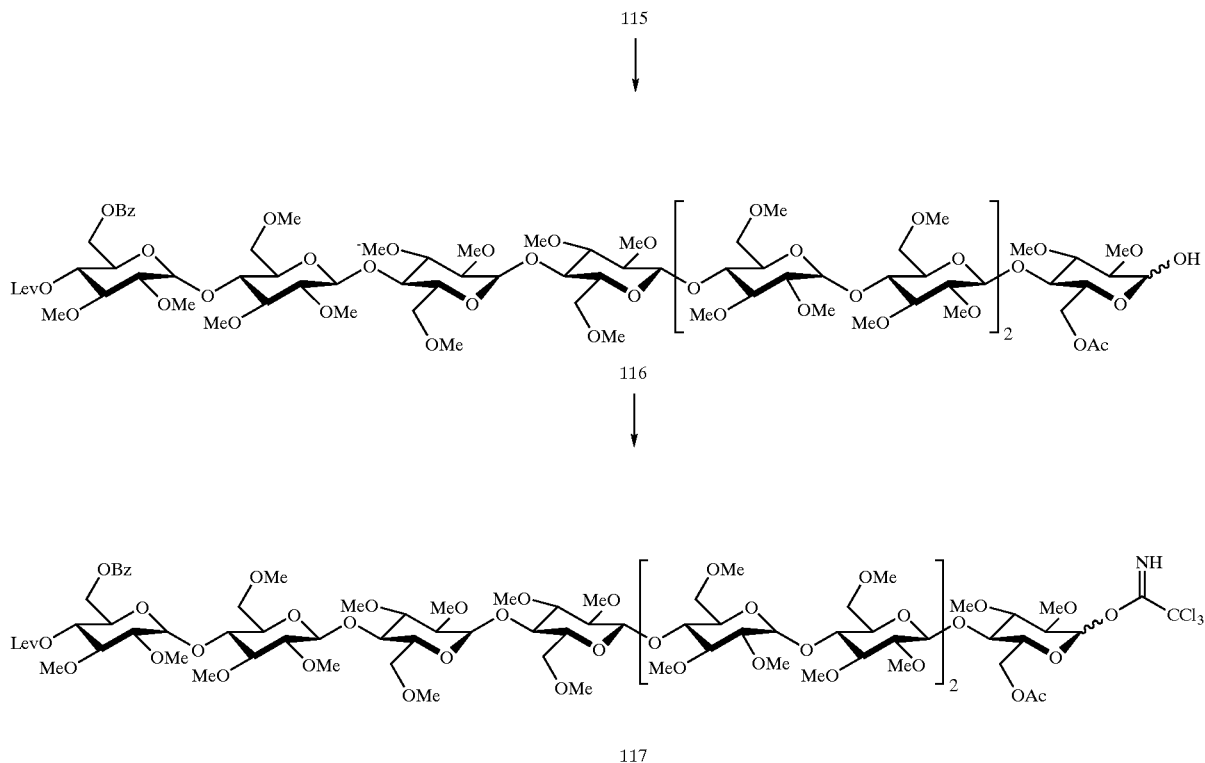

PREPARATION 103

O-(6-O-Benzoyl-4-O-levulinyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-6-O-acetyl-2,3-di-O-methyl-α,β-D-glucopyranose (116)

A solution of compound 115 (324 mg, 0.153 mmol) and morpholine (22.3 ul, 0.256 mmol) in toluene (2 ml) is stirred for 4 hours at 35° C. Morpholine (22.3 μl) is then added again and the reaction mixture is stirred for 20 hours at 35° C. The mixture is cooled rapidly with water. After extraction with dichloromethane, the organic phase is washed successively with 0.1N hydrochloric acid and water, dried and evaporated to dryness. After chromatography on a column of silica gel, 280 mg of comipound 116 are isolated.

TLC: Rf=0.45, silica gel, 6/2/2 v/v/v toluene/ethyl acetate/ethanol

PREPARATION 104

O-(6-O-Benzoyl-4-O-levulinyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-6-O-acetyl-2,3-di-O-methyl-α,β-D-glucopyranose trichloroacetimidate (117)

Trichloroacetonitrile (39 μl, 0.39 mmol) and caesium carbonate (4.7 mg) are added to a solution of compound 116 (138 mg, 0.066 mmol) in dichloromethane (1.5 ml). After stirring for 2 hours, the mixture is filtered and concentrated and the residue is chromatographed on a column of silica gel to give 152 mg of the imidate 117.

TLC: Rf=0.35, silica gel, 8/1/1 v/v/v toluene/ethyl acetate/ethanol

SCHEME 28

Synthesis of the disaccharide 128

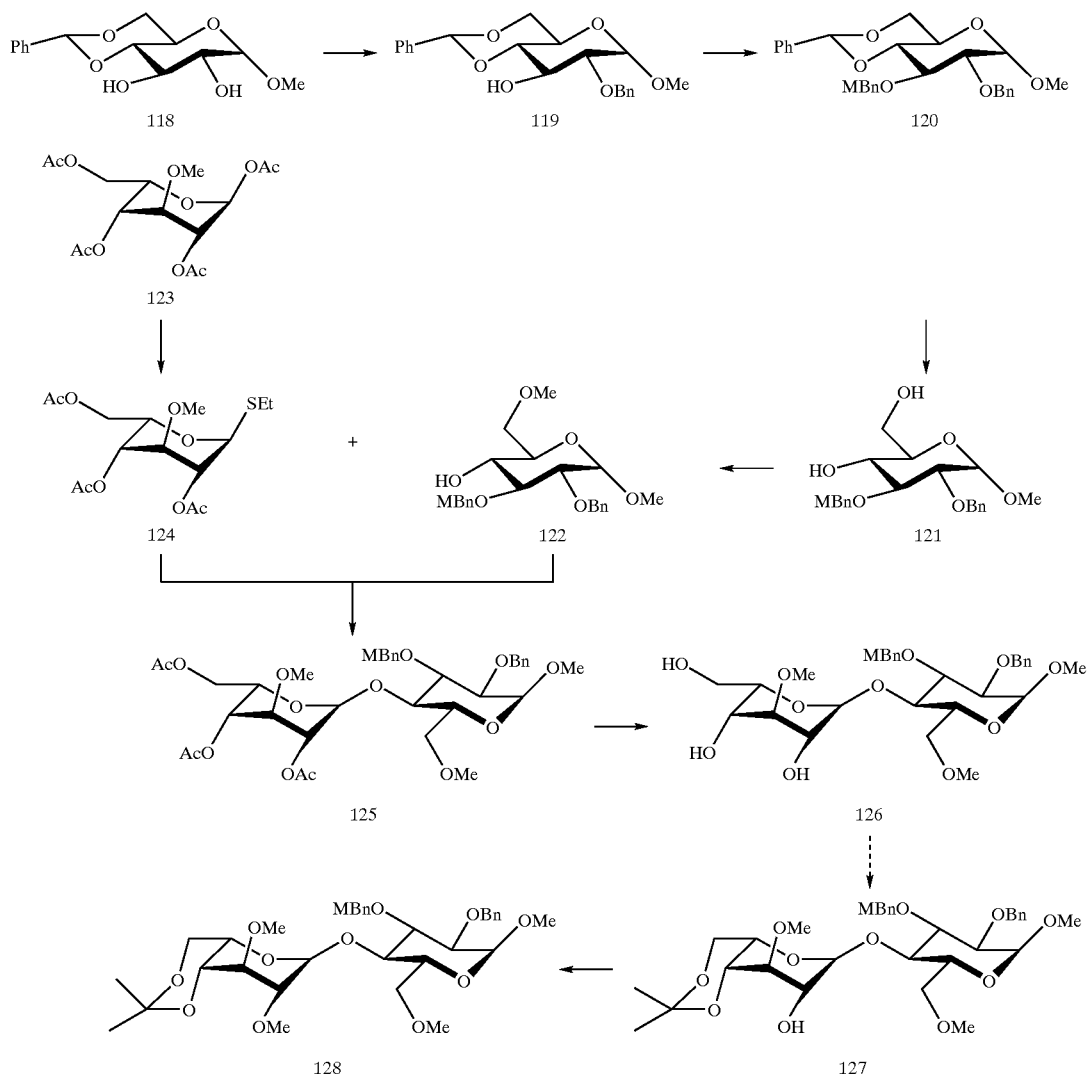

PREPARATION 105

Methyl 2-O-Benzyl-4,6-O-benzylidene-α-D-glucopyranoside (119)

The compound 118 (60 g) (commercially available) is dissolved in dimethylformamide (858 ml) with benzyl bromide (50.5 ml). After cooling to 10° C., aqueous 20% sodium hydroxide solution is added dropwise. After stirring for 1 hour, the temperature is raised to 20° C. and the mixture is stirred for a further 20 hours. The solution is then poured into a mixture of ice-water and toluene and extracted. The organic phase is concentrated and the crude product is purified by crystallization to give 30.0 g of compound 119.
TLC: Rf=0.60, silica gel, 7/3 v/v toluene/ethyl acetate

PREPARATION 106

Methyl 2-O-Benzyl-4,6-O-benzylidene-3-O-p-methoxy-benzyl-α-D-glucopyranoside (120)

Compound 119 (26.4 g) is dissolved in dimethylformamide (211 ml) and cooled to 5° C. Sodium hydride (2.5 g) is added under a nitrogen atmosphere. 4-methoxybenzyle chloride (13.3 g) is then added dropwise and the mixture is stirred for 1 hour at room temperature. The mixture is diluted with ethyl acetate, washed twice with water and concentrated to give 40.7 g of pure compound 120.

TLC: Rf=0.80, silica gel, 7/3 v/v toluene/ethyl acetate

PREPARATION 107

Methyl 2-O-Benzyl-3-O-p-methoxybenzyl-α-D-glucopyranoside (121)

Compound 120 (34.9 g) is dissolved in aqueous 60% acetic acid and stirred for 4 hours at 60° C. The mixture is diluted with toluene and concentrated. Purification by chromatography on a column of silica gel allows 26.4 g of compound 121 to be obtained.

TLC: Rf=0.07, silica gel, 7/3 v/v toluene/ethyl acetate

PREPARATION 108

Methyl 2-O-Benzyl-3-O-p-methoxybenzyl-6-O-methyl-α-D-glucopyranoside (122)

Compound 121 (26.4 g) is dissolved in dichloromethane (263 ml) under a nitrogen atmosphere. Trimethyloxonium tetrafluoroborate (11.6 g) and 2,6-di-tert-butyl-4-methylpyridine (17.4 g) are added at room temperature. After 4 hours, the mixture is poured onto ice-water and extracted with dichloromethane. The organic phase is washed with sodium hydrogen carbonate and concentrated. Purification of the crude product by chromatography on a column of silica gel allows 18.5 g of compound 122 to be obtained.

TLC: Rf=0.25, silica gel, 7/3 v/v toluene/ethyl acetate

PREPARATION 109

Ethyl 2,4,6-Tri-O-acetyl-3-O-methyl-1-thio-α-L-idopyranose (124)

Compound 123 (1,2,4,6-tetra-o-acetyl-3-O-methyl-α-L-idopyranose) (Jaurand et al. Bio. Med. Chem. Lett. 1992, 2, 897–900) (48.4 g) is dissolved in toluene (175 ml). Ethanethiol (20 ml) and boron trifluoride etherate in toluene (134 ml) are added, under a nitrogen atmosphere. After stirring for 1 hour, aqueous sodium hydrogen carbonate (400 ml) is added and the mixture is stirred for a further one hour. The mixture is then poured into ethyl acetate. The organic phase is washed twice with water and concentrated. Purification by chromatography on a column of silica gel allows 29.6 g of compound 124 to be obtained.

TLC: Rf=0.45, silica gel, 6/4 v/v toluene/ethyl acetate

PREPARATION 110

Methyl O-(2,4,6-Tri-O-acetyl-3-O-methyl-α-L-idopyranosyl-(1→4)-2-O-benzyl-3-O-p-methoxybenzyl-6-O-methyl-α-D-glucopyranoside (125)

Compound 122 (17.5 g) and compound 124 (28.2 g) are dissolved in toluene (525 ml) under a nitrogen atmosphere. After adding 4A molecular sieves, the reaction is cooled to −20° C. A freshly prepared solution of 0.1M N-iodosuccinimide (17.4 g) and trifluoromethanesulphonic acid (1.38 ml) in 1/1 v/v dioxane/dichloromethane is added dropwise under a continuous flow of nitrogen. After 10 minutes, the red reaction mixture is filtered and washed successively with aqueous sodium thiosulphate and aqueous sodium hydrogen carbonate. The organic phase is concentrated under vacuum and 30.0 g of compound 125 are isolated.

TLC: Rf=0.45, silica gel, 8/2 v/v dichloromethane/ethyl acetate

PREPARATION 111

Methyl O-(3-O-Methyl-α-L-idopyranosyl)-(1→4)-2-O-benzyl-3-O-p-methoxybenzyl-6-O-methyl-α-D-glucopyranoside (126)

Compound 125 (30.0 g) is dissolved in 460 ml of 1/1 v/v methanol/dioxane and potassium tert-butoxide is added. After 15 minutes, the mixture is neutralized with a Dowex 50WX8H⁺ resin and concentrated under vacuum. Purification is carried out by chromatography on a column of silica gel to give 17.4 g of compound 126.

TLC: Rf=0.25, silica gel, 95/5 v/v dichloromethane/methanol

PREPARATION 112

Methyl O-(4,6-O-Isopropylidene-3-O-methyl-α-L-idopyranosyl)-(1→4)-2-O-benzyl-3-O-p-methoxybenzyl-6-O-methyl-α-D-glucopyranoside (127)

Compound 126 (17.4 g) is dissolved in dimethylformamide (77 ml) under a nitrogen atmosphere. 2,2-Dimethoxypropane (26 ml) and p-toluenesulphonic acid are added and the mixture is then stirred for 30 minutes. Dilution of the mixture with aqueous sodium hydrogen carbonate followed by its extraction with ethyl acetate allows 19.7 g of compound 127 to be obtained after evaporation of the solvent.

TLC: Rf=0.45, silica gel, 95/5 v/v dichloromethane/methanol

PREPARATION 113

Methyl O-(4,6-O-Isopropylidene-2,3-di-O-methyl-α-L-idopyranosyl)-(1→4)-2-O-benzyl-3-O-methoxybenzyl-6-O-methyl-α-D-glucopyranoside (128)

Compound 127 (18.5 g) is dissolved in dimethylformamide (24.4 ml) and cooled to 0° C. Sodium hydride (1.47 g; 60% dispersion in oil) and iodomethane (2.36 ml) are added under a nitrogen atmosphere. After one hour, the excess sodium hydride is destroyed with methanol and the mixture is extracted with dichloromethane and concentrated to give 20.0 g of compound 128.

TLC: Rf=0.85, silica gel, 95/5 v/v dichloromethane/methanol

SCHEME 29

Synthesis of the disaccharide 138

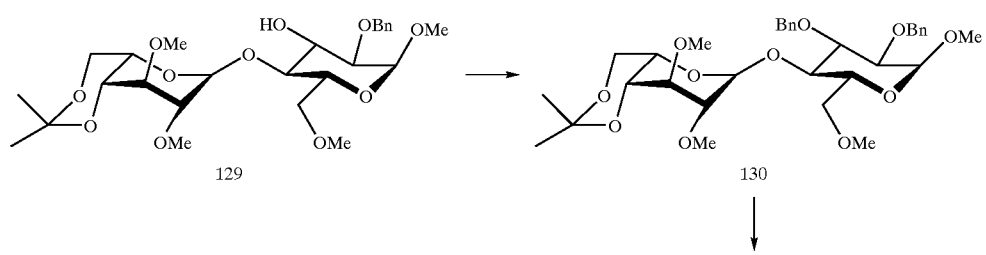

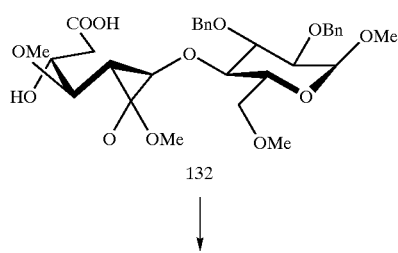

132

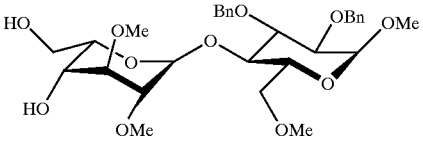

131

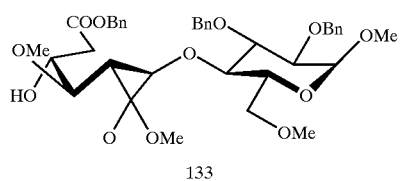

133

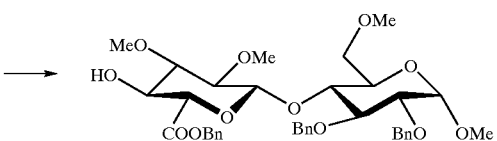

134

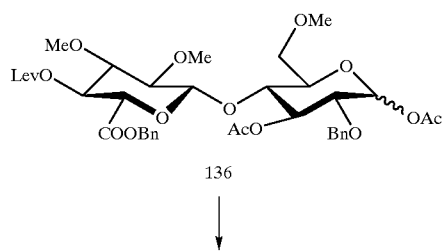

136

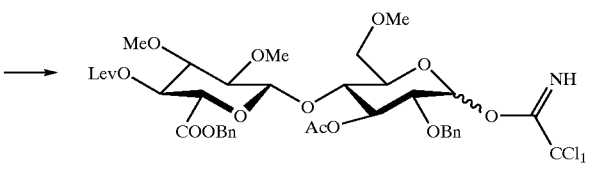

135

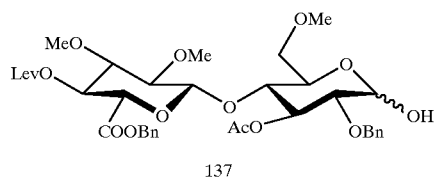

137

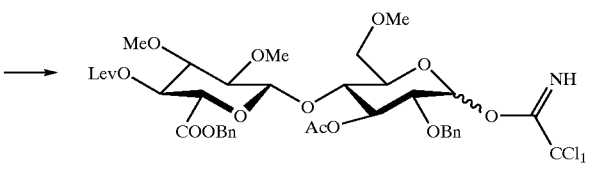

138

PREPARATION 114

Methyl O-(4,6-O-Isopropylidene-2,3-di-O-methyl-α-L-idopyranosyl)-(1→4)-2-O-benzyl-6-O-methyl-α-D-glucopyranoside (129)

Compound 128 (18.4 g) is dissolved in dichloromethane (838 ml) and water (168 ml). 2,3-Dichloro-5,6-dicyano-1, 4-benzoquinone (7.1 g) is added and the mixture is stirred for 18 hours at 4° C. The mixture is poured into aqueous sodium hydrogen carbonate and extracted with dichloromethane. Concentration of the organic phase gives 12.7 g of compound 129.

TLC: Rf=0.40, silica gel, 95/5 v/v dichloromethane/methanol

PREPARATION 115

Methyl O-(4,6-O-Isopropylidene-2,3-di-O-methyl-α-L-idopyranosyl)-(1→4)-2,3-di-O-benzyl-6-O-methyl-α-D-glucopyranoside (130)

Compound 129 (10.5 g) is dissolved in dry dimethylformamide (178 ml) and then cooled to 0° C. under a nitrogen atmosphere. Sodium hydride (1.91 g; 60% dispersion in oil) is added, followed by dropwise addition of benzyl bromide (3.3 ml). After 30 minutes, the reaction is complete and the excess sodium hydride is destroyed with methanol. Water is added and the mixture is extracted twice with ethyl acetate. Evaporation of the solvent allows 13.6 g of compound 130 to be obtained.

TLC: Rf=0.50, silica gel, 1/1 v/v toluene/ethyl acetate

PREPARATION 116

Methyl O-(2,3-Di-O-methyl-α-L-idopyranosyl)-(1→4)-2,3-35 di-O-benzyl-6-O-methyl-α-D-glucopyranoside (131)

Compound 130 is dissolved in 77/33 (v/v) acetic acid/water and stirred overnight. The mixture is co-evaporated twice with toluene and purified by chromatography on a column of silica gel to obtain 11.5 g of compound 131.

TLC: Rf=0.09, silica gel, 1/1 v/v toluene/ethyl acetate

Rf=0.68, silica gel, 9/1 v/v dichloromethane/methanol

PREPARATION 117

Methyl O-(2,3-Di-O-methyl-α-L-idopyranosyluronic acid)-(1→4)-2,3-di-O-benzyl-6-O-methyl-α-D-glucopyranoside (132)

2,2,6,6-Tetramethyl-1-piperidinyloxy [lacuna] (33 mg), sodium hydrogen carbonate solution (40 ml), potassium bromide (218 mg) and tetrabutylammonium chloride (289 mg) are added to a solution of compound 131 (11.6 g) in dichloromethane (60 ml). The mixture is cooled to 0° C. and a mixture of saturated sodium chloride solution (44 ml), saturated sodium hydrogen carbonate solution (21.8 ml) and sodium hypochlorite (1.3 M, 50 ml) is added over 15 minutes. After stirring for 1 hour, the mixture is diluted with water and extracted (3 times) with dichloromethane. The organic phase is washed with aqueous sodium chloride solution, dried over magnesium sulphate, filtered and evaporated to dryness to give 13.4 g of the crude compound 132.
TLC: Rf=0.14, silica gel, 9/1 v/v dichloromethane/methanol

PREPARATION 118

Methyl O-(Benzyl 2,3-Di-O-methyl-α-L-idopyranosyluronate)-(1→4)-2,3-di-O-benzyl-6-O-methyl-α-D-glucopyranoside (133)

Compound 132 is dissolved in dimethylformamide (110 ml) under a nitrogen atmosphere. Potassium hydrogen carbonate (6.7 g) and benzyl bromide (10.7 ml) are added and the mixture is stirred for 90 minutes. Ethyl acetate and water are added and, after extraction, the organic phase is concentrated. Purification by chromatography on a column of silica gel allows 9.9 g of compound 133 to be obtained.
TLC: Rf=0.43, silica gel, 4/6 v/v toluene/ethyl acetate

PREPARATION 119

Methyl O-(Benzyl 2,3-Di-O-methyl-β-D-glucopyranosyluronate)-(1→4)-2,3-di-O-benzyl-6-O-methyl-α-D-glucopyranoside (134)

Compound 133 (9.9 g) is dissolved in 300 ml of methanol and heated to reflux under a nitrogen atmosphere. A 1M solution of sodium methoxide in methanol (65.2 ml) is added dropwise and the mixture is stirred and heated at reflux for 3 hours. The mixture is then cooled to room temperature, 1N sodium hydroxide (22.2 ml) is added and the reaction mixture is stirred for a further 90 minutes. After neutralization with Dowex 50WX8H$^+$ resin and filtration, the mixture is concentrated. The pure product is dissolved in dimethylformamide (192 ml) and molecular sieves are added under a nitrogen atmosphere. Potassium hydrogen carbonate (3.2 g) and benzyl bromide (4.8 ml) are added and the mixture is stirred for 5 hours. After addition of ethyl acetate and water, extraction and separation of the two phases, the organic phase is concentrated. The crude product is purified by chromatography on a column of silica gel to give 6.19 g of compound 134 and 1.88 g of the starting compound 133.
TLC: Rf=0.55, silica gel, 4/6 v/v toluene/ethyl acetate

PREPARATION 120

Methyl O-(Benzyl 4-O-Levulinyl-2,3-di-O-methyl-β-D-glucopyranosyluronate)-(1→4)-2,3-di-O-benzyl-6-O-methyl-α-D-glucopyranoside (135)

Compound 134 (6.2 g) is dissolved in 40 ml of dioxane. Levulinic acid (2.1 g), dicyclohexylcarbodiimide (3.75 g) and 4-dimethylaminopyridine (0.2 g) are added and the mixture is stirred for 2 hours under a nitrogen atmosphere. Diethyl ether (95 ml) is added and the precipitate is filtered off. The filtrate is washed with aqueous potassium hydrogen sulphate, dried over magnesium sulphate, filtered and concentrated. Crystallization from ether/heptane allows 6.2 g of compound 135 to be obtained.

TLC: Rf=0.26, silica gel, 95/5 v/v dichloromethane/acetone

PREPARATION 121

O-(Benzyl 4-O-Levulinyl-2,3-di-O-methyl-β-D-glucopyranosyluronate)-(1→4)-1,3-di-O-acetyl-2-O-benzyl-6-O-methyl-α,β-D-glucopyranose (136)

Compound 135 (6.1 g) is dissolved in acetic anhydride (256 ml) under a nitrogen atmosphere and cooled to −20° C. A mixture of sulphuric acid (4.9 ml) in acetic anhydride (49 ml) is added dropwise over 30 minutes. After 60 minutes, sodium acetate is added until a mixture having a neutral pH is obtained. Ethyl acetate and water are then added and the organic phase is concentrated. Purification by chromatography on a column of silica gel allows 4.2 g of compound 136 to be obtained.

TLC: Rf=0.24, silica gel, 8/2 v/v dichloromethane/ethyl acetate

PREPARATION 122

O-(Benzyl 4-O-Levulinyl-2,3-di-O-methyl-β-D-glucopyranosyluronate)-(1→4)-3-O-acetyl-2-O-benzyl-6-O-methyl-α,β-D-glucopyranose (137)

Compound 136 (4.2 g) is dissolved in tetrahydrofuran (42 ml) and piperidine (4.1 ml) is added. The mixture is stirred overnight at room temperature. Ethyl acetate is added and the mixture is washed with 0.5 N hydrochloric acid. The organic phase is concentrated and the residue is purified by chromatography on a column of silica gel to give 3.2 g of compound 137.

TLC: Rf=0.33, silica gel, 1/1 v/v dichloromethane/ethyl acetate

PREPARATION 123

O-(Benzyl 4-O-Levulinyl-2,3-di-O-methyl-α-D-glucopyranosyluronate)-(1→4)-3-O-acetyl-2-O-benzyl-6-O-methyl-α-D-glucopyranose Trichloroacetimidate (138)

Compound 137 (1.59 g) is dissolved in dry dichloromethane under a nitrogen atmosphere. Trichloroacetonitrile (1.1 ml) and caesium carbonate (72 mg) are added and the mixture is stirred for 1 hour. The caesium carbonate is filtered off and the filtrate is concentrated. Purification by chromatography on a column of silica gel allows 1.57 g of compound 138 to be obtained.

TLC: Rf=0.60, silica gel, 3/7 v/v toluene/ethyl acetate

SCHEME 30

Synthesis of the tetrasaccharide 140

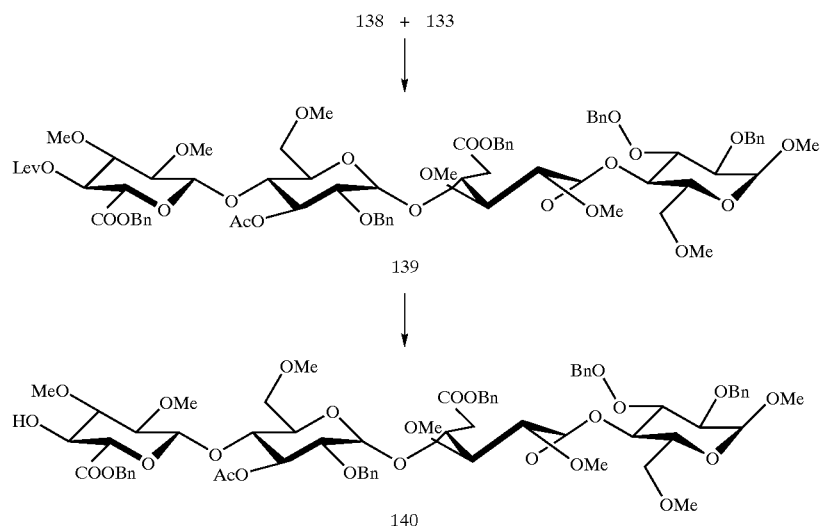

PREPARATION 124

Methyl O-(Benzyl 4-O-Levulinyl-2,3-di-O-methyl-
β-D-glucopyranosyluronate)-(1→4)-O-(3-O-acetyl-
2-O-benzyl-6-O-methyl-α-D-glucopyranosyl)-
(1→4)-O-(benzyl 2,3-di-O-methyl-α-L-
idopyranosyluronate)-(1→4)-2,3-di-O-benzyl-6-O-
methyl-α-D-glucopyranoside (139)

A mixture of compound 133 (300 mg) and compound 138 (455.6 mg) is co-evaporated with toluene and dissolved in dichloromethane (6 ml) under a nitrogen atmosphere. After addition of 4 Å molecular sieves, the mixture is cooled to −20° C. After stirring for 20 minutes, trimethylsilyl trifluoromethanesulphonate (15molt % relative to compound 138) is added. After 10 minutes, the mixture is quenched with aqueous sodium hydrogen carbonate. After filtration of the molecular sieves, the filtrate is diluted with dichloromethane, washed with water, concentrated and purified by chromatography on a column of silica gel to give 560 mg of compound 139.

TLC: Rf=0.50, silica gel, 3/7 v/v toluene/ethyl acetate

PREPARATION 125

Methyl O-(Benzyl 2,3-Di-O-methyl-β-D-
glucopyranosyluronate)-(1→4)-O-(3-O-acetyl-2-O-
benzyl-6-O-methyl-α-D-glucopyranosyl)-(1→4)-O-
(benzyl 2,3-di-O-Methyl-α-L-idopyranosyluronate)-
(1→4)-2,3-di-O-benzyl-6-O-methyl-α-D-
glucopyranoside (140)

Compound 139 (532.6 mg) is dissolved in pyridine (1.9 ml) and a mixture of acetic acid (2.4 ml) and hydrazine hydrate (0.3 ml) in pyridine (1.9 ml) is added at room temperature. After stirring for 9 minutes, dichloromethane and water are added. The organic phase is separated out and washed successively with 0.1 N hydrochloric acid, aqueous sodium hydrogen carbonate and water. The organic phase is concentrated and purified by chromatography on a column of silica gel to give 451 mg or compound 140.

TLC: Rf=0.45, silica gel, 3/7 v/v toluene/ethyl acetate

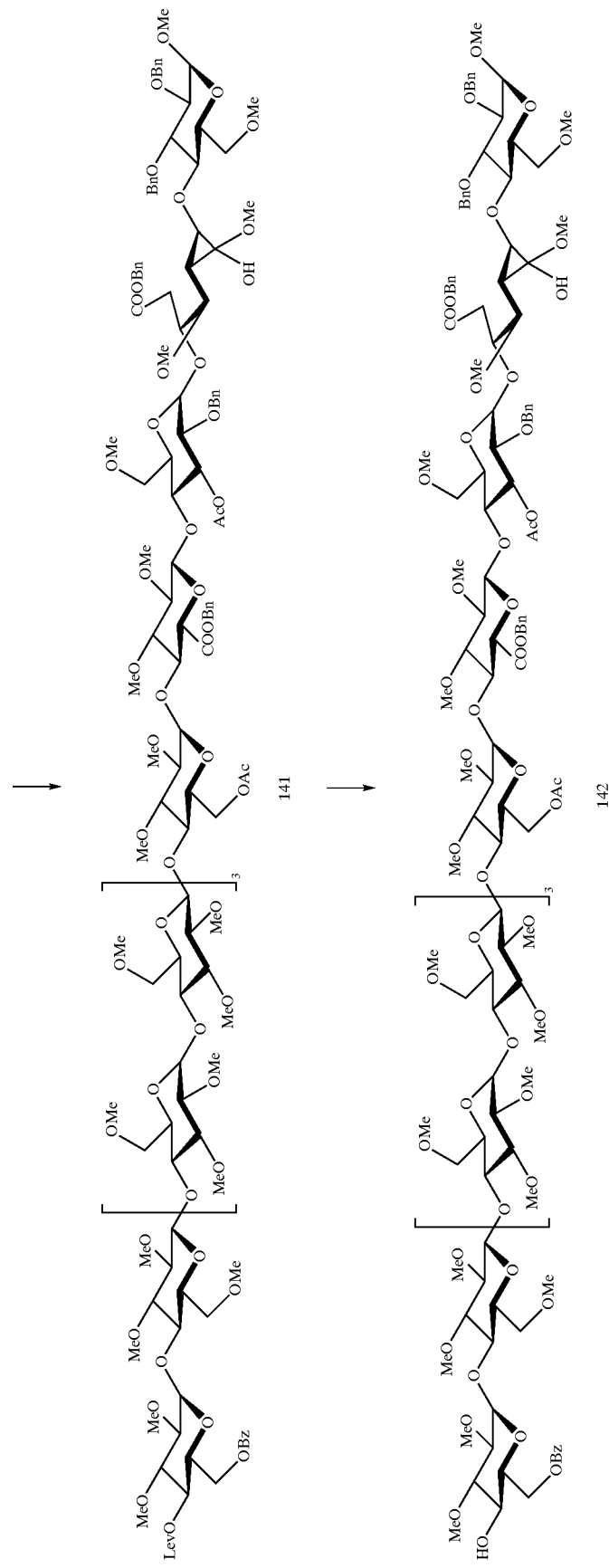

PREPARATION 126

Methyl O-(6-O-Benzoyl-4-O-levulinyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-O-(6-O-acetyl-2,3-di-O-methyl-α-D-glucopyranosyl)-(1→4)-O-(benzyl 2,3-di-O-Methyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-methyl-α-L-idopyranosyluronate)-(1→4)-2,3-di-O-benzyl-6-O-methyl-α-D-glucopyranoside (141)

A mixture of compound 117 (1→44 mg, 0.064 mmol) and compound 140 (76 g, 0.058 mmol) is co-evaporated with toluene and dissolved in 1/2 v/v dichloromethane/diethyl ether (3.0 ml). 4 Å molecular sieves (140 mg) are added under a nitrogen atmosphere and the mixture is cooled to 0° C. Tert-butyldimethylsilyl trifluoromethanesulphonate (128 μl of a 0.1 molar solution in dichloromethane) is added and, after 15 minutes, the mixture is quenched with sodium hydrogen carbonate solution. After extraction with water and dichloromethane, the organic phase is dried and concentrated. The product is first purified by chromatography on Sephadex LH 20 (1/1 v/v dichloromethane/methanol) and then by chromatography on a column of silica gel, to give 124 mg of compound 141 in an α/β ratio of 8/2.

TLC: Rf=0.60, silica gel, 1/1 v/v toluene/acetone

PREPARATION 127

Methyl O-(6-O-Benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]₃-O-(6-O-acetyl-2,3-di-O-methyl-α-D-glucopyranosyl)-(1→4)-O-(benzyl 2,3-di-O-Methyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-Methyl-α-L-idopyranosyluronate)-(1→4)-2,3-di-O-benzyl-6-O-methyl-α-D-glucopyranoside (142)

Compound 141 is converted into compound 142 according to the procedure described for the preparation of compound 140.

Compound 142 is isolated as an 8/2 α/β mixture.
TLC: Rf=0.45, silica gel, 1/1 v/v toluene/acetone

SCHEME 32

Synthesis of the trisaccharide 147

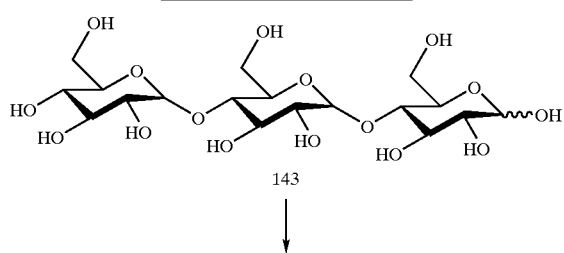

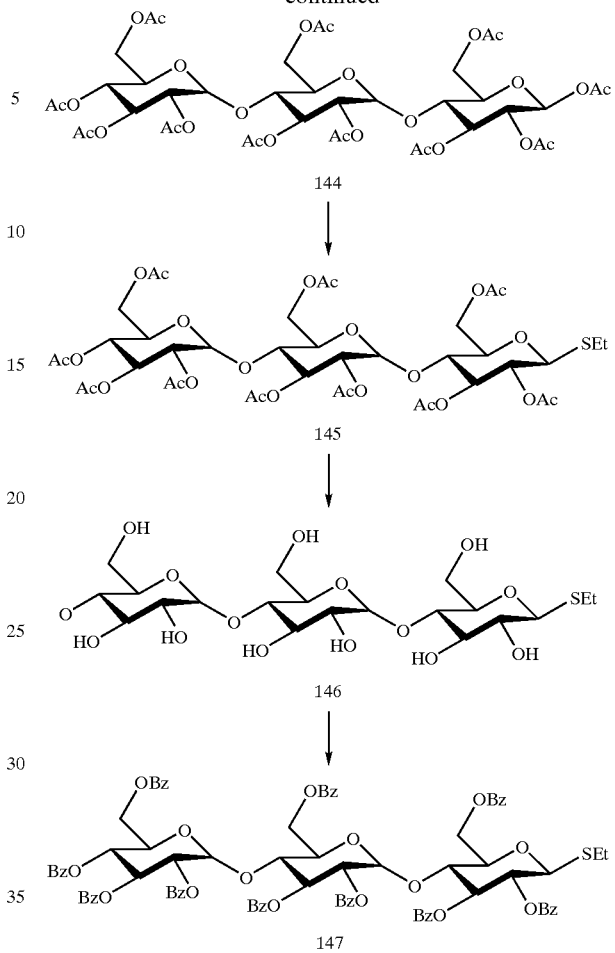

PREPARATION 128

O-(2,3,4,6-Tetra-O-acetyl-α-D-glucopyranosyl)-(1→4)-O-(2,3, 6-tri-O-acetyl-α-D-glucopyranosyl)-(1→4)-1,2,3,6-tetra-O-acetyl-β-D-glucopyranose (144)

Maltotriose (7 g, 13.9 mmol) (commercially available) is added portionwise to a suspension of sodium acetate (7 g, 85 mmol) in acetic anhydride (70 ml) at 155° C. After 15 minutes, the clear solution is cooled and quenched with ice-water (700 ml). After extraction with ethyl acetate, the organic phase is washed with water, dried over magnesium sulphate, filtered and concentrated to give 13.1 g of compound 144.

TLC: Rf=0.53, silica gel, 7/3 v/v dichloromethane/ethyl acetate

PREPARATION 129

Ethyl O-(2,3,4,6-Tetra-O-acetyl-α-D-glucopyranosyl)-(1→4)-O-(2,3,6-tri-O-acetyl-α-D-glucopyranosyl)-(1→4)-2,3,6-tri-O-acetyl-1-thio-β-D-glucopyranoside (145)

Compound 144 (13 g, 13.5 mmol) is dissolved in toluene (80 ml). Ethanethiol (1.97 ml, 26.9 mmol) and boron trifluoride diethyl etherate (13.7 ml of a one molar solution in toluene) is added under a nitrogen atmosphere. After stirring for 60 hours, the mixture is diluted with water and dichloromethane. After extraction, the organic phase is washed with 10% sodium hydrogen carbonate solution and water, dried, filtered and concentrated. The crude product is purified by chromatography on a column of silica gel to give 8.6 g of compound 145.

TLC: Rf=0.60, silica gel, 7/3 v/v dichloromethane/ethyl acetate

PREPARATION 130

Ethyl O-(α-D-Glucopyranosyl)-(1→4)-O-(α-D-glucopyranosyl)-(1→4)-1-thio-β-D-glucopyranoside (146)

Compound 145 is converted into compound 146 according to the procedure described for the preparation of compound 95.

TLC: Rf=0.80, silica gel, 13/7/1.6/4 v/v/v/v ethyl acetate/pyridine/acetic acid/water

PREPARATION 131

Ethyl O-(2,3,4,6-Tetra-O-benzoyl-α-D-glucopyranosyl)-(1→4)-O-(2,3,6-tri-O-Benzoyl-α-D-glucopyranosyl)-(1→4)-2,3,6-tri-O-benzoyl-1-thio-β-D-glucopyranoside (147)

Compound 146 is converted into compound 147 according to the procedure described for the preparation of compound 92.

TLC: Rf=0.50, silica gel, 9/1 v/v toluene/ethyl acetate

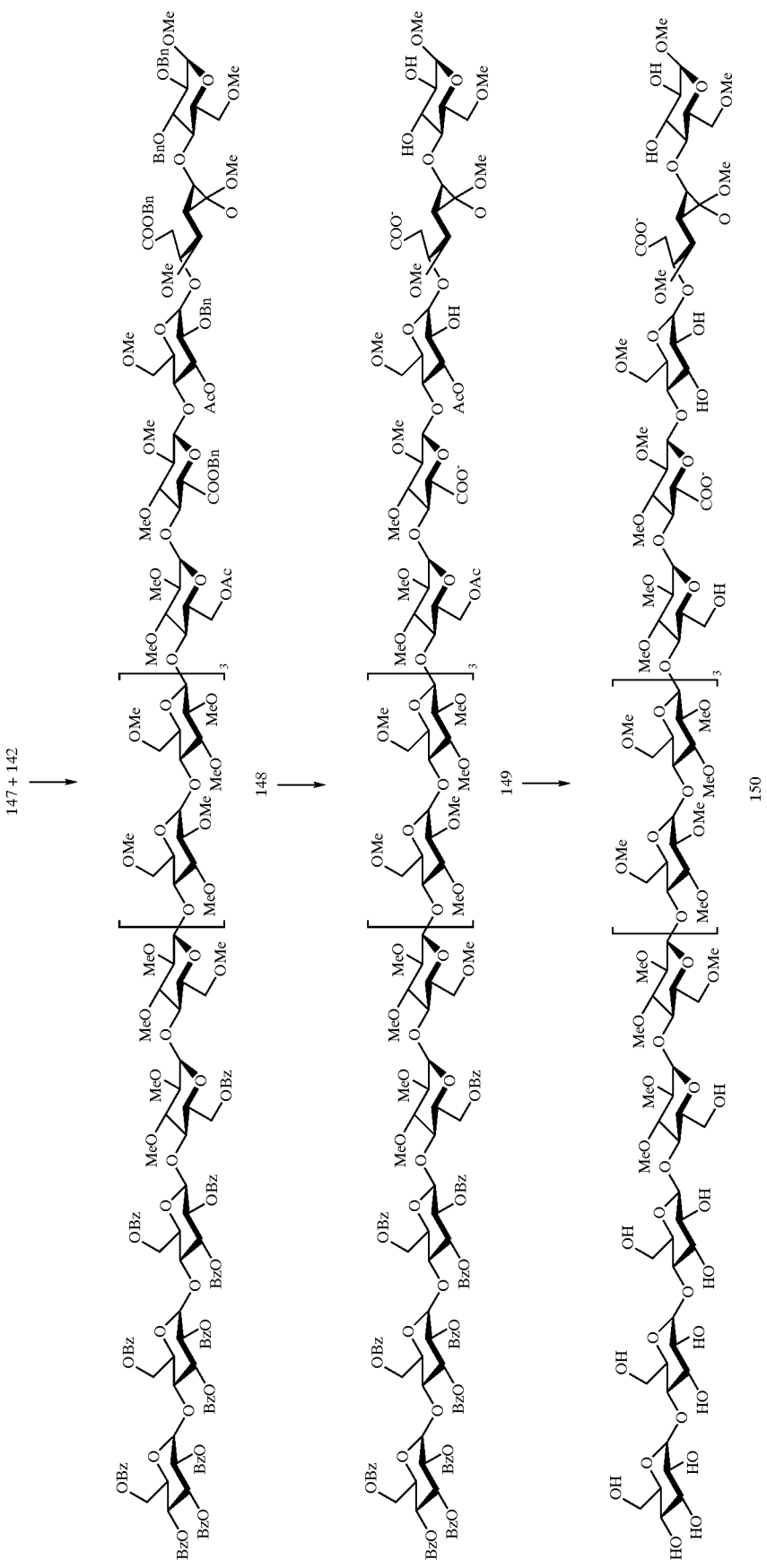

PREPARATION 132

Methyl O-(2,3,4,6-Tetra-O-Benzoyl-α-D-glucopyranosyl)-(1→4)-O-(2,3,6-tri-O-benzoyl-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(6-O-acetyl-2,3-di-O-methyl-α-D-glucopyranosyl)-(1→4)-O-(benzyl 2,3-di-O-Methyl-β-D-glucopyranosyluronate)-(1→4)-O-(3-O-acetyl-2-O-benzyl-6-O-methyl-α-D-glucopyranosyl)-(1→4)-O-(benzyl 2,3-di-O-Methyl-α-L-idopyranosyluronate)-(1→4)-2,3-di-O-benzyl-6-O-methyl-α-D-glucopyranoside (148)

The thioglycoside 147 (105 mg, 0.066 mmol) and the acceptor 142 (55 mg, 0.017 mmol), (α/β of 8/2) are coupled according to the procedure described for compound 109. The product is first purified by chromatography on Sephadex LH 20 (1/1 dichloromethane/methanol) and then by chromatography on a column of silica gel (9/0.5/0.5 v/v/v diethyl ether/ethyl acetate/ethanol) to give 49 mg of compound 148.
TLC: Rf=0.30, silica gel, 85/7.5/7.5 v/v/v diethyl ether/ethyl acetate/ethanol

PREPARATION 133

Methyl O-(2,3,4,6-Tetra-O-benzoyl-α-D-glucopyranosyl)-(1→4)-O-(2,3,6-tri-O-benzoyl-α-D-glucopyranosyl)-(1→4)-O-(2,3,6-tri-O-benzoyl-β-D-glucopyranosyl)-(1→4)-O-(6-O-benzoyl-2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(6-O-acetyl-2,3-di-O-methyl-α-D-glucopyranosyl)-(1→4)-O-(2,3-di-O-methyl-β-D-glucopyranosyluronic Acid)-(1-4)-O-(3-O-acetyl-6-O-methyl-α-D-glucopyranosyl)-(1→4)-O-(2,3-di-O-methyl-α-L-idopyranosyluronic Acid)-(1→4)-6-O-methyl-α-D-glucopyranoside (149)

A solution of compound 148 (47 mg, 0.01 mmol) in ethyl acetate (10 ml) is stirred under a nitrogen atmosphere in the presence of 10% palladium-on-charcoal (90% w/w relative to compound 148) for 3 hours and filtered. The filtrate is concentrated to give 42 mg of compound 149.
TLC: Rf=0.35, silica gel, 20/7/1.6/4 v/v/v/v ethyl acetate/pyridine/acetic acid/water

PREPARATION 134

Methyl O-(α-D-Glucopyranosyl)-(1→4)-O-(α-D-Glucopyranosyl)-(1→4)-O-(β-D-glucopyranosyl)-(1→4)-O-(2,3-di-O-methyl-α-D-glucopyranosyl)-(1→4)-O-(2,3,6-tri-O-methyl-β-D-glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(2,3-di-O-methyl-α-D-glucopyranosyl)-(1→4)-O-(2,3-di-O-methyl-β-D-glucopyranosyluronic Acid)-(1→4)-O-(6-O-methyl-α-D-glucopyranosyl)-(1→4)-O-(2,3-di-O-methyl-α-L-idopyranosyluronic Acid)-(1→4)-6-O-methyl-α-D-glucopyranoside (150)

A mixture of methanol (0.22 ml) and 0.66 N sodium hydroxide solution (0.66 ml) is added to compound 149 (41 mg, 0.01 mmol) followed by stirring for 20 hours at room temperature. The mixture is diluted with water and acidified with 0.5 N of 0.5 N hydrochloric acid solution in order to obtain a pH of 6.5. After concentration, the pure product is desalinated on a column of Sephadex G-25, using 9/1 v/v water/actetonitrile. The hexadecasaccharide fractions are combined and freeze-dried to give 26 mg of compound 150 as an amorphous white powder.
TLC: Rf=0.35, silica gel, 8/7/1.6/4 v/v/v/v ethyl acetate/pyridine/acetic acid/water

PREPARATION 135

6-O-Tert-butyldimethylsilyl-1,2-O-isopropylidene-3-O-methyl-α-D-glucofuranose (152)

The diol 151 (10 g, 42.7 mmol) is taken up in anhydrous dichloromethane (100 ml) and tert-butyldimethylsilyl chloride (7.1 g, 47.3 mmol) and imidazole (5.8 g, 85.3 mmol) are added. The reaction mixture is stirred at room temperature. After 2 hours, the mixture is diluted in dichloromethane and washed with water. The organic phase is dried over magnesium sulphate and concentrated and the residue is purified by chromatography on a column of silica gel (1/9 v/v ethyl acetate/cyclohexane) in order to obtain the desired product 152 (11.9 g, 80%) in the form of a syrup. $[\alpha]_D$–34° (c 1.9, CHCl$_3$).

PREPARATION 136

6-O-Tert-butyldimethylsilyl-1,2-O-isopropylidene-3-O-methyl-5-C-vinyl-α-D-glucofuranose (154)

Oxalyl chloride (3.2 ml, 36.8 mmol) and dimethyl sulphoxide (5.2 ml, 73.4 mmol) are added, at –78° C., to anhydrous dichloromethane (40 ml) and the mixture is stirred for 30 minutes. Next, compound 152 (6.4 g, 18.4 mmol) is added and the mixture is stirred for a further 1 hour. Triethylamine (15.3 ml, 110.0 mmol) is then added and, after 30 minutes, the reaction mixture is diluted in dichloromethane. Standard processing allows the 5-ulose compound (153) to be obtained, which is used directly for the following reaction. The crude ketone 153 is taken up in anhydrous tetrahydrofuran (100 ml) and 1M vinylmagnesium bromide solution in tetrahydrofuran (28 ml, 27.6 mmol) is added at 0C. After 1 hour, the reaction mixture is diluted with ammonium chloride and washed with water. The organic phase is dried over magnesium sulphate and concentrated and the residue is purified by chromatography on a column of silica gel (1/9 v/v ethyl acetate/cyclohexane) in order to obtain the desired compound 154 (70%, 4.8 g) in the form of a syrup. $[\alpha]_D$–40° (c 1.3, CHCl$_3$).

Anal. calculated: C, 57.72, H, 9.15. Found: C, 57.77, H, 9.23.

PREPARATION 137

1,2,4,6-Tetra-O-acetyl-3-O-methyl-5-C-vinyl-β-D-glucopyranose (156)

Compound 154 (3.5 g, 9.4 mmol) is taken up in water (50 ml); IR-120 resin (1 g) is added thereto and the mixture is heated at 80° C. for 6 hours. The resin is filtered off and the filtrate is concentrated. The crude product 155b is acetylated using acetic anhydride (12 ml) and pyridine (13 ml). The excess acetic anhydride is destroyed with methanol and the solvents are concentrated. The residue is extracted with water and dichloromethane. The organic phase is dried over magnesium sulphate, concentrated and, after purification by chromatography on a column of silica (3/2 v/v ethyl acetate/cyclohexane), the tetraacetate compound 156 is obtained in the form of a solid (75%, 2.7 g). m.p. 50° C. $[\alpha]_D$–84° (c 1.6, CHCl$_3$).

Anal. calculated: C, 52.47, H, 6.19. Found: C. 52.51, H, 6.19; Cl-MS: 406 (M+NH$_4$), 389 (M+1).

PREPARATION 138

Methyl 2,3,6-Tri-O-benzyl-4-O-(2,4,6-tri-O-acetyl-3-O-methyl-5-C-vinyl-β-D-glucopyranosyl)-α-D-glucopyranoside (158)

Compound 156 (1.6 g, 4.1 mmol) and compound 157 2.1 g, 4.5 mmol) (P. J. Garegg and H. Hultberg, Carbohydr. Res. 1981, 93, C10) are dissolved in anhydrous dichloromethane (50 ml) and molecular sieves (4.0 g) are added. The reaction mixture is stirred at room temperature for one hour and TMSOTf (0.95 ml, 5.2 mmol) is then added at –78° C. The reaction mixture is then left to, warm s lowly to room temperature. After 2 hours, the reaction mixture is neutralized with triethylamine and filtered through Celite; the filtrate is washed with water. The organic phase is dried over magnesium sulphate and concentrated and the residue is purified by chromatography on silica (4/1 v/v ethyl acetate/cyclohexane) in order to obtain the desired compound 158 (2.77 g, 85%) in the form of a solid. m.p. 47° C. $[\alpha]_D$–36° (c 0.6, CHCl$_3$).

Anal. calculated: C, 65.14, H, 6.61. Found: C, 65.09, H, 6.70.

PREPARATION 139

Methyl 2,3,6-O-Tri-O-benzyl-4-O-(4 6-O-isopropylidene-3-O-methyl-5-C-vinyl-β-D-glucopyranosyl)-α-D-glucopyranoside (160)

Compound 158 (2.7 g, 3.4 mmol) is dissolved in methanol (40 ml). Sodium (catalytic) is added at 0° C. and the mixture is stirred at room temperature for 3 hours. The solvent is concentrated and the residue 159 is taken up in anhydrous acetone (40 ml) and 2,2-dimethoxypropane (2 ml) and p-toluenesulphonic acid (catalytic) are added. The reaction mixture is stirred at room temperature overnight. The solvent is evaporated off and the residue is taken up in chloroform and washed with water. The organic phase is dried over magnesium sulphate and concentrated and the residue is purified by chromatography on a column of silica (1/1 v/v ethyl acetate/cyclohexane) in order to obtain the 4',6'-isopropylidene-O-derivative 160 (1.7 g, 70%) in the form of a solid. m.p. 55° C. $[\alpha]_D$+13° (c 0.8, CHCl$_3$).

Anal. calculated: C, 67.97, H, 7.13. Found: C, 67.87, H, 7.16; Cl-MS: 707 (M+1), 724 (M+NH$_4$).

PREPARATION 140

Methyl 2,3,6-Tri-O-benzyl-4-O-(4,6-O-isopropylidene-3-O-methyl-5-C-vinyl-β-D-mannopyranosyl)-α-D-glucopyranoside (162)

Oxalyl chloride (0.35 ml, 4.0 mmol) and anhydrous DMSO (0.57 ml, 8.0 mmol) in anhydrous dichloromethane (10 ml) are stirred at –78° C. for 30 minutes. Compound 160 (1.4 g, 2.0 mmol) in anhydrous dichloromethane (10 ml) is added to the solution and the mixture is stirred for a further 45 minutes. The reaction mixture is neutralized by addition of anhydrous triethylamine (1.7 ml, 12.0 mmol) and is then diluted with dichloromethane. After washing with water, the organic phase is dried over magnesium sulphate and concentrated and the residue 161 is used directly for the following reaction without purification. The ketone 161 is taken up in anhydrous tetrahydrofuran (15 ml) and a 1N solution of super hydride in tetrahydrofuran (4 ml, 4.0 mmol) is added at –78° C. The reaction mixture is stirred at room temperature for 1 hour and 5% sodium hydroxide (2 ml) and hydrogen peroxide (1 ml) are then added. The solvent is evaporated off and the residue is taken up in diethyl acetate and washed with water. The organic phase is dried over magnesium sulphate and concentrated and the residue is purified by chromatography (2/1 v/v ethyl acetate/cyclohexane) in order to obtain compound 162 (1.0 g, 70%). $[\alpha]_D$–11° (c 0.5, CHCl$_3$); Cl-MS: 724 (M+18), 707 (M+1).

PREPARATION 141

Methyl 2,3,6-Tri-O-benzyl-4-O-(2-O-acetyl-3-O-methyl-5-C-vinyl-β-D-mannopyranosyl)-α-D-glucopyranoside (164)

Compound 162 (940 mg, 1.3 mmol) is dissolved in pyridine (3 ml) and acetic anhydride (0.3 ml) is added. The reaction mixture is stirred at room temperature for 3 hours. The excess pyridine and acetic anhydride is evaporated off and the residue 163 is used directly for the deprotection of the isopropylidene using 80 acetic acid (5 ml) at 60° C. for 2 hours. The excess acetic acid is evaporated off and the residue is purified by chromatography on a column of silica gel (4/1 v/v ethyl acetate/cyclohexane) in order to obtain the diol 164 (660 mg, 70%) in the form of a solid. m.p. 53° C. $[\alpha]_D$–10° (c 0.8, CHCl$_3$); Cl-MS: 709 (M+1), 726 (M+18).

PREPARATION 142

Methyl 2,3,6-Tri-O-benzyl-4-(2-O-acetyl-3-O-methyl-6-O-tosyl-5-C-vinyl-β-D-mannopyranosyl)-α-D-glucopyranose (165)

Compound 164 (600 mg, 0.9 mmol) is dissolved in pyridine (3 ml) and tosyl chloride (240 mg, 1.3 mmol) is added. The reaction mixture is stirred at room temperature for 3 hours. The solvent is evaporated off and the residue is diluted with chloroform and washed with water. The organic phase is dried over magnesium sulphate and concentrated and the residue is purified by chromatography on a column of silica gel (1/1 v/v ethyl acetate/cyclohexane) in order to obtain the tosyl compound 165 (297 mg, 80%) in the form of a syrup. $[\alpha]_D$–26° (c 0.8, CHCl$_3$).

PREPARATION 143

Methyl 2,3,6-Tri-O-benzyl-4-(2,6-anhydro-3-O-methyl-5-C-vinyl-β-D-mannopyranosyl)-α-D-glucopyranoside (166)

Compound 165 (550 mg, 0.6 mmol) is taken up in ethanol (3 ml) and a 0.1N solution of ethanolic sodium hydroxide (5 ml) is then added. The reaction mixture is heated at 70° C. for 3 hours and then neutralized with IR-120 resin (H form) and filtered through Celite. After concentration, the residue is purified by chromatography on a column of silica gel (1/1 v/v ethyl acetate/cyclohexane) in order to obtain compound 166 (292 mg, 70%) in the form of a syrup. $[\alpha]_D$+13° (c 0.5, CHCl$_3$); Cl-MS: 666 (M+18).

PREPARATION 144

Methyl 2,3,6-Tri-O-benzyl-4-(benzyl 3-O-methyl-2-O-5-C-methylidene-α-L-idopyranuronate)-α-D-glucopyranoside (167)

Compound 166 (260 mg, 0.4 mmol) is dissolved in dichloromethane (20 ml), the solution is stirred at –78° C.

and ozone is then bubbled through for 30 seconds. The colour of the solution becomes pale yellow. Dimethyl sulphide is added to the solution and the reaction mixture is then washed with water. The organic phase is dried over magnesium sulphate and concentrated and is passed directly into the following reaction without further purification. The crude aldehyde is taken up in tert-butanol (16 ml) and 2-methyl-2-butene (5 ml) and water (16 ml) are added. $NaH_2PO_4$ (700 mg) and $NaClO_D$ (700 mg) are then added successively to the mixture. The suspension is stirred vigorously at room temperature overnight, diluted with water and extracted with ethyl acetate. The organic phase is dried over magnesium sulphate, concentrated and then passed directly into the following reaction. The crude acid is taken up in dimethyl formamide (25 ml) and tetrabutylammonium iodide (0.7 g, 2.0 mmol), potassium bicarbonate (0.25 g, 2.5 mmol) and benzyl bromide (0.250 ml, 2.1 mmol) are added. The reaction mixture is stirred at room temperature for 5 hours. The reaction mixture is extracted with water and ether. The ether phase is dried over magnesium sulphate and concentrated and the residue is purified by chromatography on a column of silica gel (2/1 v/v ethyl acetate/cyclohexane) in order to obtain the derivative 167 (236 mg, 80%) in the form of a syrup; Cl-MS: 774 (M+18).

SCHEME 34
Preparation of a synthon which is useful for the synthesis of a pentassaccharide Pe for which the configuration of the L-iduronic acid is locked (III.1)

1. Preparation of the donor monosaccharide

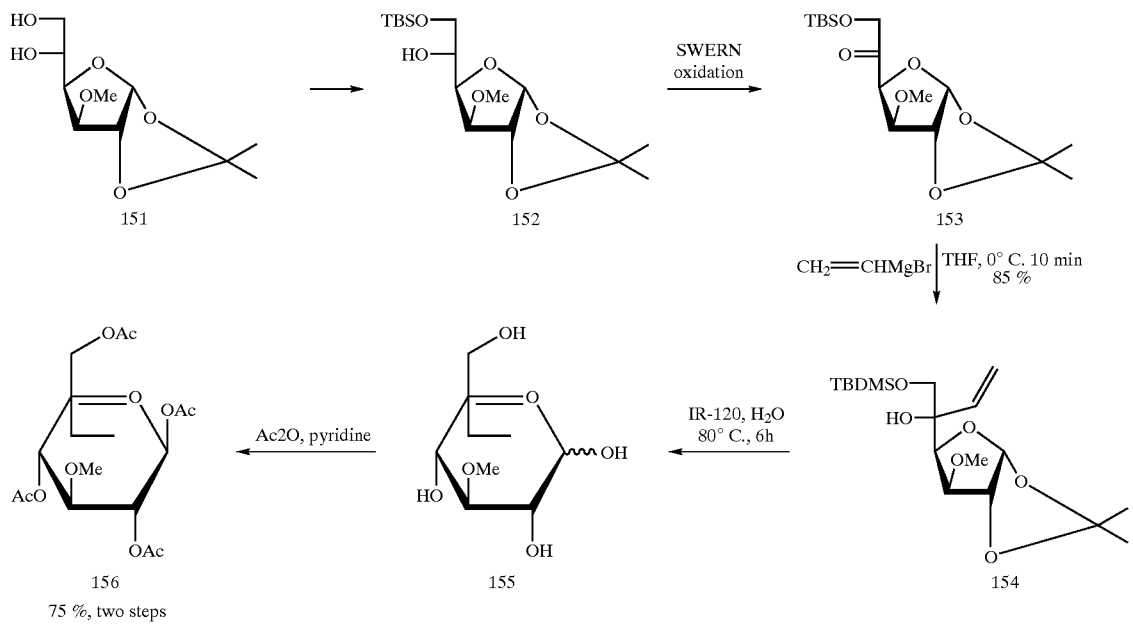

2. Preparation and first transformations of the disaccharide

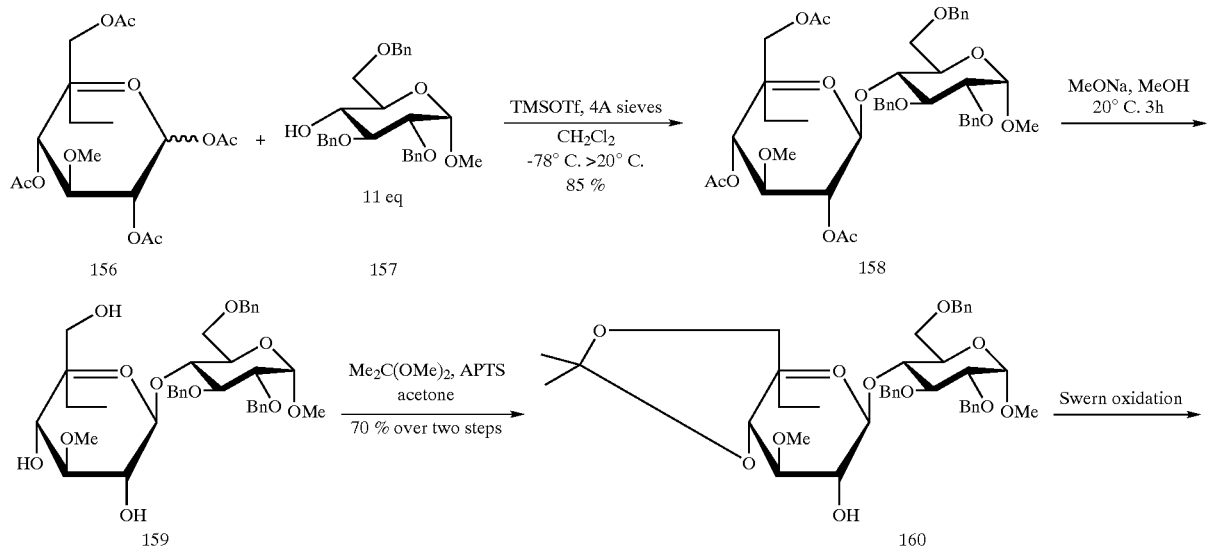

-continued
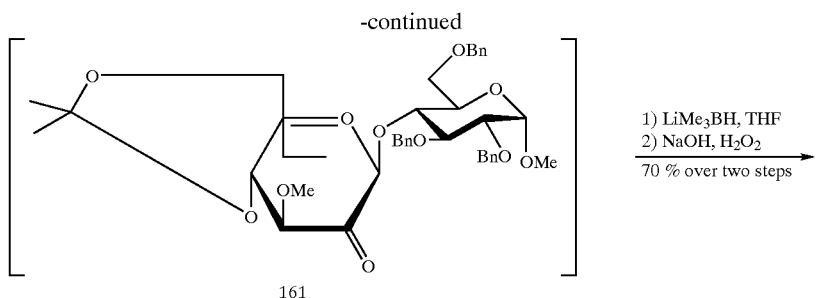
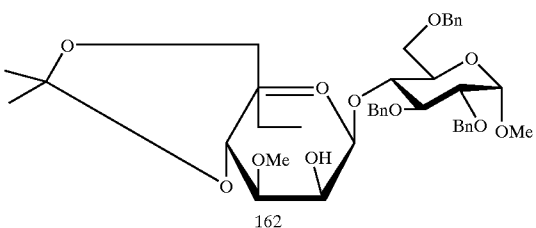
3. Construction of the bicyclic system
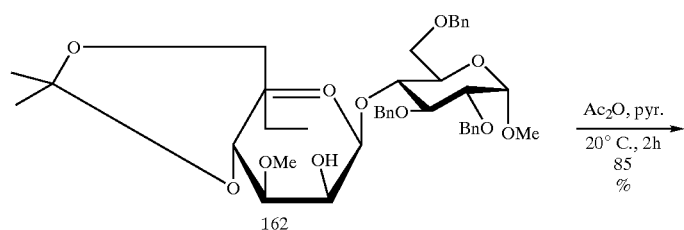
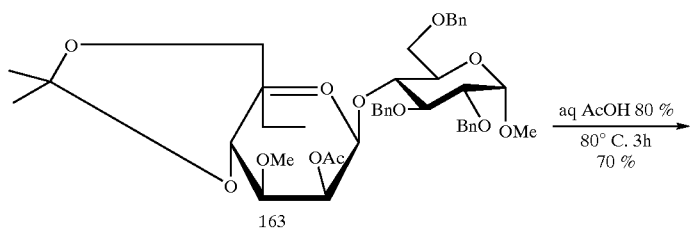
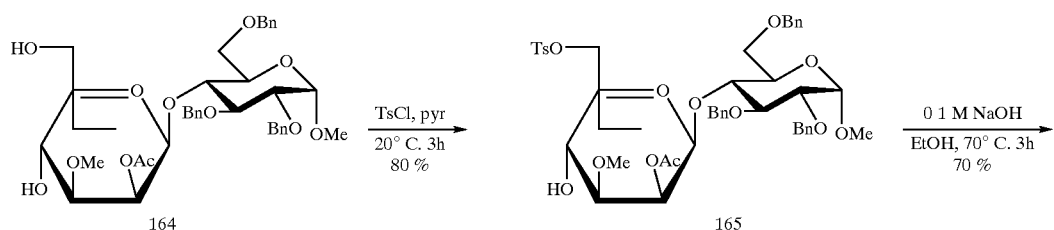
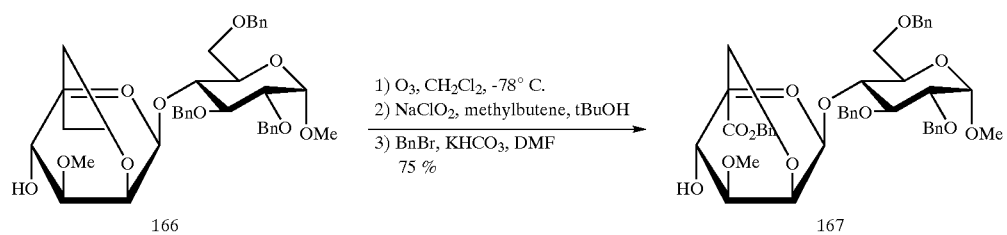

EXAMPLE 1

Methyl O-(3-O-Methyl-2,4,6-tri-O-sulpho-α-D-glucopyrano-syl)-(1-4)-O-(3-O-methyl-2,6-di-O-sulpho-O-D-gluco-pyranosyl)-(1-4)-[O-(3-O-methyl-2,6-di-O-sulpho-α-D-(glucopyranosyl)-(1-4)-O-(3-O-methyl-2,6-di-O-sulpho-β-D-glucopyranosyl)-(1-4)]$_6$-O-(2,3-di-O-methyl-6-O-sulpho-α-D-(glucopyranosyl)-(1-4)-O-(2,3-di-O-methyl-β-D-glucopyranosyluronic acid)-(1-4)-O-(2,3,6-tri-O-sulpho-α-D-(glucopyranosyl)-(1-4)-O-(2,3-di-O-methyl-α-L-idopyranosyluronic acid)-(1-4)-2,3,6-tri-O-sulpho-α-D-glucopyranoside, sodium salt (168).

Compound 31 is treated according to Method 5 in order to give 168 (80% over the three steps). [α]$_D$+41 (c=0.8, water). ESIMS, negative mode: monoisotopic mass= 7133.26; chemical mass=7138.90; experimental mass= 7137.26±0.0 a.m.u. $_1$H NMR (D$_2$O) δ of the main anomeric protons: 5.71; 5.48; 5.46; 5.44; 5.17; 5.08; 4.81; 4.78; 4.67 ppm.

An identical procedure allows compounds 169 and 170 to be obtained.

EXAMPLE 4

Methyl O-(2,3-Di-O-methyl-4,6-di-O-sulpho-α-D-glucopyranosyl)-(1-4)-[O-(2,3-di-O-methyl-6-O-sulpho-α-D-glucopyranosyl)-(1-4)]$_{15}$-O-(2,3-di-O-methyl-β-D-glucopyranosyluronic acid)-(1-4)-O-(2,3,6-tri-O-sulpho-β-D-(glucopyranosyl)-(1-4)-O-(2,3-di-O-methyl-α-L-idopyranosyluronic acid)-(1-4)-2,3,6-tri-O-sulpho-α-D-glucopyranoside, sodium salt (171).

Compound 51 (55 mg, 10.5 mmol) is treated according to Method 5 in order to obtain, after freeze-drying, the sulphated product 187 (50 mg, 77% over three steps). [α]$_D$+107 (c=0.52, water). ESIMS, positive mode: monoisotopic mass 6194.16; chemical mass=6198.83; experimental mass= 6195.33±1.79. $^1$H NMR (D$_2$O) δ of the main anomeric protons: 5.71; 5.67; 5.48; 5.43; 5.17; 5.10; 4.68 ppm.

An identical procedure allows compounds 172 and 173 to be obtained.

TABLE I (I.1)

| Example number | t | [α]$_D$ |
|---|---|---|
| 2 compound 169 | 5 | +39 |
| 3 compound 170 | 6 | +38 |

TABLE II (I.2)

| Example number | t | [α]$_D$ |
|---|---|---|
| 5 compound 172 | 5 | +119 |
| 6 compound 173 | 6 | +124 |

EXAMPLE 7

Methyl O-(3-O-Methyl-2,4,6-tri-O-sulpho-α-D-glucopyranosyl)-(1-4)-O-(3-O-methyl-2,6-di-O-sulpho-β-D-glucopyranosyl)-(1-4)-O-(3-O-methyl-2,6-di-O-sulpho-α-D-glucopyranosyl)-(1-4)-O-(3-O-methyl-2,6-di-O-sulpho-β-D-(gluco-pyranosyl)-(1-4)-[O-(2,3,6-tri-O-methyl-α-D-glucopyranosyl)-(1-4)-O-(2,3,6-tri-O-methyl-β-D-glucopyranosyl)-(1-4)]$_4$-O-(2,3-di-O-methyl-6-O-sulpho-α-D-(glucopyranosyl)-(1-4)-O-(2,3-di-O-methyl-β-D-glucopyranosyluronic acid)-(1-4)-O-(2,3,6-tri-O-sulpho-α-D-(glucopyranosyl)-(1-4)-O-(2,3-di-O-methyl-α-L-idopyranosyluronic acid)-(1-4)-2,3,6-tri-O-sulpho-α-D-glucopyranoside, sodium salt (174).

Compound 75 is treated according to Method 5 in order to give 174 (84% over the three steps). $[\alpha]_D$+62 (c=0.46, water). ESIMS, positive mode: monoisotopic mass= 4966.39; chemical mass=4970.04; experimental mass= 4969.63±0.78 a.m.u. $_1$H NMR (D$_2$O) δ of the main anomeric protons: 5.69; 5.63; 5.57; 5.46; 5.44; 5.41; 5.15; 5.06; 4.79; 4.66; 4.62; 4.41 ppm.

By working according to Example 7 and using suitable intermediates, Examples 8 to 12 described in Table III below are prepared.

EXAMPLE 13

Methyl O-(2,3,4,6-Tetra-O-sulpho-α-D-(glucopyranosyl)-(1→4)-O-(2,3,6-tri-O-sulpho-α-D-(glucopyranosyl)-(1→4)-O-(2,3,6-tri-O-sulpho-β-D-(glucopyranosyl)-1→4)-O-(2,3-di-O-methyl-6-O-sulpho-α-D-(glucopyranosyl)-(1→4)-O-(2,3,6-tri-O-methyl-β-D-(glucopyranosyl)-(1→4)-[O-(2,3,6-tri-O-methyl-α-D-glucopyranosyl)-(1→4)-O-(2,3,6-tri-O-methyl-β-D-glucopyranosyl)-(1→4)]$_3$-O-(2,3-di-O-methyl-6-O-sulpho-α-D-(glucopyranosyl)-(1→4)-O-(2,3-di-O-methyl-β-D-glucopyranosyluronic acid)-(1→4)-O-(6-O-methyl-2,3-di-O-sulpho-α-D-(gluco-pyranosyl)-(1→4)-O-(2,3-di-O-methyl-α-L-idopyranosyluronic acid)-(1→4)-6-O-methyl-2,3-di-O-sulpho-α-D-glucopyranoside (180)

The fully deprotected hexadecasaccharide 150 (26 mg, 0.0084 mmol) is dissolved in dimethylformamide (0.87 ml). Sulphur trioxide/triethylamine complex (125 mg, 0.67 mmol, 80 eq) is added, under a nitrogen atmosphere, and the mixture is stirred for 16 hours at 50° C. The mixture is cooled to 0° C. and aqueous sodium hydrogen carbonate (227 mg, 2.6 mmol) are added. The mixture is concentrated to a small volume and placed on a Sephadex G-25 column, eluted with 9/1 v/v water/acetonitrile. The appropriate fractions are separated, concentrated to a small volume, placed on a Dowex XW4 Na$^+$ ion-exchange column in water and

TABLE III (I.3)

| Example number | m | t | $[\alpha]_D$ |
|---|---|---|---|
| 8 compound 175 | 3 | 3 | +51 |
| 9 compound 176 | 1 | 5 | +65 |
| 10 compound 177 | 1 | 4 | +59 |
| 11 compound 178 | 2 | 3 | +47 |
| 12 compound 179 | 3 | 2 | +36 | the eluate is freeze-dried to give 37 mg of compound 151 as a white powder. $[\alpha]^{20}_D$=67.6 (c=1, water) MS ESI: molecular weight is 4370.6 (H$^+$ form) C$_{129}$H$_{222}$O$_{113}$S$_{16}$ (Theor. m.w.=4370.14).

NMR; shift of the anomeric protons (ppm): unit 1: 5.17; unit 2: 5.03; unit 3: 5.41; unit 4: 4.42; unit 5: 5.49; unit 6: 4.66; units 7, 9 and 11: 5.67; units 8, 10 and 12: 4.46; unit 13: 5.61; unit 14: 4.94; unit 15: 5.59 ppm; unit 16: 5.69.

SCHEME 35
Structure of the polysaccharide 180 (Example 13)

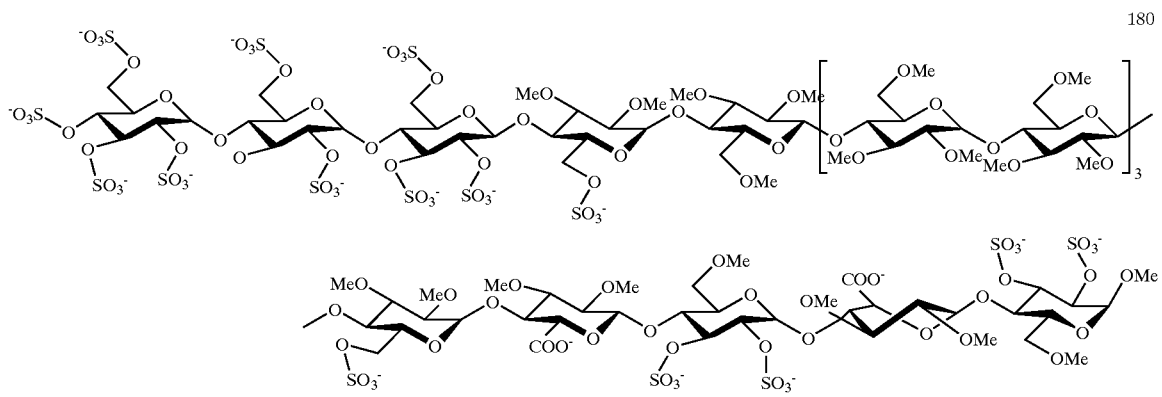

What is claimed is:

1. A polysaccharide comprising a region for binding to antithrombin III consisting of a sequence of five monosaccharides bearing in total two carboxylic acid functions and at least four sulpho groups, this region being bound directly at its non-reducing end by a thrombin-binding region comprising a sequence of 10 to 25 monosaccharide units chosen from hexoses, pentoses or deoxy sugars in which the hydroxyl groups are, independently, etherified with a $(C_1-C_6)$alkyl group or esterified in the form of sulpho groups, or a pharmaceutically acceptable salt thereof.

2. A polysaccharide according to claim 1 in the form of a salt with a pharmaceutically acceptable base or in the form of an acid, of formula:

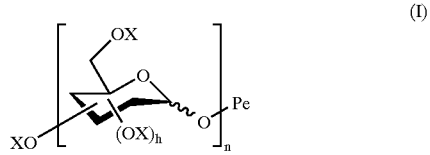

(I)

in which the wavy line denotes a bond either below or above the plane of the pyranose ring,

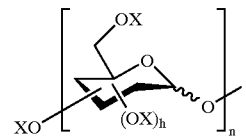

denotes a polysaccharide Po containing n identical or different monosaccharide units, which is linked via its anomeric carbon to Pe,

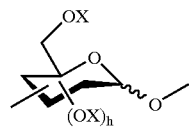

is a diagrammatic representation of a monosaccharide unit of pyranose structure chosen from hexoses, pentoses and the corresponding deoxy sugars, this unit being linked via its anomeric carbon to another monosaccharide unit, and the hydroxyl groups of this unit being substituted with identical or different groups —X, the groups X being chosen from $(C_1-C_6)$alkyl groups and sulpho groups, h is an integer from 1 to 3, n is an integer from 10 to 25, Pe represents a pentasaccharide of structure:

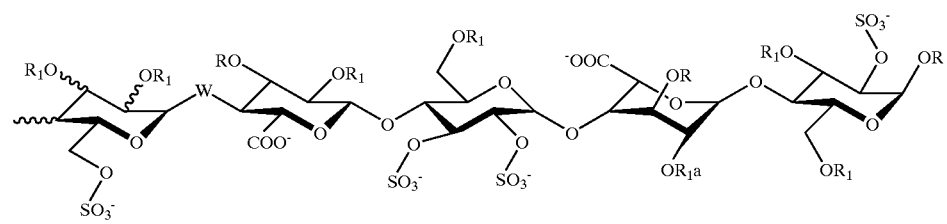

in which

R₁ represents a (C₁–C₆)alkyl or a sulpho group,

R₁a represents R₁ or constitutes, with the oxygen atom to which it is linked and the carbon atom bearing the carboxylic function on the same ring, a group

C—CH₂—O,

R represents a (C₁–C₆)alkyl group, and

W represents an oxygen atom or a methylene group.

3. An alkali metal salt of a polysaccharide according to claim 2.

4. A polysaccharide according to claim 2 in the form of a salt with a pharmaceutically acceptable base or in the form of an acid, of formula:

(I.A)

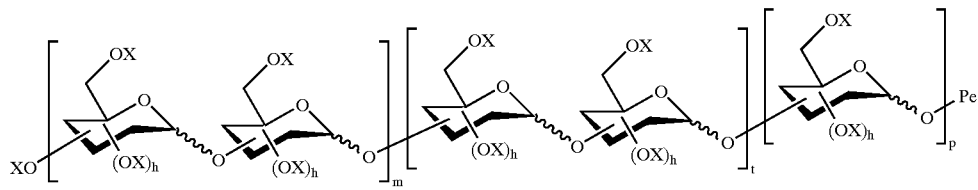

in which

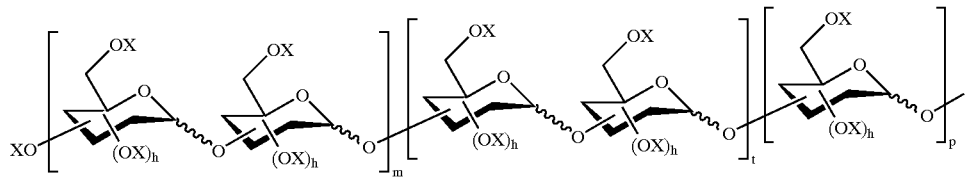

denotes a particular family of polysaccharides Po, linked via their anomeric carbon to Pe as defined for (I),

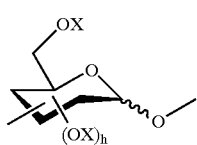

is as defined for (I), the OXs are as defined for (I) and, for the same monosaccharide, may be identical or different, h is as defined for (I)

the monosaccharides contained in [ ]ₘ form a disaccharide repeated m times, the monosaccharides contained in [ ]ₜ form a disaccharide repeated t times, m ranges from 1 to 8, t ranges from 0 to 5 and p ranges from 0 to 1, wherein 5≦m+t≦12.

5. A polysaccharide according to claim 2 in the form of a salt with a pharmaceutically acceptable base or in the form of an acid of formula:

(II.A)

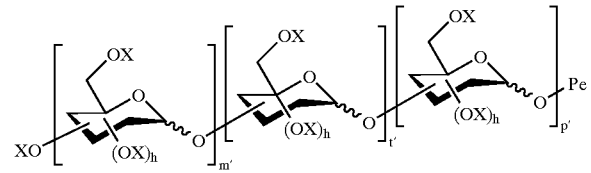

denotes a particular family of polysaccharides Po, linked via their anomeric carbon to Pe as defined for (I),

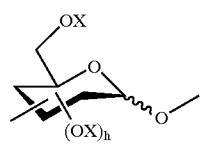

is as defined for (I), the OXs are as defined for (I) and, for the same monosaccharide, may be identical or different, h is as defined for (I)

the monosaccharide contained in [ ]ₘ' is repeated m' times, the monosaccharide contained in [ ]ₜ' is repeated t' times and the monosaccharide contained in [ ]ₚ' is repeated p' times, m' ranges from 1 to 5, t' ranges from 0 to 24 and p' ranges from 0 to 24, wherein 10≦m'+t'+p'≦25.

6. A polysaccharide according to claim 2 having the formula (I.1)

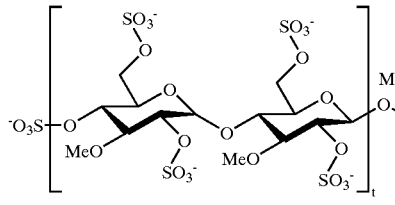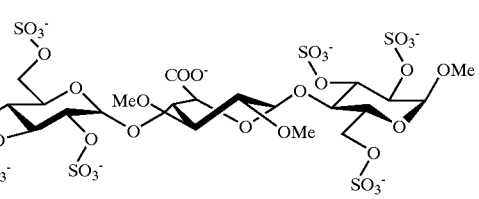

in which t is 5, 6 or 7 in the form of a salt with a pharmaceutically acceptable base or in the form of an acid.

7. A polysaccharide according to claim 2 having the formula (I.2)

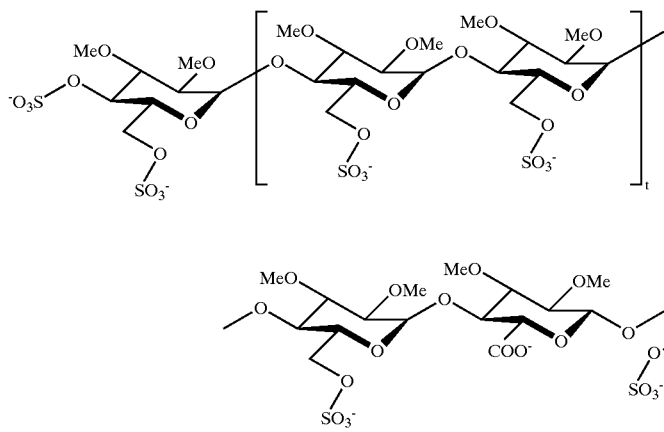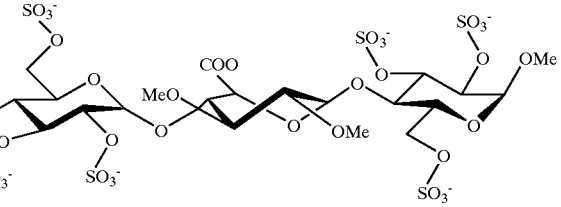

in which t is 5, 6 or 7 in the form of a salt with a pharmaceutically acceptable base or in the form of an acid.

8. A polysaccharide according to claim 2 having the formula in which t is 5, 6 or 7 in the form of a salt with a pharmaceutically acceptable base or in the form of an acid.

9. A polysaccharide selected from the group consisting of:

Methyl O-(3-O-methyl-2,4,6-tri-O-sulpho-a-D-(glucopyranosyl)-(1-4)-O-(3-O-methyl-2,6-di-O-sulpho-b-D-(glucopyranosyl)-(1-4)-[O-(3-O-methyl-2,6-di-O-sulpho-a-D-(glucopyranosyl)-(1-4)-O-(3-O-methyl-2,6-di-O-sulpho-b-D-(glucopyranosyl)-(1-4)]₄-O-(2,3-di-O-methyl-6-O-sulpho-a-D-(glucopyranosyl)-(1-4)-O-(2,3-di-O-methyl-b-D-glucopyranosyluronic acid)-(1-4)-O-(2,3,6-tri-O-sulpho-a-D-

(I.3)

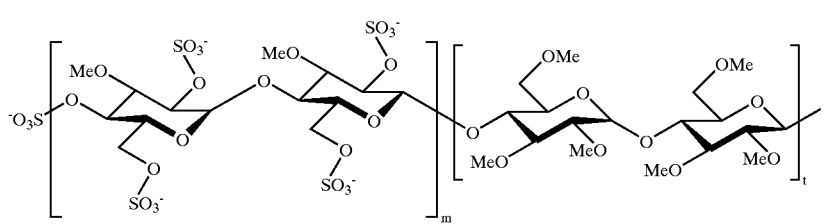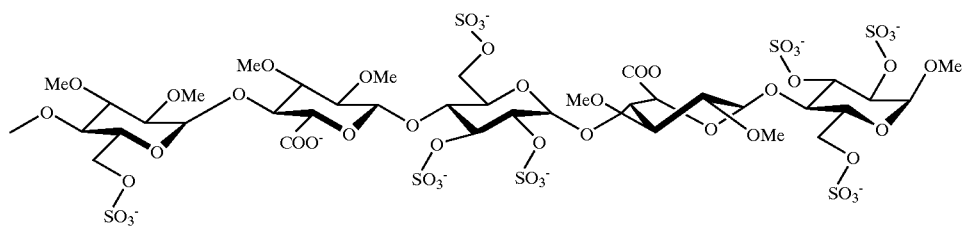

(glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-a-D-(glucopyranosyl)-(1-4)-O-(3-O-methyl-2,6-di-O-sulpho-b-D-(glucopyranosyl)-(1-4)-[O-(3-O-methyl-2,6-di-O-sulpho-a-D-(glucopyranosyl)-(1,4)-O-(3-O-methyl-2,6-di-O-sulpho-b-D-(glucopyranosyl)-(1-4)]$_5$-O-(2,3-di-O-methyl-6-O-sulpho-a-D-(glucopyranosyl)-(1-4)-O-(2,3-di-O-methyl-b-D-glucopyranosyluronic acid)-(1,4)-O-(2,3,6-tri-O-sulpho-a-D-(glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-a-D-(glucopyranosyl)-(1-4)-O-(3-O-methyl-2,6-di-O-sulpho-b-D-(glucopyranosyl)-(1-4)-[O-(3-O-methyl-2,6-di-O-sulpho-a-D-(glucopyranosyl)-(1-4)-O-(3-O-methyl-2,6-di-O-sulpho-b-D-(glucopyranosyl)-(1-4)]$_6$-O-(2,3-di-O-methyl-6-O-sulpho-a-D-(glucopyranosyl)-(1-4)-O-(2,3-di-O-methyl-b-D-glucopyranosyluronic acid)-(1-4)-O-(2,3,6-tri-O-sulpho-a-D-(glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(2,3-di-O-methyl-4,6-di-O-sulpho-a-D-(glucopyranosyl)-(1-4)-[O-(2,3-di-O-methyl-6-O-sulpho-a-D-(glucopyranosyl)-(1-4)-]$_{11}$-O-(2,3-di-O-methyl-b-D-glucopyranosyluronic acid)-(1,4)-O-(2,3,6-tri-O-sulpho-a-D-(glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(2,3-di-O-methyl-4,6-di-O-sulpho-a-D-(glucopyranosyl)-(1-4)-[O-(2,3-di-O-methyl-6-O-sulpho-a-D-(glucopyranosyl)-(1-4)-]$_{13}$-O-(2,3-di-O-methyl-b-D-glucopyranosyluronic acid)-(1-4)-O-(2,3,6-tri-O-sulpho-a-D-glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(2,3-di-O-methyl-4,6-di-O-sulpho-a-D-(glucopyranosyl)-(1-4)-[O-(2,3-di-O-methyl-6-O-sulpho-a-D-(glucopyranosyl)-(1-4)-]$_{15}$-O-(2,3-di-O-methyl-b-D-glucopyranosyluronic acid)-(1-4)-O-(2,3,6-tri-O-sulpho-a-D-glucopyranosyl)-(1-4)-O-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-[O-(3-O-methyl-2,6-di-O-sulpho-α-D-(glucopyranosyl)-(1-4)-O-(3-O-methyl-2,6-di-O-sulpho-β-D-(glucopyranosyl)-(1-4)]$_2$-[O-(2,3,6-tri-O-methyl-α-D-(glucopyranosyl)-(1-4)-O-(2,3,6-tri-O-methyl-β-D-glucopyranosyl)-(1-4)]$_2$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-a-D-glucopyranosyl)-(1-4)-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-[O-(3-O-methyl-2,6-di-O-sulpho-α-D-(glucopyranosyl)-(1-4)-O-(3-O-methyl-2,6-di-O-sulpho-β-D-(glucopyranosyl)-(1-4)]$_2$-[O-(2,3,6-tri-O-methyl-α-D-(glucopyranosyl)-(1-4)-O-(2,3,6-tri-O-methyl-β-D-glucopyranosyl)-(1-4)]$_3$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-a-D-glucopyranosyl)-(1-4)-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-O-(3-O-methyl-2,6-di-O-sulpho-α-D-(glucopyranosyl)-(1-4)-O-(3-O-methyl-2,6-di-O-sulpho-β-D-(glucopyranosyl)-(1-4)-[O-(2,3,6-tri-O-methyl-α-D-(glucopyranosyl)-(1-4)-O-(2,3,6-tri-O-methyl-β-D-glucopyranosyl)-(1-4)]$_4$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-a-D-glucopyranosyl)-(1-4)-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-O-(3-O-methyl-2,6-di-O-sulpho-α-D-(glucopyranosyl)-(1-4)-O-(3-O-methyl-2,6-di-O-sulpho-β-D-(glucopyranosyl)-(1-4)-[O-(2,3,6-tri-O-methyl-α-D-(glucopyranosyl)-(1-4)-O-(2,3,6-tri-O-methyl-β-D-glucopyranosyl)-(1-4)]$_3$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-α-D-glucopyranosyl)-(1-4)-(2,3-di-O-methyl-a-L-idopyranosyluronic acid)-(1-4)-2,3,6-tri-O-sulpho-a-D-glucopyranoside, sodium salt Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-[O-(2,3,6-tri-O-methyl-α-D-(glucopyranosyl)-(1-4)-O-(2,3,6-tri-O-methyl-β-D-(glucopyranosyl)-(1-4)]$_4$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-a-D-(glucopyranosyl)-(1-4)-(2,3-di-O-methyl-a-L-idopyranosyluronic acid)-(1-4)-2,3,6-tri-O-sulpho-a-D-glucopyranoside, sodium salt, and Methyl O-(3-O-methyl-2,4,6-tri-O-sulpho-α-D-(glucopyranosyl)-(1-4)-O-(3-O-methyl-2,6-di-O-sulpho-β-D-(glucopyranosyl)-(1-4)-[O-(2,3,6-tri-O-methyl-α-D-(glucopyranosyl)-(1-4)-O-(2,3,6-tri-O-methyl-β-D-(glucopyranosyl)-(1-4)]$_5$-O-2,3-di-O-methyl-6-sulpho-α-D-(glucopyranosyl)-(1-4)-O-(2,3-di-O-methyl-b-D-glucopyranosyluronic acid)-(1-4)-O-(2,3,6-tri-O-sulpho-a-D-(glucopyranosyl)-(1-4)-(2,3-di-O-methyl-a-L-idopyranosyluronic acid)-(1-4)-2,3,6-tri-O-sulpho-a-D-glucopyranoside, sodium salt.

10. A process for the preparation of a polysaccharide of formula (I) according to claim 2, wherein, in a first step, a fully protected precursor of the desired polysaccharide (I), containing a protected precursor of the Pe region bonded at its non-reducing end to a protected precursor of the sulphated polysaccharide Po, is synthesized and, in a second step, the carboxylic acid functions are deprotected and the sulpho groups are introduced and/or deprotected.

11. Compound of formula

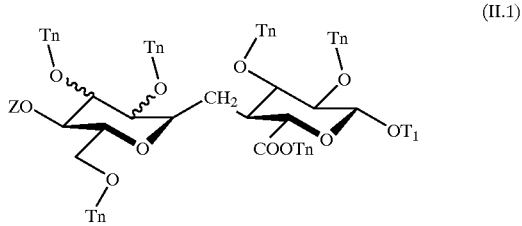

(II.1)

in which $T_1$ and $T_n$ which may be identical or different, represent a temporary, semi-permanent or permanent substituent, and Z is a protecting group for a hydroxyl function.

12. Compound of formula:

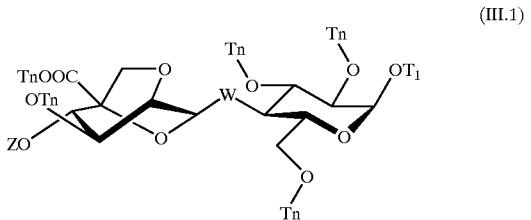

(III.1)

zin which $T_1$ and $T_n$, which may be identical or different, represent a temporary, semi-permanent or permanent substituent, Z is a protecting group for a hydroxyl function.

13. Pharmaceutical compositions containing, as active principle, a polysaccharide or salt according to claim 1, in the form of a salt with a pharmaceutically acceptable base or in acid form, in combination or as a mixture with an inert, non-toxic, pharmaceutically acceptable excipient.

14. Pharmaceutical composition according to claim 13, in the form of dosage units, in which the active principle is mixed with at least one pharmaceutical excipient.

15. Composition according to claim 14, in which each dosage unit contains from 0.1 to 100 mg of active principle.

16. Composition according to claim 15, in which each dosage unit contains from 0.5 to 50 mg of active principle.

17. A Method for the treatment of pathologies which are dependent on disfunctioning of coagulation which comprises administering to a patient in need of such treatment an effective amount of a polysaccharide or salt according to claim 1.

18. A Method for the treatment of pathologies which are dependent on disfunctioning of coagulation which comprises administering to a patient in need of such treatment an effective amount of a polysaccharide or salt according to claim 2.

19. A Method for the treatment of pathologies which are dependent on disfunctioning of coagulation which comprises administering to a patient in need of such treatment an effective amount of a polysaccharide or salt according to claim 3.

20. A Method for the treatment of pathologies which are dependent on disfunctioning of coagulation which comprises administering to a patient in need of such treatment an effective amount of a polysaccharide or salt according to claim 4.

21. A Method for the treatment of pathologies which are dependent on disfunctioning of coagulation which comprises administering to a patient in need of such treatment an effective amount of a polysaccharide or salt according to claim 5.

22. A Method for the treatment of pathologies which are dependent on disfunctioning of coagulation which comprises administering to a patient in need of such treatment an effective amount of a polysaccharide or salt according to claim 6.

23. A Method for the treatment of pathologies which are dependent on disfunctioning of coagulation which comprises administering to a patient in need of such treatment an effective amount of a polysaccharide or salt according to claim 7.

24. A Method for the treatment of pathologies which are dependent on disfunctioning of coagulation which comprises administering to a patient in need of such treatment an effective amount of a polysaccharide or salt according to claim 8.

25. A Method for the treatment of pathologies which are dependent on disfunctioning of coagulation which comprises administering to a patient in need of such treatment an effective amount of a polysaccharide or salt according to claim 9.

26. Pharmaceutical compositions containing, as active principle, a polysaccharide or salt according to claim 2, in the form of a salt with a pharmaceutically acceptable base or in acid form, in combination or as a mixture with an inert, non-toxic, pharmaceutically acceptable excipient.

27. Pharmaceutical compositions containing, as active principle, a polysaccharide or salt according to claim 3, in the form of a salt with a pharmaceutically acceptable base or in acid form, in combination or as a mixture with an inert, non-toxic, pharmaceutically acceptable excipient.

28. Pharmaceutical compositions containing, as active principle, a polysaccharide or salt according to claim 4, in the form of a salt with a pharmaceutically acceptable base or in acid form, in combination or as a mixture with an inert, non-toxic, pharmaceutically acceptable excipient.

29. Pharmaceutical compositions containing, as active principle, a polysaccharide or salt according to claim 5, in the form of a salt with a pharmaceutically acceptable base or in acid form, in combination or as a mixture with an inert, non-toxic, pharmaceutically acceptable excipient.

30. Pharmaceutical compositions containing, as active principle, a polysaccharide or salt according to claim 6, in the form of a salt with a pharmaceutically acceptable base or in acid form, in combination or as a mixture with an inert, non-toxic, pharmaceutically acceptable excipient.

31. Pharmaceutical compositions containing, as active principle, a polysaccharide or salt according to claim 7, in the form of a salt with a pharmaceutically acceptable base or in acid form, in combination or as a mixture with an inert, non-toxic, pharmaceutically acceptable excipient.

32. Pharmaceutical compositions containing, as active principle, a polysaccharide or salt according to claim 8 in the form of a salt with a pharmaceutically acceptable base or in acid form, in combination or as a mixture with an inert, non-toxic, pharmaceutically acceptable excipient.

33. Pharmaceutical compositions containing, as active principle, a polysaccharide or salt according to claim 9, in the form of a salt with a pharmaceutically acceptable base or in acid form, in combination or as a mixture with an inert, non-toxic, pharmaceutically acceptable excipient.

* * * * *